US012642456B2

(12) United States Patent
Baker et al.

(10) Patent No.: US 12,642,456 B2
(45) Date of Patent: *Jun. 2, 2026

(54) APPLICATORS FOR APPLYING TRANSCUTANEOUS ANALYTE SENSORS AND ASSOCIATED METHODS OF MANUFACTURE

(71) Applicant: DexCom, Inc., San Diego, CA (US)

(72) Inventors: Joseph J. Baker, Vista, CA (US); Philip Thomas Pupa, San Diego, CA (US); Timothy Joseph Goldsmith, San Diego, CA (US); Jonathan Bodnar, Keller, TX (US); Jason Halac, San Diego, CA (US); John Michael Gray, San Diego, CA (US); Neal Davis Johnston, Dallas, TX (US); Justen Deering England, San Francisco, CA (US); Peter C. Simpson, Cardiff by the Sea, CA (US); Paul V. Neale, San Diego, CA (US); Jennifer Blackwell, San Diego, CA (US); Maria Noel Brown Wells, San Diego, CA (US); Kenneth Pirondini, San Diego, CA (US); Andrew Michael Reinhardt, Santee, CA (US); Mark Douglas Kempkey, Vista, CA (US); Young Woo Lee, San Diego, CA (US); Warren Terry, Poway, CA (US); Patrick John Castagna, San Diego, CA (US); David A. Keller, Encinitas, CA (US); Randall Scott Koplin, Middleton, WI (US); Andrew Joncich, Madison, WI (US); Nirav Bhatt, Irvine, CA (US)

(73) Assignee: DexCom, Inc., San Diego, CA (US)

( * ) Notice: Subject to any disclaimer, the term of this patent is extended or adjusted under 35 U.S.C. 154(b) by 403 days.

This patent is subject to a terminal disclaimer.

(21) Appl. No.: 17/842,624

(22) Filed: Jun. 16, 2022

(65) Prior Publication Data

US 2022/0322975 A1     Oct. 13, 2022

Related U.S. Application Data

(63) Continuation of application No. 16/011,578, filed on Jun. 18, 2018, now Pat. No. 11,395,607, which is a
(Continued)

(51) Int. Cl.
| | |
|---|---|
| *A61B 5/145* | (2006.01) |
| *A61B 5/00* | (2006.01) |
| *A61B 17/34* | (2006.01) |

(52) U.S. Cl.
CPC ........ *A61B 5/14503* (2013.01); *A61B 5/0004* (2013.01); *A61B 5/14532* (2013.01);
(Continued)

(58) Field of Classification Search
CPC .......... A61B 5/6848; A61B 2560/0406; A61B 2560/063; A61B 2562/12;
(Continued)

(56) References Cited

U.S. PATENT DOCUMENTS

| | | | |
|---|---|---|---|
| 3,759,375 A | 9/1973 | Nappi | |
| 3,815,315 A | 6/1974 | Glick | |
(Continued)

FOREIGN PATENT DOCUMENTS

| | | |
|---|---|---|
| CN | 307437861 | 7/2022 |
| CN | 307742928 | 12/2022 |
(Continued)

OTHER PUBLICATIONS

International Search Report and Written Opinion for Application No. PCT/US2014/072113 mailed on Apr. 1, 2015, 9 pages.
(Continued)

*Primary Examiner* — Thomas Mcevoy
(74) *Attorney, Agent, or Firm* — Snell & Wilmer LLP

(57) ABSTRACT

Applicators for applying an on-skin assembly to skin of a host and methods of their use and/or manufacture are
(Continued)

provided. An applicator includes an insertion assembly configured to insert at least a portion of the on-skin assembly into the skin of the host, a housing configured to house the insertion assembly, the housing comprising an aperture through which the on-skin assembly can pass, an actuation member configured to, upon activation, cause the insertion assembly to insert at least the portion of the on-skin assembly into the skin of the host, and a sealing element configured to provide a sterile barrier and a vapor barrier between an internal environment of the housing and an external environment of the housing.

19 Claims, 40 Drawing Sheets

Related U.S. Application Data continuation of application No. 16/011,527, filed on Jun. 18, 2018, now Pat. No. 11,452,466.

(60) Provisional application No. 62/521,969, filed on Jun. 19, 2017.

(52) U.S. Cl.
CPC .......... *A61B 5/6833* (2013.01); *A61B 5/6849* (2013.01); *A61B 5/742* (2013.01); *A61B 17/3468* (2013.01); *A61B 5/14546* (2013.01); *A61B 5/6848* (2013.01); *A61B 5/688* (2013.01); *A61B 2560/0406* (2013.01); *A61B 2560/063* (2013.01); *A61B 2562/12* (2013.01); *A61B 2562/242* (2013.01)

(58) Field of Classification Search
CPC ............ A61B 2562/242; A61B 5/6801; A61B 5/6846; A61B 5/6847; A61B 5/688; A61B 2562/247; A61B 2562/24; A61B 5/145–157; A61L 2202/24
See application file for complete search history.

(56) References Cited

U.S. PATENT DOCUMENTS

| | | | |
|---|---|---|---|
| 3,872,966 A | 3/1975 | Gordon et al. | |
| 3,991,881 A | 11/1976 | Augurt | |
| 4,206,844 A | 6/1980 | Thukamoto et al. | |
| 4,353,694 A | 10/1982 | Pelerin | |
| 4,511,035 A | 4/1985 | Alpern | |
| 5,390,671 A | 2/1995 | Lord et al. | |
| 5,464,580 A | 11/1995 | Popescu et al. | |
| 5,575,403 A | 11/1996 | Charlton et al. | |
| 5,586,553 A | 12/1996 | Halili et al. | |
| 5,697,495 A | 12/1997 | Abrams et al. | |
| 5,868,253 A | 2/1999 | Krueger et al. | |
| 6,175,752 B1 | 1/2001 | Say et al. | |
| 6,892,085 B2 | 5/2005 | McIvor et al. | |
| D579,541 S | 10/2008 | Mogensen et al. | |
| 7,494,465 B2 | 2/2009 | Brister et al. | |
| 7,497,827 B2 | 3/2009 | Brister et al. | |
| D603,050 S | 10/2009 | Chen | |
| 7,774,145 B2 | 8/2010 | Brauker et al. | |
| 8,069,980 B2 | 12/2011 | Stopek et al. | |
| 8,252,229 B2 | 8/2012 | Thomas et al. | |
| 8,262,618 B2 | 9/2012 | Scheurer | |
| 8,275,437 B2 | 9/2012 | Brauker et al. | |
| 8,396,528 B2 | 3/2013 | Kamath et al. | |
| 8,478,377 B2 | 7/2013 | Shariati et al. | |
| 8,535,269 B2 | 9/2013 | Scheurer et al. | |
| D691,710 S | 10/2013 | White | |
| D693,927 S | 11/2013 | Wilson et al. | |
| D694,397 S | 11/2013 | White et al. | |
| 8,684,172 B2 | 4/2014 | Yao | |
| D705,422 S | 5/2014 | Burton et al. | |
| 8,764,657 B2 | 7/2014 | Curry et al. | |
| 8,783,102 B2 | 7/2014 | Heck et al. | |
| 8,790,311 B2 | 7/2014 | Gyrn | |
| 8,802,006 B2 | 8/2014 | Thomas et al. | |
| 8,960,422 B2 | 2/2015 | Reyhan et al. | |
| 9,101,305 B2 | 8/2015 | Larson et al. | |
| 9,239,252 B2 | 1/2016 | Koga | |
| 9,265,453 B2 | 2/2016 | Curry et al. | |
| 9,357,951 B2 | 6/2016 | Simpson et al. | |
| 9,402,544 B2 | 8/2016 | Yee et al. | |
| 9,402,570 B2 | 8/2016 | Pace et al. | |
| 9,474,524 B2 | 10/2016 | Fischer et al. | |
| 9,546,031 B2 | 1/2017 | Healy | |
| 9,636,068 B2 | 5/2017 | Yee et al. | |
| D794,800 S | 8/2017 | Gobrecht et al. | |
| 9,717,843 B2 | 8/2017 | Grucela et al. | |
| 10,029,043 B2 | 7/2018 | Grucela et al. | |
| 10,136,816 B2 | 11/2018 | Bernstein et al. | |
| 10,245,025 B2 | 4/2019 | Prikril et al. | |
| 10,300,507 B2 | 5/2019 | Petisce et al. | |
| D854,146 S | 7/2019 | Stonecipher et al. | |
| D888,252 S | 6/2020 | Terry et al. | |
| D891,612 S | 7/2020 | Stonecipher et al. | |
| 10,813,576 B2 | 10/2020 | Brister et al. | |
| 10,813,577 B2 | 10/2020 | Brister et al. | |
| 10,827,956 B2 | 11/2020 | Brister et al. | |
| D924,406 S | 7/2021 | Yee et al. | |
| D926,326 S | 7/2021 | Terry et al. | |
| D937,422 S | 11/2021 | Huang et al. | |
| 11,166,657 B2 | 11/2021 | Halac et al. | |
| 11,179,107 B2 | 11/2021 | Chae et al. | |
| D948,722 S | 4/2022 | Donnay et al. | |
| D957,642 S | 7/2022 | Thomas et al. | |
| 11,395,067 B2 | 7/2022 | Kawaguchi et al. | |
| D980,986 S | 3/2023 | Rao et al. | |
| 11,602,291 B2 | 3/2023 | Halac et al. | |
| D982,762 S | 4/2023 | Rao et al. | |
| 11,654,270 B2 | 5/2023 | Mansfield, III et al. | |
| 11,690,573 B2 | 7/2023 | Rodriguez et al. | |
| 11,738,148 B2 | 8/2023 | Goldin et al. | |
| D999,913 S | 9/2023 | Rao | |
| D1,006,235 S | 11/2023 | Rao et al. | |
| 11,904,127 B2 | 2/2024 | Mansfield, III et al. | |
| 11,963,762 B2 | 4/2024 | Baker et al. | |
| 11,992,341 B2 | 5/2024 | Chae et al. | |
| D1,033,641 S | 7/2024 | Morelock | |
| D1,052,736 S | 11/2024 | Terry et al. | |
| 2002/0119711 A1 | 8/2002 | Vanantwerp et al. | |
| 2003/0028152 A1* | 2/2003 | Alesi ................ A61B 5/150732 600/576 |
| 2003/0060781 A1 | 3/2003 | Mogensen et al. | |
| 2003/0138347 A1 | 7/2003 | Lin | |
| 2004/0173487 A1 | 9/2004 | Johnson et al. | |
| 2004/0204687 A1 | 10/2004 | Mogensen et al. | |
| 2005/0096586 A1 | 5/2005 | Trautman et al. | |
| 2005/0124936 A1 | 6/2005 | Mogensen et al. | |
| 2005/0131347 A1 | 6/2005 | Marano-Ford et al. | |
| 2005/0226763 A1 | 10/2005 | Raynal-Olive et al. | |
| 2006/0036145 A1 | 2/2006 | Brister et al. | |
| 2006/0057022 A1 | 3/2006 | Williams et al. | |
| 2006/0142651 A1 | 6/2006 | Brister et al. | |
| 2006/0155336 A1 | 7/2006 | Heath | |
| 2007/0142854 A1 | 6/2007 | Schraga | |
| 2007/0203966 A1 | 8/2007 | Brauker et al. | |
| 2007/0289894 A1 | 12/2007 | Tennant et al. | |
| 2008/0009805 A1 | 1/2008 | Ethelfeld | |
| 2008/0042837 A1 | 2/2008 | Burke | |
| 2008/0114280 A1 | 5/2008 | Stafford | |
| 2008/0121553 A1 | 5/2008 | Gobel | |
| 2008/0249473 A1 | 10/2008 | Rutti et al. | |
| 2009/0124879 A1 | 5/2009 | Brister et al. | |
| 2009/0163874 A1 | 6/2009 | Krag et al. | |
| 2009/0254041 A1 | 10/2009 | Krag et al. | |
| 2009/0257911 A1 | 10/2009 | Thomas et al. | |
| 2009/0273447 A1 | 11/2009 | Selker et al. | |
| 2010/0179508 A1 | 7/2010 | Mogensen et al. | |
| 2010/0324392 A1 | 12/2010 | Yee et al. | |
| 2011/0006900 A1 | 1/2011 | Nyffeler et al. | |

(56) References Cited

U.S. PATENT DOCUMENTS

| | | |
|---|---|---|
| 2011/0137257 A1 | 6/2011 | Gyrn et al. |
| 2011/0152778 A1 | 6/2011 | Gyrn |
| 2011/0213225 A1 | 9/2011 | Bernstein et al. |
| 2011/0276027 A1 | 11/2011 | Trautman et al. |
| 2011/0319729 A1 | 12/2011 | Donnay et al. |
| 2012/0001731 A1 | 1/2012 | Potyrailo et al. |
| 2012/0190951 A1 | 7/2012 | Curry et al. |
| 2012/0227358 A1 | 9/2012 | Larson et al. |
| 2013/0116524 A1 | 5/2013 | Cole et al. |
| 2013/0150691 A1 | 6/2013 | Pace et al. |
| 2013/0167768 A1 | 7/2013 | Smith et al. |
| 2013/0233736 A1 | 9/2013 | Hess et al. |
| 2013/0264226 A1 | 10/2013 | Prikril et al. |
| 2014/0034545 A1 | 2/2014 | Pawlowski et al. |
| 2014/0107579 A1 | 4/2014 | Lanigan et al. |
| 2014/0190861 A1 | 7/2014 | Carrel et al. |
| 2014/0203831 A1 | 7/2014 | Lee |
| 2014/0276580 A1 | 9/2014 | Le et al. |
| 2015/0129437 A1 | 5/2015 | Clamp et al. |
| 2015/0147602 A1 | 5/2015 | Bianchi et al. |
| 2015/0164545 A1 | 6/2015 | Gyrn |
| 2016/0015897 A1 | 1/2016 | Swanson et al. |
| 2016/0058344 A1 | 3/2016 | Peterson et al. |
| 2016/0106349 A1 | 4/2016 | Pryor et al. |
| 2016/0128615 A1 | 5/2016 | Curry et al. |
| 2016/0331283 A1 | 11/2016 | Rao et al. |
| 2017/0020458 A1 | 1/2017 | Yee et al. |
| 2017/0035964 A1 | 2/2017 | Gyrn et al. |
| 2017/0042457 A1 | 2/2017 | Pace et al. |
| 2017/0065767 A1 | 3/2017 | Harttig et al. |
| 2017/0112531 A1 | 4/2017 | Schoonmaker et al. |
| 2017/0112534 A1 | 4/2017 | Schoonmaker et al. |
| 2017/0188910 A1 | 7/2017 | Halac et al. |
| 2017/0188912 A1 | 7/2017 | Halac et al. |
| 2018/0235520 A1 | 8/2018 | Rao et al. |
| 2018/0256820 A1 | 9/2018 | Schader et al. |
| 2018/0296749 A1 | 10/2018 | Grucela et al. |
| 2018/0360357 A1 | 12/2018 | Baker et al. |
| 2018/0360358 A1 | 12/2018 | Baker et al. |
| 2018/0360493 A1 | 12/2018 | Baker et al. |
| 2018/0368774 A1 | 12/2018 | Gray et al. |
| 2019/0008217 A1 | 1/2019 | Cui et al. |
| 2019/0083017 A1 | 3/2019 | Walter |
| 2019/0270533 A1 | 9/2019 | Lu et al. |
| 2019/0307381 A1 | 10/2019 | Boock et al. |
| 2019/0320955 A1 | 10/2019 | Pryor et al. |
| 2019/0342637 A1 | 11/2019 | Halac et al. |
| 2020/0196919 A1 | 6/2020 | Rao et al. |
| 2021/0186424 A1 | 6/2021 | Rodriguez et al. |
| 2021/0236729 A1 | 8/2021 | Kiani et al. |
| 2022/0117627 A1 | 4/2022 | Garai |
| 2022/0225899 A1 | 7/2022 | Peterson et al. |
| 2022/0379019 A1 | 12/2022 | Lanigan et al. |
| 2023/0277094 A1 | 9/2023 | Huang et al. |
| 2023/0330339 A1 | 10/2023 | Cattermole et al. |
| 2023/0337984 A1 | 10/2023 | Hefner et al. |
| 2023/0380728 A1 | 11/2023 | Mujeeb-U-Rahman et al. |
| 2024/0130643 A1 | 4/2024 | Chae et al. |
| 2024/0138716 A1 | 5/2024 | Chae et al. |
| 2024/0156376 A1 | 5/2024 | Metzmaker et al. |

FOREIGN PATENT DOCUMENTS

| | | | |
|---|---|---|---|
| EP | 4299081 | B1 | 8/2025 |
| JP | 2006527036 | A | 11/2006 |
| JP | 2008127024 | A | 6/2008 |
| JP | 2008220961 | A | 9/2008 |
| JP | 2013523216 | A | 6/2013 |
| JP | 2013524872 | A | 6/2013 |
| JP | D1484253 | | 10/2013 |
| JP | 2014069083 | A | 4/2014 |
| JP | 2015509011 | A | 3/2015 |
| JP | 2019528842 | A | 10/2019 |
| JP | 1723753 | S | 9/2022 |
| JP | 7562259 | B2 | 10/2024 |
| KR | 301000496 | | 3/2019 |
| KR | 301024160 | | 9/2019 |
| KR | 301182850 | | 9/2022 |
| KR | 301212065 | | 4/2023 |
| KR | 3012899020000 | | 1/2025 |
| WO | WO-2009095701 | A1 | 8/2009 |
| WO | WO-2011119896 | A1 | 9/2011 |
| WO | WO-2016024085 | A1 | 2/2016 |
| WO | WO-2018236769 | A1 | 12/2018 |
| WO | WO-D214177001 | | 12/2020 |
| WO | WO-D240867 | | 10/2024 |

OTHER PUBLICATIONS

International Preliminary Report on Patentability for Application No. PCT/US2014/072113 mailed on Aug. 25, 2016, 7 pages.

International Preliminary Report on Patentability for Application No. PCT/US2018/038117 mailed Jan. 2, 2020, 12 pages.

International Search Report and Written opinion for Application No. PCT/US2018/038117 mailed Nov. 28, 2018, 15 pages.

Dexcom, "Dexcom G5—How To Insert Your Sensor," YouTube. com [Online], Oct. 19, 2015, 3 pages, Retrieved from the Internet: https://www.youtube.com/watch?v=9_8t_HSG-uE.

Dexcom, "Dexcom G6—How To Insert the Sensor and Attach the Transmitter," YouTube.com [Online], May 11, 2018, 3 pages, Retrieved from the Internet: URL: https://www.youtube.com/watch?v=s6a FY_wffhs.

Dexcom UK, "Dexcom Event: Dexcom G7 CGM System," YouTube. com [Online], Oct. 4, 2022, 2 pages, Retrieved from the Internet: URL: https://www.youtube.com/watchv=dYqNUf0paAU.

Dr. John Campbell, "Fitting the Freestyle Libre One Sensor," YouTube.com [Online], May 22, 2019, 3 pages, Retrieved from the Internet: URL: https://www.youtube.com/watch?v=rQFwaTbPkR I.

NS Medical Staff Writer, "FDA Approves Abbott's Freestyle Libre 14-Day Flash Glucose Monitoring System," NS Medical Devices, Jul. 30, 2018, 1 page, Retrieved from the Internet: URL: https://www.nsmedicaldevices.com/news/fda-approves-abbotts-freestyle-libre-14-day-flash-glucose-monitoring-system/.

Scheiner G., "The Dexcom G7: What to Expect," integrateddiabetes. com [Online], Apr. 2022, 5 pages, Retrieved from the Internet: URL: https://integrateddiabetes.com/the-dexcom-g7-what-to-expect/.

Dexcom, "Dexcom G7 Receiver—How to Get Started and Set Up the Receiver," YouTube.com, Feb. 16, 2023, 04 Pages, Retrieved from the Internet: URL: https://www.youtube.com/watch?v=2A6CQfCOKUc.

Garg, "Accuracy and Safety of Dexcom G7," liebertpub.com, May 31, 2022, 01 Page, Retrieved from the Internet: URL: https://www.liebertpub.com/doi/full/10.1089/dia.2022.0011.

Herrick, "Dexcom G7 Continuous Glucose Monitor Cleared by the FDA," breakthrought1d.org, Dec. 8, 2022, 01 Page, Retrieved from the Internet: URL: https://www.breakthrought1d.org/news-and-updates/dexcom-g7-continuous-glucose-monitor-cleared-fda/.

Medtronic, "Medtronic—How to Insert the Guardian Connect CGM," YouTube.com, Mar. 30, 2017, 02 Pages, Retrieved from the Internet: URL: https://www.youtube.com/watch?v=h7zu8azTKac.

* cited by examiner

700

700

1500

1504

1524

1500

1504

1550

1600

1604

1624

1600

1604

106

1624

1650

1662

2000

2064

2004

2024

2000

2050

2004

2200

2264

2204

2224

2200

2264

2204

106

2262

2224

2500

2550

25B

2550

2924

2922

2912

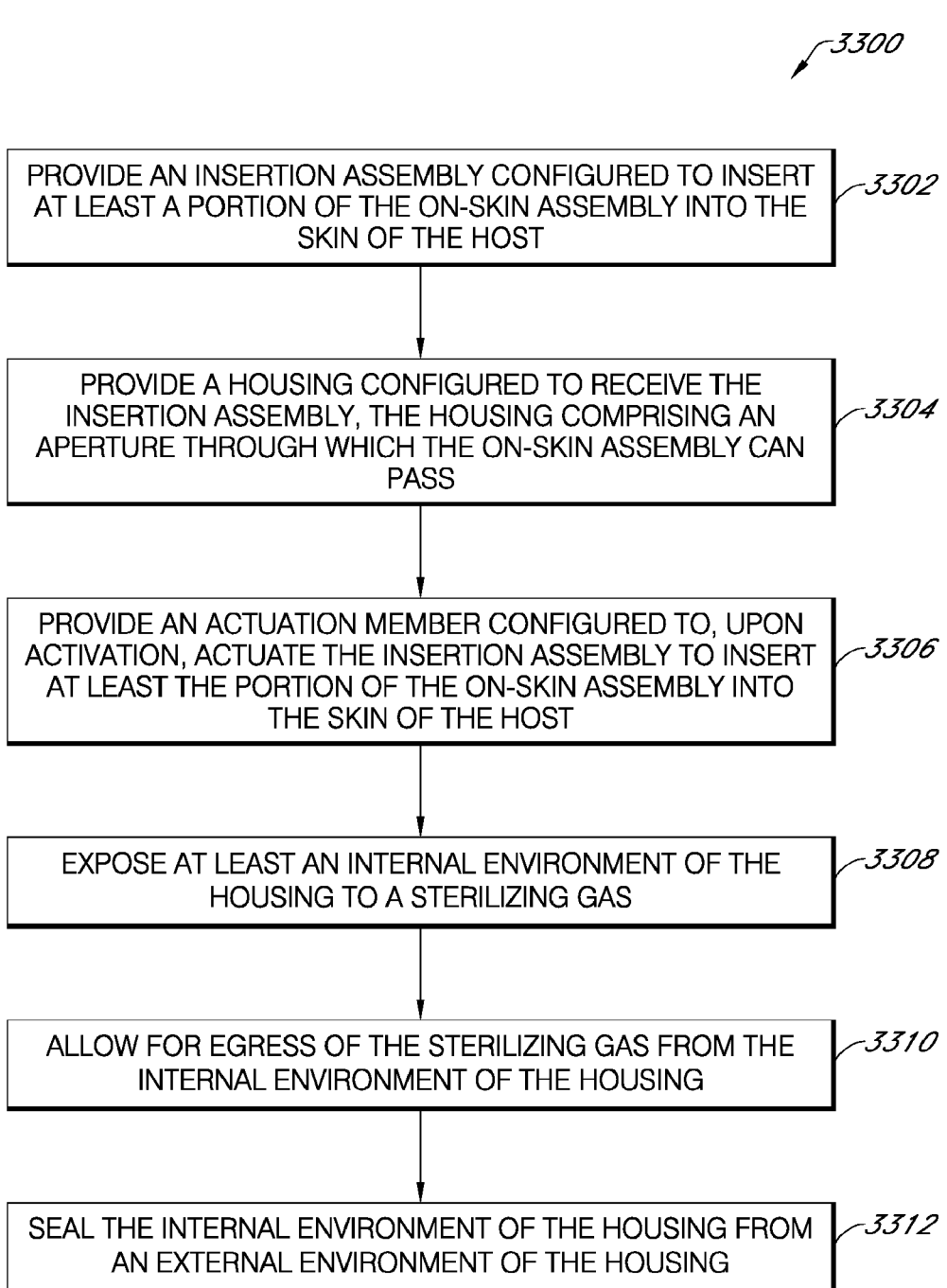

*3300*

PROVIDE AN INSERTION ASSEMBLY CONFIGURED TO INSERT AT LEAST A PORTION OF THE ON-SKIN ASSEMBLY INTO THE SKIN OF THE HOST *3302*

PROVIDE A HOUSING CONFIGURED TO RECEIVE THE INSERTION ASSEMBLY, THE HOUSING COMPRISING AN APERTURE THROUGH WHICH THE ON-SKIN ASSEMBLY CAN PASS *3304*

PROVIDE AN ACTUATION MEMBER CONFIGURED TO, UPON ACTIVATION, ACTUATE THE INSERTION ASSEMBLY TO INSERT AT LEAST THE PORTION OF THE ON-SKIN ASSEMBLY INTO THE SKIN OF THE HOST *3306*

EXPOSE AT LEAST AN INTERNAL ENVIRONMENT OF THE HOUSING TO A STERILIZING GAS *3308*

ALLOW FOR EGRESS OF THE STERILIZING GAS FROM THE INTERNAL ENVIRONMENT OF THE HOUSING *3310*

SEAL THE INTERNAL ENVIRONMENT OF THE HOUSING FROM AN EXTERNAL ENVIRONMENT OF THE HOUSING *3312*

FIG. 33

APPLICATORS FOR APPLYING TRANSCUTANEOUS ANALYTE SENSORS AND ASSOCIATED METHODS OF MANUFACTURE

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/011,578, filed Jun. 18, 2018, which is a continuation of U.S. application Ser. No. 16/011,527, filed Jun. 18, 2018, which claims the benefit of U.S. Provisional Application No. 62/521,969, filed Jun. 19, 2017, titled "APPLICATORS FOR APPLYING TRANSCUTANEOUS ANALYTE SENSORS AND ASSOCIATED METHODS OF MANUFACTURES." The aforementioned applications are incorporated by reference herein in their entireties, and are hereby expressly made a part of this specification.

FIELD

An applicator for applying an on-skin assembly to skin of a host and methods of their use and/or manufacture are provided. More particularly, apparatuses for applying a transcutaneous analyte assembly to skin of a host for accurately measuring blood glucose of the host and methods of their use and/or manufacture are provided.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are spread so far apart that the person with diabetes likely finds out too late of a hyperglycemic or hypoglycemic condition, sometimes incurring dangerous side effects. Glucose levels may be alternatively monitored continuously by a sensor system including an on-skin sensor assembly. The sensor system may have a wireless transmitter which transmits measurement data to a receiver which can process and display information based on the measurements.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or difficulties presented above.

SUMMARY

The present apparatuses and methods of manufacture relate to systems and methods for measuring an analyte in a host, systems and methods for manufacturing a transcutaneous analyte measurement system, and systems and methods for applying a transcutaneous analyte measurement system to skin of a host. The various embodiments of the present systems and methods have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

According to a first aspect, an applicator for applying an on-skin assembly to skin of a host is provided. The applicator includes an insertion assembly configured to insert at least a portion of the sensor assembly into the skin of the host. The applicator includes a housing configured to house the insertion assembly. The housing includes an aperture through which the sensor assembly is configured to pass. The applicator includes an actuation member configured to, upon activation, cause the insertion assembly to insert at least the portion of the sensor assembly into the skin of the host. The applicator includes a sealing element configured to provide a sterile barrier and a vapor barrier between an internal environment of the housing and an external environment of the housing.

In some embodiments, the sealing element is releasable from the applicator. In some embodiments, the applicator further includes the on-skin assembly. In some embodiments, the on-skin assembly comprises a sensor. In some embodiments, the on-skin assembly comprises a transmitter. In some embodiments the on-skin assembly comprises an adhesive layer configured to adhere the on-skin assembly to the skin of the host. In some embodiments, the applicator further includes a support member configured to inhibit at least lateral movement of the insertion assembly. In some embodiments, the support member comprises an elastomeric membrane. In some embodiments, the insertion assembly comprises a needle. In some embodiments, the applicator further includes one or more ridges or recesses configured to provide a tactile indication of grip for the host. In some embodiments, the applicator has a cross-sectional shape configured to provide a tactile indication of grip for the host. In some embodiments, the applicator further includes at least one protrusion configured to inhibit rolling of the applicator. In some embodiments, the housing comprises a vent configured to be permeable to a sterilizing gas. In some embodiments, the sealing element is configured to seal the vent. In some embodiments, the sealing element is configured to seal both the aperture and the actuation member. In some embodiments, the actuation member comprises a material that is permeable to a sterilizing gas. In some embodiments, the sealing element comprises at least one of a metallic foil (e.g. aluminum, titanium), a metallic substrate, aluminum oxide coated polymer, parylene, a polymer coated with a metal applied via vapor metallization, silicon dioxide coated polymer, or any material having a moisture vapor transmission rate less than 10 grams/100 in^2 or preferably less than 1 grams/100 in^2.

In some embodiments, the sealing element comprises a removable cap configured to couple with a portion of the housing. In some embodiments, the removable cap is configured to couple with a proximal portion of the housing. In some embodiments, the removable cap is configured to couple with a distal portion of the housing. In some embodiments, the removable cap is configured to couple with the housing in a single axial orientation. In some embodiments, the removable cap is configured to couple with the portion of the housing via threads. In some embodiments, the removable cap is configured to couple with the portion of the housing via a frangible member. In some embodiments, the frangible member is configured to provide a tamper indication when broken. In some embodiments, the sealing element further comprises an o-ring configured to provide a seal between the removable cap and the housing. In some embodiments, the removable cap covers the actuation member.

In some embodiments, the applicator further includes a tamper indicator. In some embodiments, the sealing element comprises a first layer being permeable to a sterilizing gas and a second layer being substantially impermeable to water vapor. In some embodiments, the sealing element comprises a first layer being substantially impermeable to water vapor and sealing the aperture. In some embodiments, the sealing element further comprises a second layer being substantially impermeable to water vapor and sealing the actuation member. In some embodiments, the sealing element comprises a peelable layer coupled to at least a portion of the housing. In some embodiments, the peelable layer is configured to provide a tamper indication when removed. In some embodiments, the peelable layer is configured to seal a distal opening of the housing. In some embodiments, the peelable layer is configured to further seal the actuation member. In some embodiments, the peelable layer is configured to seal a vent configured to be permeable to a sterilizing gas. In some embodiments, the vent is disposed on a side of the housing. In some embodiments, a porous polymeric component is inserted into the vent.

In some embodiments, the sealing element comprises a flexible member disposed over at least a portion of the housing. In some embodiments, the flexible member comprises an elastomer. In some embodiments, the flexible member covers the actuation member. In some embodiments, the flexible member is operatively coupled to the actuation member. In some embodiments, the flexible member has a bistable configuration so as to provide a visual indication of deployment after activation. In some embodiments, the sealing element comprises a frangible member. In some embodiments, the frangible member covers the actuation member, and wherein removal of the frangible member exposes the actuation member for activation.

In some embodiments, the sealing element comprises a cup having a removable lid. In some embodiments, the cup is configured to be collapsible after removal of the lid. In some embodiments, the cup is configured to seal applicator from an environment outside the cup. In some embodiments, the cup comprises an on-skin assembly alignment feature. In some embodiments, the cup comprises a needle protection feature. In some embodiments, the sealing element comprises a plug configured to couple to the housing via a friction fit.

In some embodiments, the actuation member is disposed on a side of the housing. In some embodiments, the actuation member is disposed on a proximal portion of the housing. In some embodiments, the actuation member is recessed into the proximal portion of the housing. In some embodiments, the actuation member comprises a cap coupled to a proximal portion of the housing. In some embodiments, the actuation member is configured to be activated by moving the cap in a distal direction. In some embodiments, the sealing element further comprises a sealing layer disposed between the cap and the housing. In some embodiments, the cap comprises a protrusion configured to pierce the sealing layer and thereby activate the insertion assembly. In some embodiments, the insertion assembly is driven by a spring force. In some embodiments, the needle is retracted from the insertion assembly after the insertion assembly inserts the on-skin assembly. In some embodiments, the applicator further includes a safety member configured to prevent activation of the actuation member. In some embodiments, the safety member comprises a frangible member, the frangible member being configured to prevent activation of the actuation member, at least until the frangible member is broken.

In some embodiments, the sealing element comprises a first portion comprising a plurality of perforations and an adhesive layer disposed on a first side of the first portion. In some embodiments, the sealing element further comprises a second portion disposed adjacent to the first side of the first portion, the second portion configurable in a first configuration wherein the first portion is spatially separated from the second portion and a second configuration wherein the second portion is adhered to the first portion via the adhesive layer, wherein the sealing element is permeable to a sterilizing gas in the first configuration, and the sealing element is impermeable to the sterilizing gas in the second configuration. In some embodiments, the second portion is configured to transition from the first configuration to the second configuration when the applicator is subjected to a partial vacuum exceeding a threshold. In some embodiments, the housing is disposable.

In a second aspect, a method of manufacturing an applicator configured to apply a sensor assembly to skin of a host is provided. The method includes providing an insertion assembly configured to insert at least a portion of the sensor assembly into the skin of the host. The method includes providing a housing configured to house the insertion assembly. The housing comprising an aperture through which the sensor assembly is configured to pass. The method includes providing an actuation member configured to, upon activation, cause the insertion assembly to insert at least the portion of the sensor assembly into the skin of the host. The method includes providing a releasable sealing element configured to provide a sterile barrier and a vapor barrier between an internal environment of the housing and an external environment of the housing.

In a third aspect, a method of manufacturing an applicator configured to apply a sensor assembly to skin of a host is provided. The method includes providing an insertion assembly configured to insert at least a portion of the sensor assembly into the skin of the host. The method includes providing a housing configured to house the insertion assembly. The housing comprising an aperture through which the sensor assembly is configured to pass. The method includes providing an actuation member configured to, upon activation, cause the insertion assembly to insert at least the portion of the sensor assembly into the skin of the host. The method includes exposing at least an internal environment of the housing to a sterilizing gas. The method includes allowing for egress of the sterilizing gas from the internal environment of the housing. The method includes sealing the internal environment of the housing from an external environment of the housing.

In some embodiments, at least sealing the internal environment of the housing from an external environment of the housing is performed simultaneously for a plurality of applicators. In some embodiments, sealing the internal environment of the housing from an external environment of the housing comprises subjecting the plurality of applicators to a partial vacuum exceeding a threshold such that a sealing element of each of the plurality of applicators transitions from being permeable to the sterilizing gas to being impermeable to the sterilizing gas. In some embodiments, sealing the internal environment of the housing from an external environment of the housing comprises subjecting the plurality of applicators to a physical force sufficient to cause a sealing element of each of the plurality of applicators to transition from a first physical configuration permeable to the sterilizing gas to a second physical configuration impermeable to the sterilizing gas. In some embodiments, sealing the internal environment of the housing from an external environment of the housing comprises subjecting a sealing element, comprising a plurality of perforations, of each the plurality of applicators to a temperature sufficient to at least partially melt each of the sealing elements thereby sealing the plurality of perforations in each of the sealing elements. In some embodiments, sealing the internal environment of the housing from an external environment of the housing comprises subjecting a sealing element, comprising a porous polymeric component, of each of the plurality of applicators to a temperature sufficient to form a sintered layer in the porous polymeric component of each sealing element. In some embodiments, sealing the internal environment of the housing from an external environment of the housing comprises depositing a layer impermeable to the sterilizing gas on at least a portion of each of the plurality of applicators. In some embodiments, the layer comprises at least one of aluminum oxide, parylene, a vapor metallization, silicon dioxide, or a material applied via ion beam sputtering.

In some embodiments, an applicator for applying an on-skin assembly to skin of a host is provided. The applicator may include an insertion assembly configured to insert at least a portion of the on-skin assembly into the skin of the host. The housing may be configured to receive the insertion assembly. The housing may comprise an aperture through which the on-skin assembly is configured to pass. The applicator may comprise an actuation member configured to, upon activation, actuate the insertion assembly to insert at least the portion of the on-skin assembly into the skin of the host. The applicator may comprise a removable cap configured to couple with a portion of the housing. The applicator may comprise a layer comprising a gas permeable material, the sealing element configured to allow for ingress and egress of a sterilizing gas.

In some embodiments, the removable cap includes an aperture located at a bottom end of the removable cap. In some embodiments, the layer is coupled to the bottom of the removable cap and encloses the aperture. The removable cap may include a raised platform from the bottom end of the removable cap. In some embodiments, the raised platform is spaced a predetermined distance from the on-skin assembly. The raised platform may include a plurality of channels. The plurality of channels may be spaced equidistantly along the circumference of the raised platform. The plurality of channels may be configured to allow for ingress of the sterilizing gas into the housing and egress of the sterilizing gas out of the housing.

In some embodiments, the applicator includes a safety feature to prevent actuation of the actuation member. The safety feature can be unlocked by pressing the housing in a distal direction. The pressing of the housing in a distal direction actuates the housing along an inner housing of the applicator. The actuation member may be aligned with a trigger arm, the actuation member configured to laterally actuate and deflect the trigger arm. In some embodiments, the removable cap is configured to couple with a proximal portion of the housing. In some embodiments, the removable cap is configured to couple with a distal portion of the housing.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments.

FIG. 33 is a flowchart illustrating another method of manufacturing an applicator for applying an on-skin assembly to skin of a host, in accordance with some embodiments.

DETAILED DESCRIPTION OF CERTAIN INVENTIVE EMBODIMENTS

The following description and examples illustrate some example embodiments of the disclosed invention in detail. Those of skill in the art will recognize that there are numerous variations and modifications of this invention that are encompassed by its scope. Accordingly, the description of a certain example embodiment should not be deemed to limit the scope of the present invention.

The present application is directed to embodiments of applicators for applying an on-skin assembly to skin of a host as well as methods of their manufacture and use. As will be described in more detail in connection with the figures below, certain features of the described applicators provide novel and inventive solutions to difficulties associated with previous applicator designs and/or methods of their use or manufacture.

System Introduction

Figure 31:
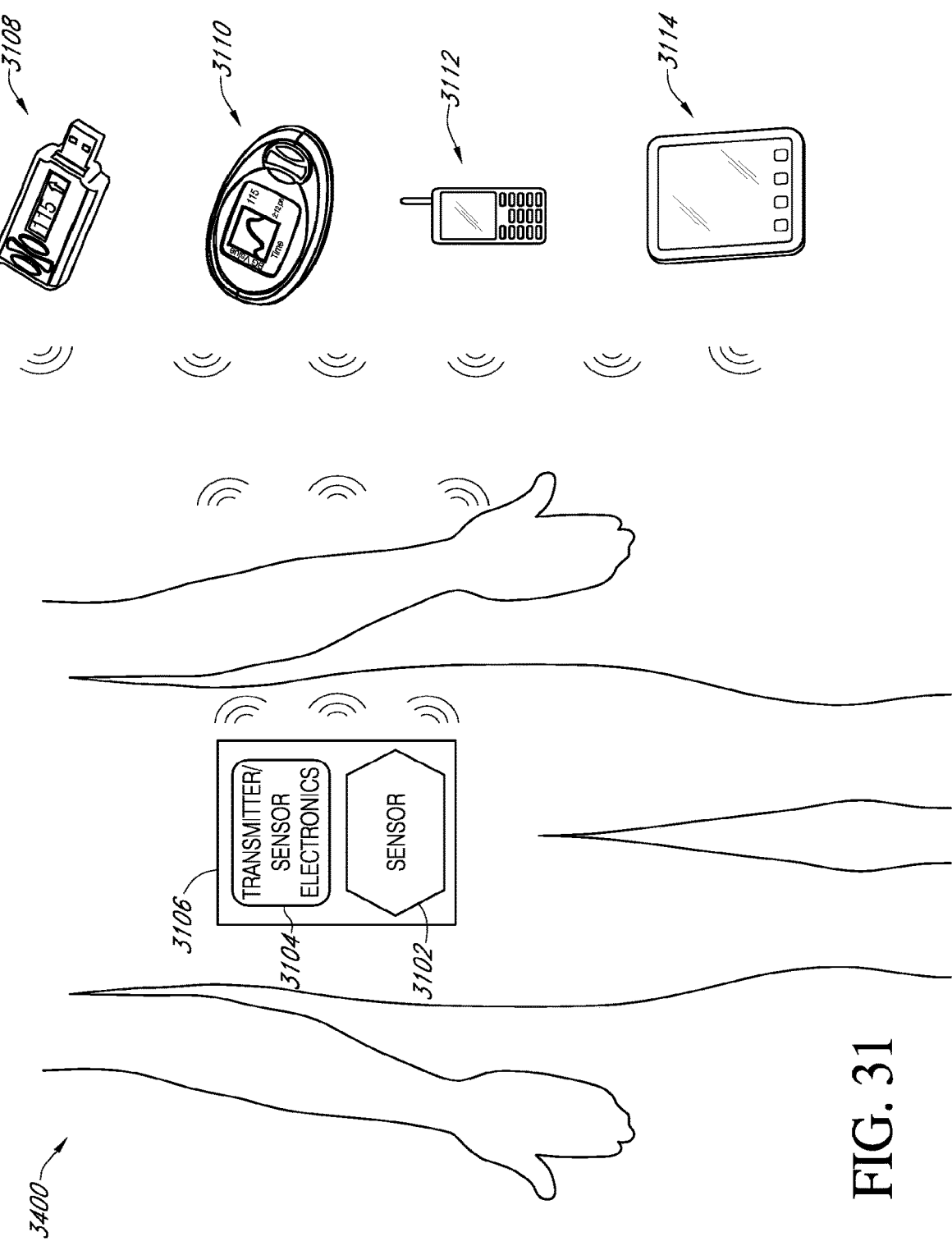
FIG. 31 illustrates a schematic view of a continuous analyte sensor system, according to some embodiments.

U.S. Patent Publication No. US-2013-0267811-A1, the entire contents of which are incorporated by reference herein, explains how FIG. 31 is a schematic of a continuous analyte sensor system 3100 attached to a host (e.g., a person). The analyte sensor system 3100 communicates with other devices 3108-3114 (which can be located remotely from the host). A transcutaneous analyte sensor system 3100 comprising an on-skin sensor assembly 3106 is fastened to the skin of a host via a base (not shown), which can be a disposable housing.

The system 3100 includes a transcutaneous analyte sensor 3102 and an electronics unit (referred to interchangeably as "sensor electronics" or "transmitter") 3104 for wirelessly transmitting analyte information to a receiver. The receiver can be located remotely relative to the system 3100. In some embodiments, the receiver includes a display screen, which can display information to a person such as the host. Example receivers include computers such as dedicated display devices, mobile electronics, smartphones, smart-watches, tablet computers, laptop computers, and desktop computers. In some embodiments, receivers can be Apple Watches, iPhones, and iPads made by Apple Inc. Receivers may be running customized or stock operating systems such as, but not limited to, linux, iOS by Apple Inc., or Android by Google Inc.

In some embodiments, the receiver is mechanically coupled to the electronics unit 3104 to enable the receiver to receive data (e.g., analyte data) from the electronics unit 3104. To increase the convenience to users, in several embodiments, the receiver does not need to be mechanically coupled to the electronics unit 3104 and can even receive data from the electronics unit 3104 over great distances (e.g., when the receiver is many feet or even many miles from the electronics unit 3104).

During use, a sensing portion of the sensor 3102 can be under the host's skin and a contact portion of the sensor 3102 can be electrically connected to the electronics unit 3104. The electronics unit 3104 can be engaged with a housing (e.g., a base) or directly coupled to an adhesive patch fastened to the skin of the host.

The on-skin sensor assembly 3106 may be attached to the host with use of an applicator adapted to provide convenient and secure application. Such an applicator may also be used for attaching the electronics unit 3104 to a base, inserting the sensor 3102 through the host's skin, and/or connecting the sensor 3102 to the electronics unit 3104. Once the electronics unit 3104 is engaged with the base and the sensor 3102 has been inserted into the skin (and is connected to the electronics unit 3104), the sensor assembly can detach from the applicator.

The continuous analyte sensor system 3100 can include a sensor configuration that provides an output signal indicative of a concentration of an analyte. The output signal including (e.g., sensor data, such as a raw data stream, filtered data, smoothed data, and/or otherwise transformed sensor data) is sent to the receiver.

In some embodiments, the analyte sensor system 3100 includes a transcutaneous glucose sensor, such as is described in U.S. Patent Publication No. US-2011-0027127-A1, the entire contents of which are hereby incorporated by reference. In some embodiments, the sensor system 3100 includes a continuous glucose sensor and comprises a transcutaneous sensor (e.g., as described in U.S. Pat. No. 6,565,509, as described in U.S. Pat. No. 6,579,690, as described in U.S. Pat. No. 6,484,046). The contents of U.S. Pat. Nos. 6,565,509, 6,579,690, and 6,484,046 are hereby incorporated by reference in their entirety.

In several embodiments, the sensor system 3100 includes a continuous glucose sensor and comprises a refillable subcutaneous sensor (e.g., as described in U.S. Pat. No. 6,512,939). In some embodiments, the sensor system 3100 includes a continuous glucose sensor and comprises an intravascular sensor (e.g., as described in U.S. Pat. No. 6,477,395, as described in U.S. Pat. No. 6,424,847). The contents of U.S. Pat. Nos. 6,512,939, 6,477,395, and 6,424,847 are hereby incorporated by reference in their entirety.

Various signal processing techniques and glucose monitoring system embodiments suitable for use with the embodiments described herein are described in U.S. Patent Publication No. US-2005-0203360-A1 and U.S. Patent Publication No. US-2009-0192745-A1, the contents of which are hereby incorporated by reference in their entirety. The sensor can extend through a housing, which can maintain the sensor on the skin and can provide for electrical connection of the sensor to sensor electronics, which can be provided in the electronics unit 3104.

One or more repeaters, receivers and/or display devices, such as a key fob repeater 3108, a medical device receiver 3110 (e.g., an insulin delivery device and/or a dedicated glucose sensor receiver), a smartphone 3112, a portable computer 3114, and the like can be communicatively coupled to the electronics unit 3104 (e.g., to receive data from the electronics unit 3104). The electronics unit 3104 can also be referred to as a transmitter. In some embodiments, the devices 3108-3114 transmit data to the electronics unit 3104. The sensor data can be transmitted from the sensor electronics unit 3104 to one or more of the key fob repeater 3108, the medical device receiver 3110, the smartphone 3112, the portable computer 3114, and the like. In some embodiments, analyte values are displayed on a display device.

The electronics unit 3104 may communicate with the devices 3108-3114, and/or any number of additional devices, via any suitable communication protocol. Example communication protocols include radio frequency; Bluetooth; universal serial bus; any of the wireless local area network (WLAN) communication standards, including the IEEE 802.11, 802.15, 802.20, 802.22 and other 802 communication protocols; ZigBee; wireless (e.g., cellular) telecommunication; paging network communication; magnetic induction; satellite data communication; and/or a proprietary communication protocol.

Additional sensor information is described in U.S. Pat. Nos. 7,497,827 and 8,828,201. The entire contents of U.S. Pat. Nos. 7,497,827 and 8,828,201 are incorporated by reference herein.

Any sensor shown or described herein can be an analyte sensor; a glucose sensor; and/or any other suitable sensor. A sensor described in the context of any embodiment can be any sensor described herein or incorporated by reference, such as an analyte sensor; a glucose sensor; any sensor described herein; and any sensor incorporated by reference. Sensors shown or described herein can be configured to sense, measure, detect, and/or interact with any analyte.

As used herein, the term "analyte" is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid, urine, sweat, saliva, etc.) that can be analyzed. Analytes can include naturally occurring substances, artificial substances, metabolites, or reaction products.

In some embodiments, the analyte for measurement by the sensing regions, devices, systems, and methods is glucose. However, other analytes are contemplated as well, including, but not limited to ketone bodies; Acetyl Co A; acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; cortisol; testosterone; choline; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; triglycerides; glycerol; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, *dengue virus, Dracunculus medinensis, Echinococcus granulosus, Entamoeba histolytica, enterovirus, Giardia duodenalisa, Helicobacter pylori,* hepatitis B virus, herpes virus, HIV-1, IgE (atopic disease), influenza virus, *Leishmania donovani, leptospira,* measles/mumps/rubella, *Mycobacterium leprae, Mycoplasma pneumoniae, Myoglobin, Onchocerca volvulus, parainfluenza virus, Plasmodium falciparum, poliovirus, Pseudomonas aeruginosa,* respiratory syncytial virus, *rickettsia (scrub typhus), Schistosoma mansoni, Toxoplasma gondii, Trepenoma pallidium, Trypanosoma cruzi/rangeli,* vesicular stomatis virus, *Wuchereria bancrofti,* yellow fever virus); specific antigens (hepatitis B virus, HIV-1); acetone (e.g., succinylacetone); acetoacetic acid; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin.

Salts, sugar, protein, fat, vitamins, and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin; glucagon; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), 5-hydroxyindoleacetic acid (FHIAA), and intermediaries in the Citric Acid Cycle.

Many embodiments described herein use an adhesive. One purpose of the adhesive can be to couple a base, a sensor module, and/or a sensor to a host (e.g., to skin of the host). The adhesive can be configured for adhering to skin. The adhesive can include a pad (e.g., that is located between the adhesive and the base). Additional adhesive information, including adhesive pad information, is described in U.S. patent application Ser. No. 14/835,603, which was filed on Aug. 25, 2015. The entire contents of U.S. patent application Ser. No. 14/835,603 are incorporated by reference herein.

Sterilization and Sealing of Applicators

Any time a foreign structure comes in contact with the human body there is a potential for infection, which can lead to serious health consequences. Thus, sterilization of an applicator (and/or of the portions of an applicator that come in contact with, or that are inserted into, a body part of the host) are not only desirable, but required in many circumstances. Various sterilization methods can be used in embodiments, including but not limited to heat sterilization, gamma sterilization, electron beam sterilization, and gas (e.g. ethylene oxide) sterilization. In embodiments adapted for gas sterilization, an applicator can be configured with one or more apertures, at least during one or more steps of manufacture, which are configured to allow ingress and egress of gas during one or more sterilization steps. In addition, it may be desirable to seal applicators from ingress of moisture (e.g., water vapor) in some embodiments. Moisture, especially water vapor, can corrode (e.g., rust, tarnish) any metallic parts within an applicator, for example, a needle, a spring, or any other metallic structure. Such corrosion coming in contact with the host, especially where a needle enters the skin of a host, can cause serious health consequences. Moisture can also promote growth of infectious agents and provide a medium for their proliferation, causing serious health consequences. The present application provides various embodiments of applicators that are gas sterilizable and/or include a moisture (e.g., water vapor) seal, for example, through the use of one or more removable caps on the top (e.g., proximal) or bottom (e.g., distal) ends of the applicator, through one or more trigger mechanisms comprising integrated caps, through one or more sealing layers that cover one or more orifices, apertures or vents of the applicator, through sterilizable gas-permeable polymers, through sterilizable gas-permeable trigger mechanisms, through protective cups, or any combinations of the same, as will be described in more detail in connection with at least some of FIGS. 1A-40 below.

Safety Features of Applicators

Consumers may find it desirable to use applicators that provide particular safety features. For example, tamper evident sealing or other tamper evidence features may be desirable because such features allow a consumer to identify when an applicator has been previously used or containment has been breached and, thus, avoid using an applicator that may be faulty or pose an increased health risk if used. Examples of tamper evidence features are described in more detail in connection with at least some of FIGS. 1A-40 below.

In addition, especially in the case of disposable applicators, it can be frustrating or dangerous to have an applicator deploy prematurely or unexpectedly. Thus, consumers may find it desirable for applicators to include premature deployment prevention features to substantially reduce or prevent the occurrence of premature activation. Examples of premature deployment prevention features are described in more detail in connection with at least some of FIGS. 1A-40 below.

In line with premature deployment prevention features, it may be desirable to provide features which minimize the risk of unintended activation when the applicator is dropped. For example, an exposed trigger mechanism may be accidentally activated if the applicator is dropped on the exposed trigger mechanism. However, in some cases, the shock of dropping the applicator itself can cause accidental activation of the applicator even where there is no exposed trigger mechanism. Examples of drop protection features and other premature deployment prevention features are described in more detail in connection with at least some of FIGS. 1A-40 below.

Bulk Manufacturing and/or Sterilization

The cost of manufacture of applicators is a concern for the manufacturer as well as for the consumer. In general, the less expensive it is to produce an applicator, the lower the cost it is to the consumer. Thus, it is desirable to provide bulk manufacturing, sterilizing and/or sealing of applicators. Examples of applicator configurations and methods of bulk sterilizing and/or sealing of applicators include, but are not limited to, melting, chemically altering, or physically altering a vent, plug, feature, or layer such that it transforms from a state of being permeable to a sterilizing gas and/or moisture (e.g., water vapor) to impermeable to the sterilizing gas and/or moisture, as will be described in more detail in connection with at least some of FIGS. 1A-40 below.

Easy and Repositionable Deployment

Consumers may additionally find it desirable to easily position (and reposition if desired) an applicator in a particular location on the body, optionally using only a single hand, without necessarily requiring a complete view of the applicator as it is held in the desired location. Such easy single-handed deployment may be achieved through the provision of various orientations and forms of actuation members, as well as the use of one or more raised or recessed portions configured as tactile grips and/or orientation indicators, as will be described in more detail in connection with at least some of FIGS. 1A-40 below. Consumers may also find it desirable to be able to reposition the applicator prior to activation even after it has been first placed on the body, without comprising the integrity of the applicator and/or any adhesive provided thereon.

Embodiments Including a Removable Cap

Figures 1A, 1B, 1C:
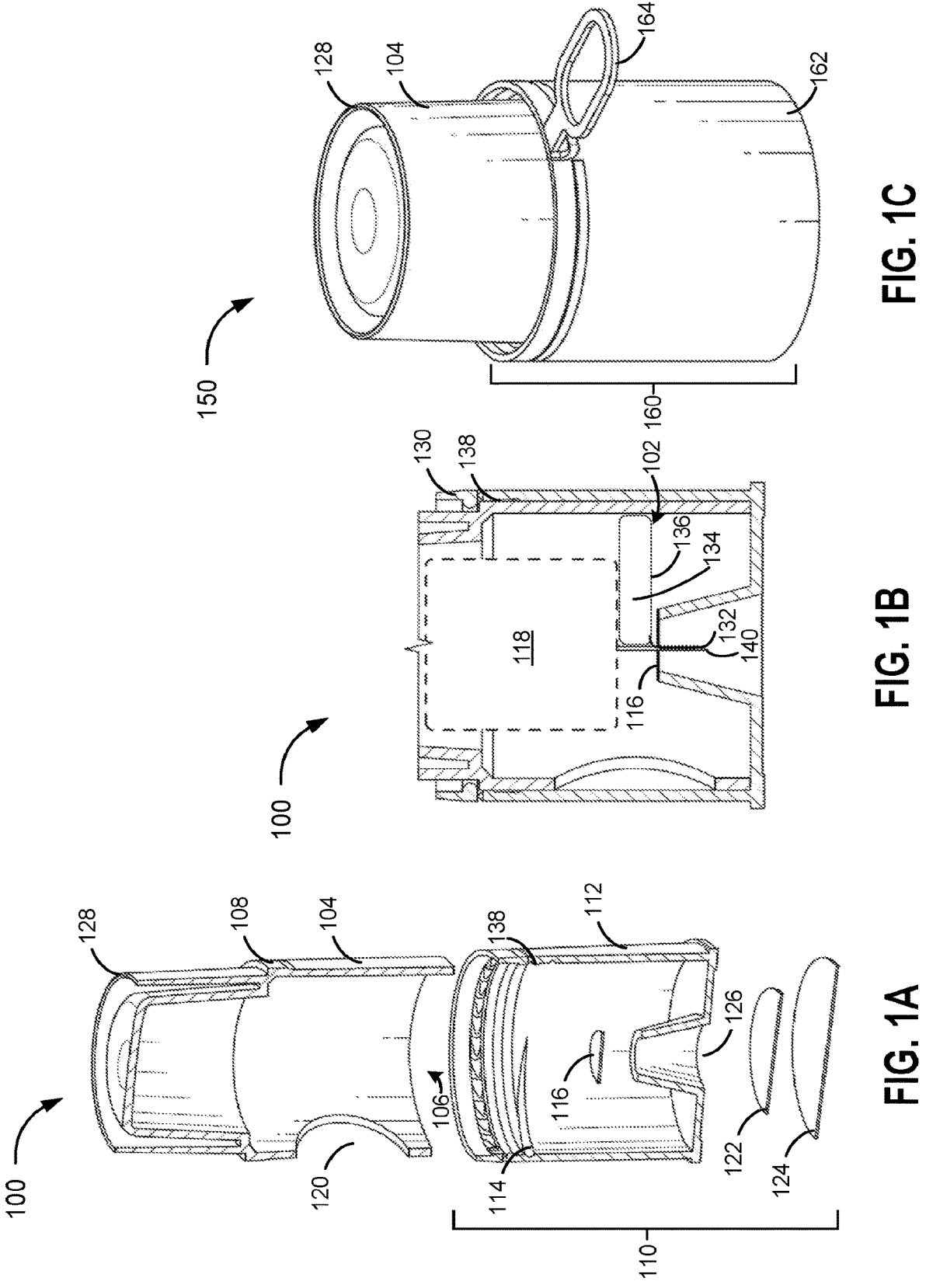
FIG. 1A is an exploded cross-sectional view of an applicator for applying an on-skin assembly to skin of a host including a sealing element, in accordance with some embodiments.
FIG. 1B is a zoomed cutaway view of the applicator of FIG. 1A, further illustrating an insertion assembly and the on-skin assembly, in accordance with some embodiments.
FIG. 1C illustrates a perspective view of an applicator for applying an on-skin assembly to skin of a host including a sealing element having a frangible member, in accordance with some embodiments.

Some embodiments can include a removable cap configured to function as a sterilization seal and/or as a moisture barrier. For example, FIG. 1A is an exploded, cutaway view of an applicator 100 for applying an on-skin assembly 102 to skin of a host including a sealing element 110, in accordance with some embodiments. Applicator 100 comprises a housing 104 configured to house an insertion assembly 118 (see FIG. 1B). Housing 104 comprises an aperture 106 through which on-skin assembly 102 (see FIG. 1B) is configured to pass during deployment. The side of housing 104 may further comprise an opening 120 configured to receive an actuation member (not shown in FIGS. 1A-1C). Such an actuation member can be configured to, upon activation, cause insertion assembly 118 to insert at least a portion of on-skin assembly 102 into the skin of a host. The actuation member is disposed on a side of housing 104 in the region of the opening 120. By providing an actuation member on a side of housing 104, applicator 100 may provide for easy single-handed deployment of on-skin assembly 102 to the skin of a host.

Housing 104 further comprises an optional flexible wall 128 configured to absorb at least a portion of energy imparted to applicator 100 when applicator 100 is dropped. By absorbing energy that might otherwise transfer a physical shock to applicator 100, flexible wall 128 may provide a premature deployment prevention and drop protection feature.

Applicator 100 further comprises a sealing element 110 configured to provide a sterile barrier and/or a vapor barrier between an internal environment of housing 104 and an external environment of housing 104. As shown in FIG. 1A, sealing element 110 comprises a removable cap 112 configured to couple with a portion of housing 104. Specifically, and as an example, removable cap 112 is configured to couple with a distal portion of housing 104 via threads 114. For example, threads 114 disposed on removable cap 112 may be configured to mate with threads 108 disposed on housing 104. Removable cap 112 may be detached from housing 104 by twisting removable cap 112 with respect to housing 104, or vice versa, until threads 114 and threads 108 are no longer mated with each other, and then pulling housing 104 and removable cap 112 apart. Sealing element 110 may additionally comprise retention element 138 between removable cap 112 and housing 104 before removal of removable cap 112. As shown, removable cap 112 covers the actuation member by virtue of the actuation member being disposed on a side of housing 104. Sealing element 110 may further comprise a first layer 122 that is permeable to a sterilizing gas (e.g., ethylene oxide, or ETO). First layer 122 may comprise Tyvek® material, although any other material permeable to a sterilizing gas may be utilized. Application of first layer 122 to removable cap 112 may allow for the ingress and egress of a sterilizing gas during manufacture. Sealing element 110 may further comprise a second layer 124 that is substantially impermeable to moisture (e.g., water vapor). Second layer 124 may comprise a metallic foil, although any suitable material impermeable to moisture (e.g., water vapor) may be utilized, for example, a metallic foil (e.g., aluminum or titanium), a metallic substrate, an aluminum oxide coated polymer, parylene, a polymer coated with a metal applied via vapor metallization, a silicon dioxide coated polymer, or any material having a moisture vapor transmission rate less than 10 grams/100 in$^2$ or preferably less than 1 gram/100 in$^2$. First layer 122 and second layer 124 may seal an opening 126 in the bottom of removable cap 112. Application of second layer 124 over first layer 122 after sterilization may further maintain sterility via the first layer and add a moisture barrier via the second layer. Together, the above-described features of sealing element 110 may provide joint sterilization and moisture sealing of applicator 100.

The applicator 100 further includes a support member 116 configured to inhibit at least lateral movement of insertion assembly 118. In some embodiments, support member 116 may comprise an elastomeric membrane, film, bulk elastomer, foam, or rigid structure. Furthermore, support member 116 can maintain the insertion assembly 118 in position during deleterious movement such as a drop or vibration.

FIG. 1B is a zoomed cutaway view of applicator 100 of FIG. 1A, further illustrating at least insertion assembly 118 and on-skin assembly 102, in accordance with some embodiments. As shown in more detail in FIG. 1B, insertion assembly 118 may comprise a needle 140, for example, a C-needle configured to hold at least a portion of a sensor. In some embodiments, insertion assembly 118 may be configured to drive needle 140 utilizing a spring force. In some embodiments, insertion assembly 118 may additionally or alternatively be configured to retract needle 140 after on-skin assembly 102 has been deployed to the skin of the host.

Figure 7A:
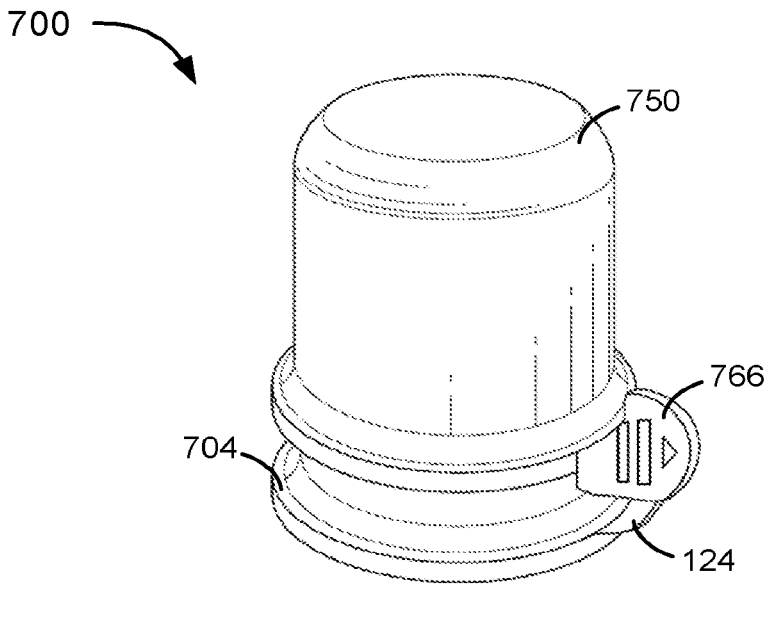
FIG. 7A illustrates a perspective view of an applicator for applying an on-skin assembly to skin of a host including a frangible member configured to prevent activation of an actuation member, in accordance with some embodiments.
Figure 7B:
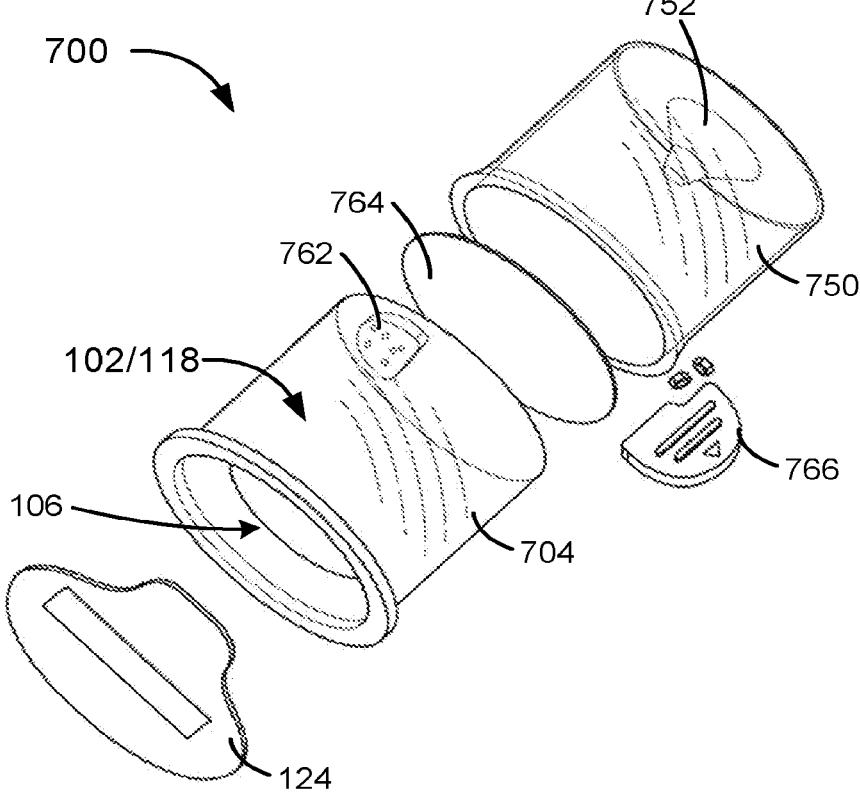
FIG. 7B is a partially exploded view of the applicator of FIG. 7A.
Figures 8A, 8B, 8C:
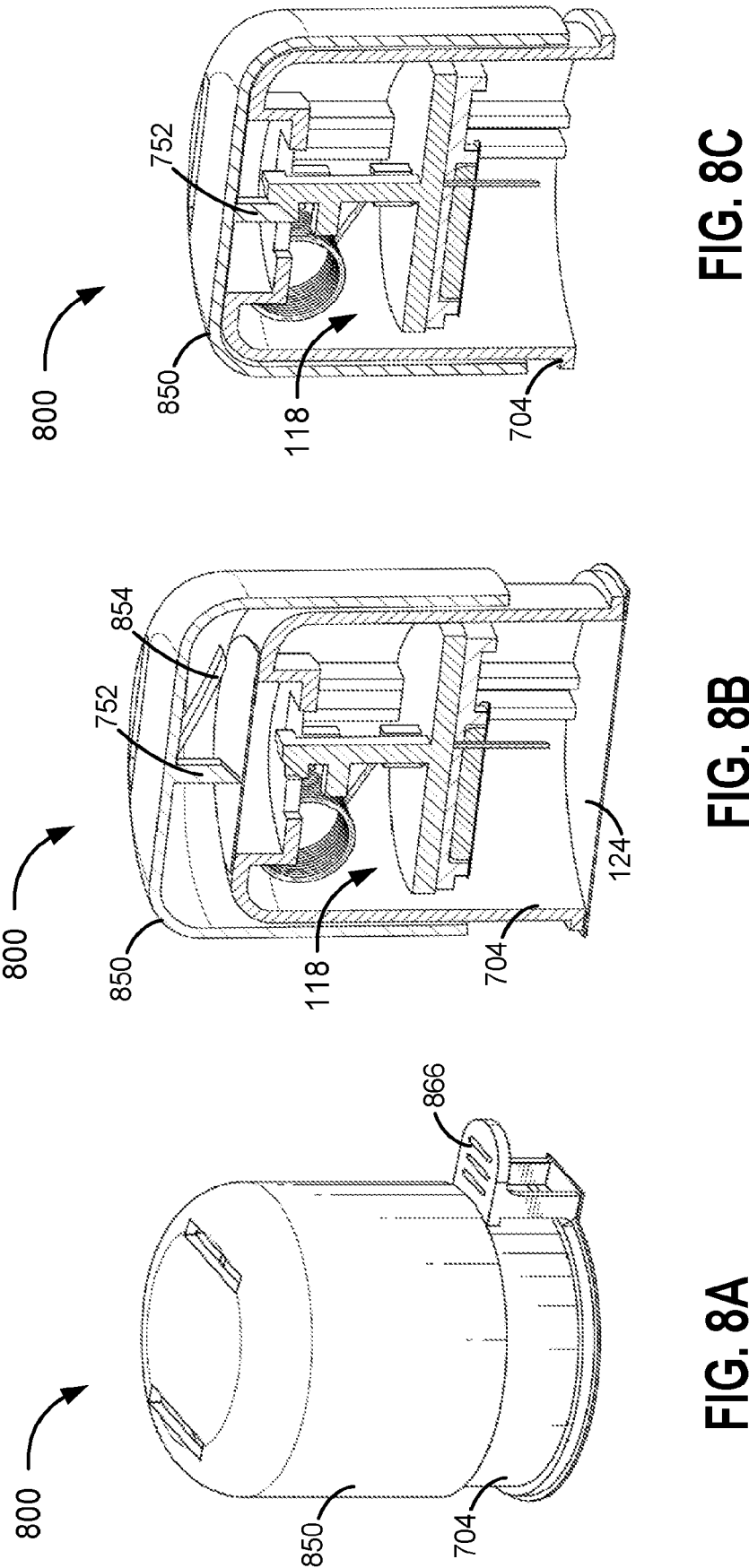
FIG. 8A illustrates a perspective view of another applicator for applying an on-skin assembly to skin of a host including a frangible member configured to prevent activation of an actuation member, in accordance with some embodiments.
FIG. 8B is a cross-sectional view of the applicator of FIG. 8A in a pre-deployment configuration.
FIG. 8C is a cross-sectional view of the applicator of FIG. 8A in a deployed configuration.

In some embodiments, insertion assembly 118 may include substantially similar components and/or mechanisms from insertion assembly 118 of FIG. 8A-8C. In other embodiments, insertion assembly 118 may include substantially similar components from insertion assemblies described in U.S. patent application Ser. No. 15/387,088, which is incorporated herein by reference it its entirety. For non-limiting example, insertion assembly 118 may include substantially similar components and/or mechanisms from telescoping assembly 132 of FIGS. 7-11, telescoping assembly 132b of FIGS. 56-58, telescoping assembly 132c and 132d of FIGS. 28-30, telescoping assembly 132e of FIG. 31, telescoping assembly 132f of FIG. 59, telescoping assembly 132g of FIGS. 44-45, telescoping assembly 132h of FIG. 60, telescoping assembly 132i of FIG. 48-50, telescoping assembly 132k of FIGS. 61-64, telescoping assembly 132m of FIGS. 71-74, telescoping assembly 132n of FIGS. 76-79, telescoping assembly 132p of FIGS. 80-85, telescoping assembly 132q of FIGS. 86-88, telescoping assembly 132r of FIGS. 89-91, telescoping assembly 132s of FIGS. 92-100, or telescoping assembly 132w of FIGS. 110-119, respectively described in U.S. patent application Ser. No. 15/387, 088.

Applicator 100 further comprises a transcutaneous on-skin analyte sensor assembly (referred to as an "on-skin assembly") 102 and an electronics unit (referred to as a "transmitter") 134 for wirelessly transmitting analyte information to a receiver (not shown). Before deployment, a sensor 132 of on-skin assembly 102 may be disposed on or at least partially in needle 140. During use, sensor 132 is disposed under the host's skin and a contact portion of on-skin assembly 102 is electrically connected to transmitter 134. On-skin assembly 102 is attached to an adhesive layer 136 for fastening to the skin of the host.

On-skin assembly 102 may be attached to the host with use of applicator 100 adapted to provide convenient and secure application. Applicator 100 may also be used for inserting at least a portion of on-skin assembly 102 through the host's skin. Once the portion of on-skin assembly 102 has been inserted, applicator 100 detaches from on-skin assembly 102.

In general, on-skin assembly 102 includes any sensor configuration that provides an output signal indicative of a concentration of an analyte, for example, blood glucose. The output signal including, e.g., sensor data, such as a raw data stream, filtered data, smoothed data, and/or otherwise transformed sensor data, is sent to a receiver which may be e.g., a smart phone, smart watch, dedicated device and the like. In some embodiments, sensor 132 comprises a transcutaneous glucose sensor, such as is described in US Patent Publication No. US-2011-0027127-A1, the contents of which are hereby incorporated by reference in its entirety. In some embodiments, sensor 132 is a continuous glucose sensor and comprises a transcutaneous sensor such as described in U.S. Pat. No. 6,565,509 to Say et al., for example. In another embodiment, sensor 132 is a continuous glucose sensor and comprises a subcutaneous sensor such as described with reference to U.S. Pat. No. 6,579,690 to Bonnecaze et al. or U.S. Pat. No. 6,484,046 to Say et al., for example. In some other embodiments, sensor 132 is a continuous glucose sensor and comprises a subcutaneous sensor such as described with reference to U.S. Pat. No. 6,512,939 to Colvin et al. In yet other embodiments, sensor 132 is a continuous glucose sensor and comprises an intravascular sensor such as described with reference to U.S. Pat. No. 6,477,395 to Schulman et al., for example. In yet other embodiments, sensor 132 is a continuous glucose sensor and comprises an intravascular sensor such as described with reference to U.S. Pat. No. 6,424,847 to Mastrototaro et al. Other signal processing techniques and glucose monitoring system embodiments suitable for use with the embodiments described herein are described in U.S. Patent Publication No. US-2005-0203360-A1 and U.S. Patent Publication No. US-2009-0192745-A1, the contents of which are hereby incorporated by reference in their entireties.

In still further embodiments, applicator 100 can be configured for use in applying a drug delivery device, such an infusion device, to the skin of a patient. In such embodiments, applicator 100 can include a catheter instead of, or in addition to, a sensor, the catheter being connected to an infusion pump configured to deliver liquid medicines or other fluids into the patient's body. In embodiments, the catheter can be deployed into the skin in much the same manner as a sensor would be, for example as described herein.

In some embodiments, sensor 132 is formed from a wire or is in a form of a wire. For example, sensor 132 can include an elongated conductive body, such as a bare elongated conductive core (e.g., a metal wire) or an elongated conductive core coated with one, two, three, four, five, or more layers of material, each of which may or may not be conductive. The elongated sensor may be long and thin, yet flexible and strong. For example, in some embodiments, the smallest dimension of the elongated conductive body is less than about 0.1 inches, less than about 0.075 inches, less than about 0.05 inches, less than about 0.025 inches, less than about 0.01 inches, less than about 0.004 inches, or less than about 0.002 inches. Sensor 132 may have a circular cross-section. In some embodiments, the cross-section of the elongated conductive body can be ovoid, rectangular, triangular, polyhedral, star-shaped, C-shaped, T-shaped, X-shaped, Y-Shaped, irregular, or the like. In some embodiments, a conductive wire electrode is employed as a core. To such a clad electrode, one or two additional conducting layers may be added (e.g., with intervening insulating layers provided for electrical isolation). The conductive layers can be comprised of any suitable material. In certain embodiments, it can be desirable to employ a conductive layer comprising conductive particles (i.e., particles of a conductive material) in a polymer or other binder.

In certain embodiments, the materials used to form the elongated conductive body (e.g., stainless steel, titanium, tantalum, platinum, platinum-iridium, iridium, certain polymers, and/or the like) can be strong and hard, and therefore are resistant to breakage. For example, in some embodiments, the ultimate tensile strength of the elongated conductive body is from about 80 kPsi to about 500 kPsi. In another example, in some embodiments, the Young's modulus of the elongated conductive body is from about 160 GPa to about 220 GPa. In still another example, in some embodiments, the yield strength of the elongated conductive body is from about 60 kPsi to about 2200 kPsi. In some embodiments, sensor's 132 small diameter provides (e.g., imparts, enables) flexibility to these materials, and therefore to sensor 132 as a whole. Thus, sensor 132 can withstand repeated forces applied to it by surrounding tissue.

In addition to providing structural support, resiliency and flexibility, in some embodiments, the core (or a component thereof) provides electrical conduction for an electrical signal from the working electrode to sensor electronics (not shown). In some embodiments, the core comprises a conductive material, such as stainless steel, titanium, tantalum, a conductive polymer, and/or the like. However, in other embodiments, the core is formed from a non-conductive material, such as a non-conductive polymer. In yet other embodiments, the core comprises a plurality of layers of materials. For example, in some embodiments the core includes an inner core and an outer core. In a further embodiment, the inner core is formed of a first conductive material and the outer core is formed of a second conductive material. For example, in some embodiments, the first conductive material is stainless steel, titanium, tantalum, a conductive polymer, an alloy, and/or the like, and the second conductive material is conductive material selected to provide electrical conduction between the core and the first layer, and/or to attach the first layer to the core (e.g., if the first layer is formed of a material that does not attach well to the core material). In another embodiment, the core is formed of a non-conductive material (e.g., a non-conductive metal and/or a non-conductive polymer) and the first layer is a conductive material, such as stainless steel, titanium, tantalum, a conductive polymer, and/or the like. The core and the first layer can be of a single (or same) material, e.g., platinum. One skilled in the art appreciates that additional configurations are possible.

In some embodiments, transmitter 134 is incorporated into on-skin assembly 102, while in other embodiments, the transmitter 134 can be releasably coupled to the sensor. Transmitter 134 includes electronic circuitry associated with measuring and processing the continuous analyte sensor data, and is configured to perform algorithms associated with processing and calibration of the sensor data. For example, transmitter 134 can provide various aspects of the functionality of a sensor electronics module as described in U.S. Patent Publication No. 2009-0240120-A1 and U.S. Patent Publication No. 2012-0078071-A1 the contents of which are hereby incorporated by reference in their entireties. Transmitter 134 may include hardware, firmware, and/or software that enable measurement of levels of the analyte via a glucose sensor, such as an analyte on-skin assembly 102. For example, transmitter 134 can include a potentiostat, a power source for providing power to on-skin assembly 102, other components useful for signal processing and data storage, and preferably a telemetry module for one- or two-way data communication between transmitter 134 and one or more receivers, repeaters, and/or display devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. Transmitter 134 may include sensor electronics that are configured to process sensor information, such as storing data, analyzing data streams, calibrating analyte sensor data, estimating analyte values, comparing estimated analyte values with time corresponding measured analyte values, analyzing a variation of estimated analyte values, and the like. Examples of systems and methods for processing sensor analyte data are described in more detail herein and in U.S. Pat. Nos. 7,310,544, 6,931,327, U.S. Patent Publication No. 2005-0043598-A1, U.S. Patent Publication No. 2007-0032706-A1, U.S. Patent Publication No. 2007-0016381-A1, U.S. Patent Publication No. 2008-0033254-A1, U.S. Patent Publication No. 2005-0203360-A1, U.S. Patent Publication No. 2005-0154271-A1, U.S. Patent Publication No. 2005-0192557-A1, U.S. Patent Publication No. 2006-0222566-A1, U.S. Patent Publication No. 2007-0203966-A1 and U.S.

Patent Publication No. 2007-0208245-A1, the contents of which are hereby incorporated by reference in their entireties.

One or more repeaters, receivers and/or display devices, such as a medical device receiver (e.g., insulin delivery device and/or dedicated glucose sensor receiver), smart phone, portable computer, and the like may be operatively linked to and receive data from transmitter 134, and in some embodiments transmit data to transmitter 134.

In some embodiments, analyte values are displayed on a display device. In some embodiments, prompts or messages can be displayed on the display device to convey information to the user, such as reference outlier values, requests for reference analyte values, therapy recommendations, deviation of the measured analyte values from the estimated analyte values, or the like. Additionally, prompts can be displayed to guide the user through calibration or troubleshooting of the calibration.

Although not necessarily shown in other FIGS., any applicator described in this specification may include insertion assembly 118 and on-skin assembly 102 as described in connection with FIGS. 1A and 1B.

Applicator 100 may further comprise a tamper indicator 130, specifically, a tamper-evident ring configured to break away from removable cap 112 when removable cap 112 is twisted with respect to housing 104. In this way, tamper indicator 130 may provide a safety feature for a host using applicator 100 such that if the tamper-evident ring is broken, tampering would be visually evident to a user.

FIG. 1C illustrates another applicator 150 for applying on-skin assembly 102 to skin of a host including a sealing element 160 having a frangible member 164, in accordance with some other embodiments. Applicator 150 may comprise all features previously described in connection with applicator 100 of FIGS. 1A and 1B except, instead of utilizing threads 114 and 108, sealing element 160 comprises a removable cap 162 configured to couple with a distal portion of housing 104 via frangible member 164. In some embodiments, frangible member 164 comprises a loop and a circumferential frangible portion configured to be removed by pulling on the loop. In this way, sealing element 160, including removable cap 162 and frangible member 164, may maintain sterilization and simultaneously provide a moisture seal for elements within housing 104. Frangible member 164 may prevent sealing cap 162 from being removed without also removing frangible member 164. Frangible member 164 further provides a tamper indicator and safety feature for a host using applicator 150 such that if the frangible member 164 is broken, tampering would be visually evident to a user.

Figure 2A:
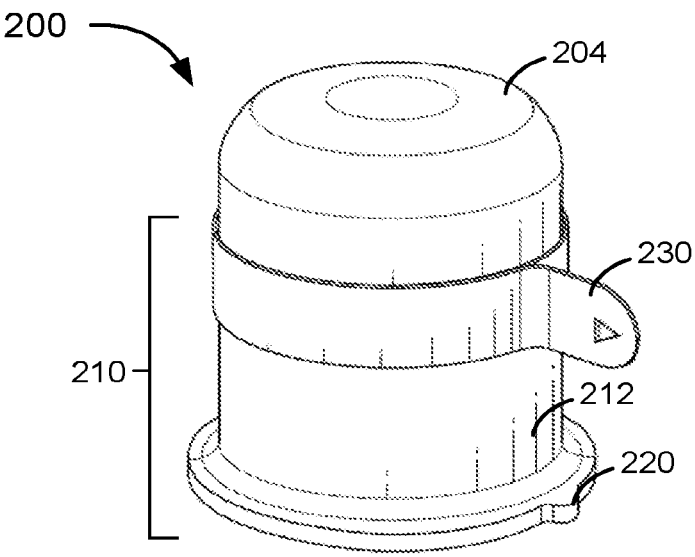
FIG. 2A illustrates a perspective view of an applicator for applying an on-skin assembly to skin of a host including a peelable tamper indicator, in accordance with some embodiments.

FIG. 2A illustrates a perspective view of an applicator 200 for applying on-skin assembly 102 to skin of a host including a peelable tamper indicator 230, in accordance with some embodiments. Applicator 200 may comprise all features previously described in connection with applicator 100 of FIGS. 1A and 1B except those specifically indicated as not being present below. For example, although not shown, applicator 200 may further include at least insertion assembly 118 and on-skin assembly 102 as described in connection with FIGS. 1A-1C.

Applicator 200 comprises a housing 204, a sealing element 210 comprising a removable cap 212, and peelable tamper indicator 230. Housing 204 may not include flexible wall 128 or threads 108 as previously described in connection with FIGS. 1A and 1B Likewise, removable cap 212 may not include threads 114. However, removable cap 212 may comprise at least one protrusion 220 or flattened (e.g., substantially planar) section configured to inhibit rolling of applicator 200 and to provide an orientation indicator for the user. Removable cap 212 may be detached from housing 204 by peeling off peelable tamper indicator 230 and pulling apart removable cap 212 and housing 204. Thus, if peelable tamper indicator 230 has been disturbed, tampering would be visually evident to a user.

Figure 2B:
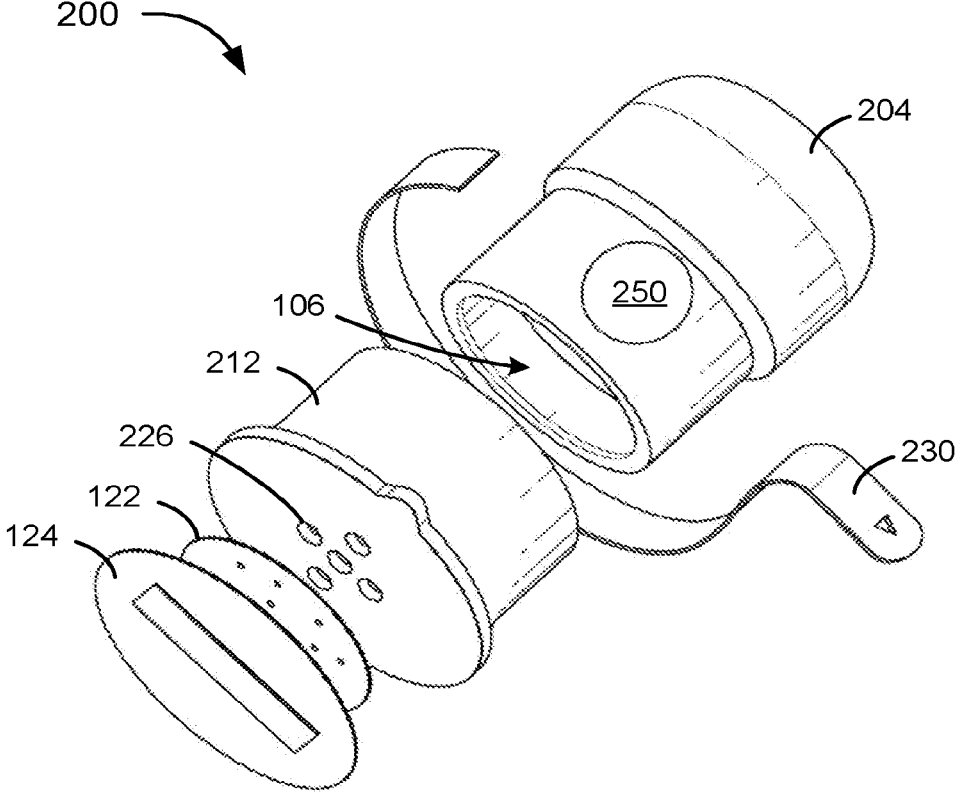
FIG. 2B is a partially exploded perspective view of the applicator of FIG. 2A.

FIG. 2B is a partially exploded view of applicator 200 of FIG. 2A. As shown more clearly in FIG. 2B, applicator 200 may further comprise an actuation member 250 (e.g., a push button) configured to, upon activation, cause insertion assembly 118 (see FIG. 1B) to insert at least a portion of on-skin assembly 102 (see FIG. 1B) into the skin of a host through aperture 106. Similar to FIGS. 1A-1C, removable cap 212 covers actuation member 250 by virtue of actuation member 250 being disposed on a side of housing 204 and removable cap 212 covering a distal portion of housing 204 which shrouds actuation member 250. Shrouding actuation member 250 in this manner may prevent accidental activation. Sealing element 210 may further comprise first layer 122 and second layer 124, as previously described in connection with FIG. 1B. First layer 222 and second layer 224 may be disposed over one or more openings 226 in the bottom of removable cap 212. In some embodiments, the one or more openings 226 facilitate in sterilization and/or venting of the applicator 200. The above-described features of sealing element 210 may provide joint sterilization and moisture sealing for applicator 200.

Figure 3C:
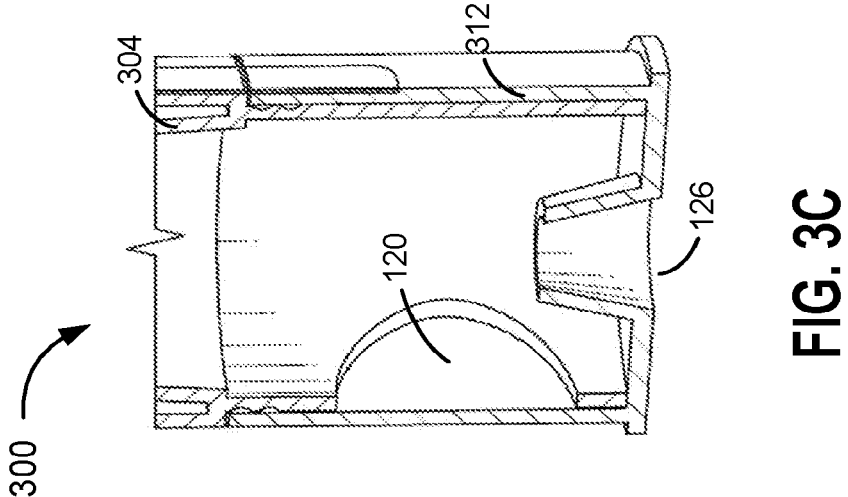
FIG. 3C is zoomed cross-sectional view of the applicator of FIGS. 3A and 3B, in accordance with some embodiments.
Figure 3B:
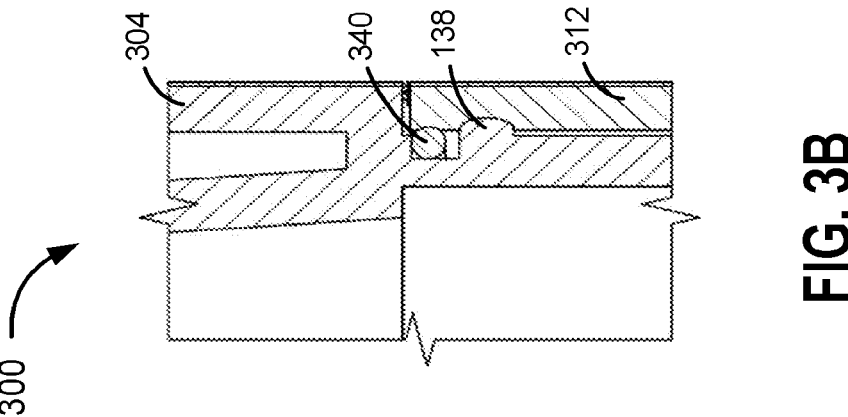
FIG. 3B is a zoomed cross-sectional view of the applicator of FIG. 3A, wherein a sealing element comprises an o-ring, in accordance with some embodiments.
Figure 3A:
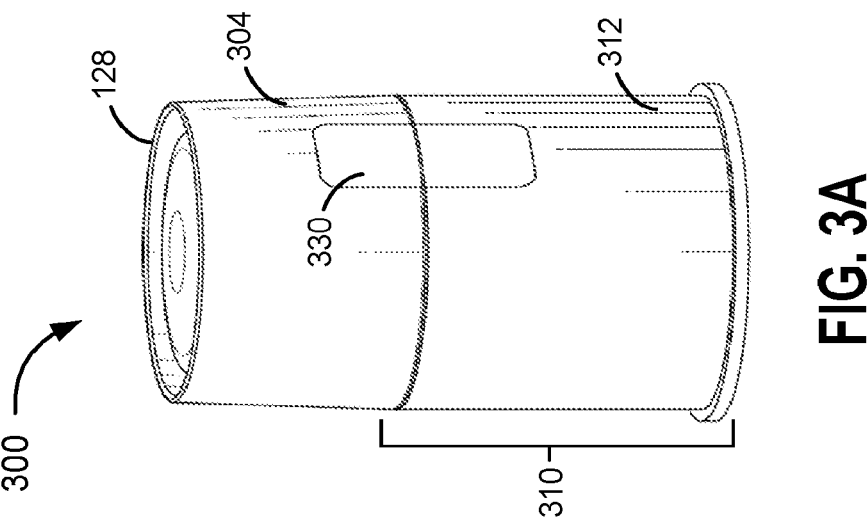
FIG. 3A illustrates a perspective view of an applicator for applying an on-skin assembly to skin of a host including another tamper indicator, in accordance with some embodiments.

FIG. 3A illustrates a perspective view of an applicator 300 for applying on-skin assembly 102 to skin of a host including a perforated tamper indicator tab 330, in accordance with some embodiments. Applicator 300 may comprise all features previously described in connection with applicator 100 of FIGS. 1A and 1B except those specifically indicated as not being present below. For example, although not shown, applicator 300 may further include at least insertion assembly 118 and on-skin assembly 102 as described in connection with FIGS. 1A-1C.

Applicator 300 comprises a housing 304, a sealing element 310 comprising at least a removable cap 312, and adhesive mounted tamper indicator tab 330. Tamper indicator tab 330 may be adhesively backed paper, polymer, or other compatible film material. The tamper indicator tab 330 may further contain perforations, scoring, or deformed sections to guide removal of the tamper indicator tab 330. Housing 304 is further shown to include optional flexible wall 128 but may not include threads 108 as previously described in connection with FIGS. 1A and 1B. Likewise, removable cap 312 may not include threads 114. Removable cap 312 may be detached from housing 304 by twisting and pulling apart removable cap 312 and housing 304. Any tampering with applicator 300 may result in the breaking of tamper indicator tab 330, providing visual evidence of tampering to a user.

FIG. 3B is a zoomed cutaway view of applicator 300 of FIG. 3A, in accordance with some embodiments. As shown, removable cap 312 and/or housing 304 may comprise retention element 138 as previously described in connection with FIGS. 1A and 1B. Sealing element 310 may further comprise an O-ring 340 configured to provide a seal between removable cap 312 and housing 304. In some embodiments, O-ring 340 may be integrally molded together with either cap 312 or housing 304.

FIG. 3C is another zoomed cutaway view of applicator 300 of FIGS. 3A and 3B, in accordance with some embodiments. As shown, the side of housing 304 may further comprise opening 120 configured to receive an actuation member (not shown in FIGS. 3A-3C), as previously described in connection with FIGS. 1A and 1B. By providing an actuation member on a side of housing 304, applicator 300 may provide for easy single-handed deployment of on-skin assembly 102 (not shown in FIG. 3C) to the skin of a host.

FIG. 3C further illustrates opening 126 in the bottom of removable cap 312, as previously described in connection with FIGS. 1A and 1B. Although not shown, sealing element 310 may further comprise first layer 122 and second layer 124 covering opening 126, as previously described in connection with FIGS. 1A and 1B. Together, the above-described features of sealing element 310 may provide joint sterilization and moisture sealing of applicator 100.

Figure 4A:
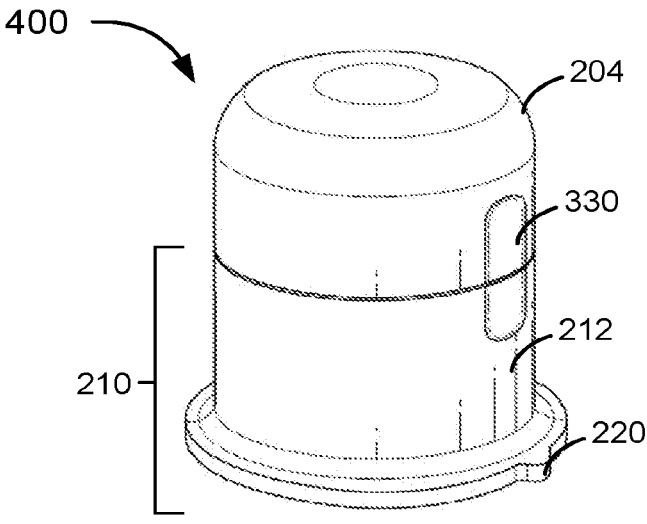
FIG. 4A illustrates a perspective view of another applicator for applying an on-skin assembly to skin of a host including a tamper indicator, in accordance with some embodiments.
Figure 4B:
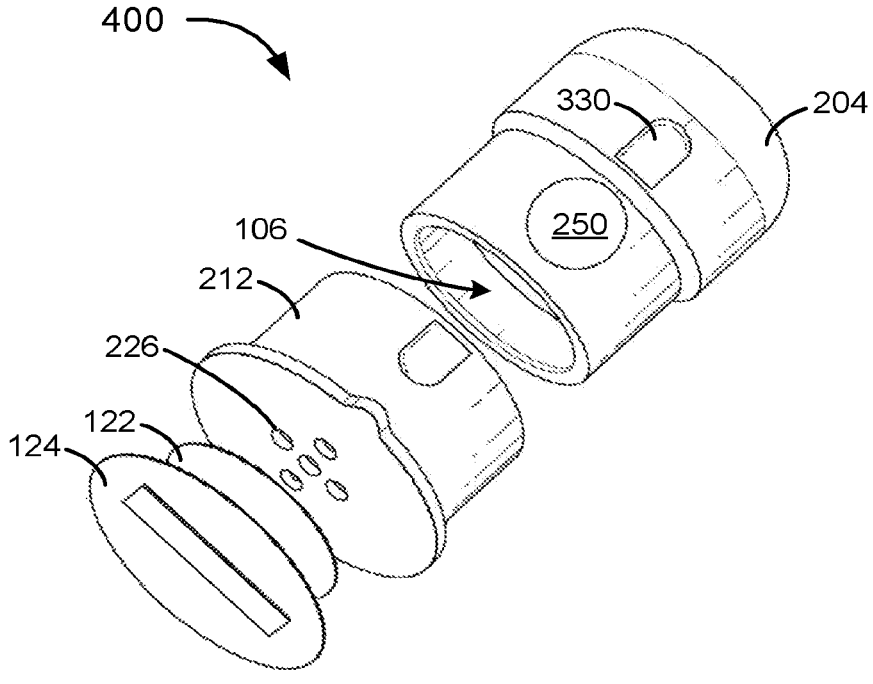
FIG. 4B is a partially exploded view of the applicator of FIG. 4A.

FIG. 4A illustrates another applicator 400 for applying on-skin assembly 102 to skin of a host including a tamper indicator tab 330, in accordance with some embodiments. FIG. 4B is a partially exploded view of applicator 400 of FIG. 4A. Applicator 400 comprises substantially similar features of applicator 200 of FIGS. 2A and 2B, however, replacing peelable tamper indicator 230 with tamper indicator tab 330 of FIGS. 3A-3C. As shown in FIG. 4B, applicator 400 may comprise the one or more openings 226 in the bottom of removable cap 212, as previously described in connection with at least FIG. 2B. First layer 122 and second layer 124 may cover the one or more openings 226.

Figure 5A:
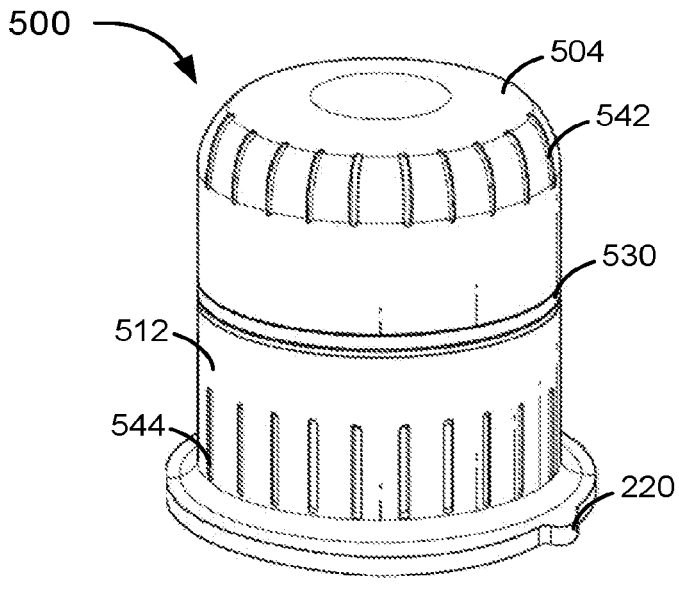
FIG. 5A illustrates a perspective view of an applicator for applying an on-skin assembly to skin of a host including a tactile indication of grip for the host, in accordance with some embodiments.
Figure 5B:
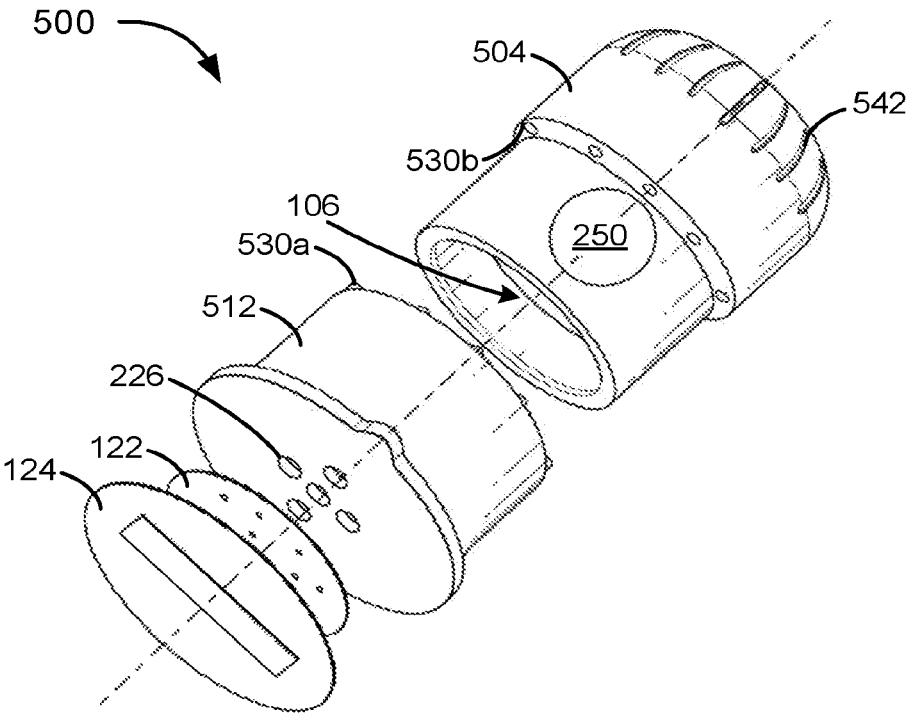
FIG. 5B is a partially exploded view of the applicator of FIG. 5A.

FIG. 5A illustrates another applicator 500 for applying on-skin assembly 102 to skin of a host including a tactile indication of grip for the host, in accordance with some embodiments. FIG. 5B is a partially exploded view of applicator 500 of FIG. 5A. Applicator 500 comprises substantially all features of applicator 200 of FIGS. 2A and 2B, however, replacing peelable tamper indicator 230 with a tamper-evident twist-off collar 530 and further including at least one set of one or more ridges or recesses 542, 544 configured to provide a tactile indication of grip to the host. For example, FIGS. 5A and 5B show a housing 504, which may be substantially the same as housing 204 of FIGS. 2A and 2B, however, further including a first set of one or more ridges or recesses 542 configured to provide a tactile indication of grip to the host. FIGS. 5A and 5B further show a removable cap 512, which may be substantially the same as removable cap 212, however, further including a second set of one or more ridges or recesses 544 configured to provide a tactile indication of grip to the host. As shown in FIG. 5BB, applicator 500 may comprise the one or more openings 226 in the bottom of removable cap 212, as previously described in connection with at least FIG. 2B. First layer 122 and second layer 124 may cover the one or more openings 226.

In addition, tamper-evident twist-off collar 530 is disposed at a mating location between housing 504 and removable cap 512. In some embodiments, a first portion 530a of tamper-evident twist-off collar 530 may be coupled to removable cap 512 and a second portion 530b of tamper-evident twist-off collar 530 may be coupled to housing 504. Removable cap 512 may be detached from housing 504 by twisting removable cap 512 with respect to housing 504, or vice versa, until first portion 530a breaks free of second portion 530b, and then pulling removable cap 512 and housing 504 apart. In its integral state, tamper-evident twist-off collar 530 may provide a seal (e.g., a sterile barrier and a moisture or water vapor barrier) between housing 504 and removable cap 512. In its separated state, tamper-evident twist-off collar 530 may provide an indication of tampering to a user.

US 12,642,456 B2

23

Figure 6A:
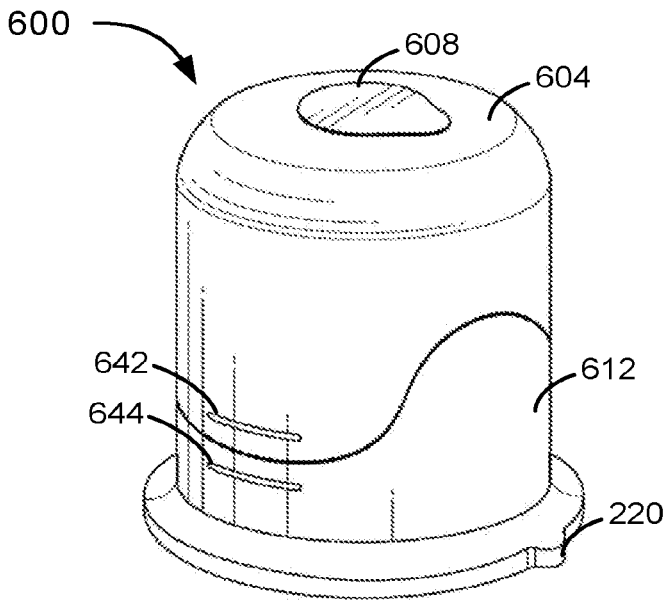
FIG. 6A illustrates a perspective view of an applicator for applying an on-skin assembly to skin of a host including a sealing element configured to couple with a housing in a single axial orientation, in accordance with some embodiments.
Figure 6B:
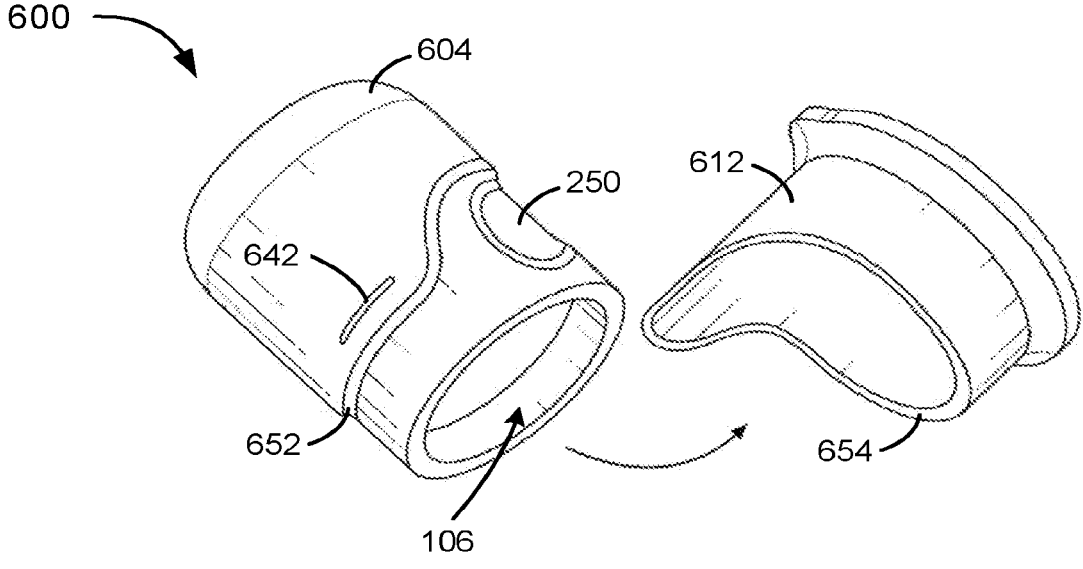
FIG. 6B is another perspective view of the applicator of FIG. 6A, shown with the sealing element separated from the housing

FIG. 6A illustrates another applicator 600 for applying on-skin assembly 102 to skin of a host including a removable cap 612 configured to couple with a housing 604 in a single axial orientation, in accordance with some embodiments. FIG. 6B is a partially exploded view of applicator 600 of FIG. 6A. Applicator 600 comprises substantially all features of applicator 200 of FIGS. 2A and 2B, however, not including peelable tamper indicator 230, including a removable cap 612 and a housing 604 both having shapes that couple in a single axial orientation and when combined limit rotation about the axis, and further including at least one set of one or more ridges or recesses 642, 644 configured to provide a tactile indication of grip to the host.

For example, FIGS. 6A and 6B show housing 604, which may be substantially the same as housing 204 of FIGS. 2A and 2B, however, further including a first set of one or more ridges or recesses 642 configured to provide a tactile indication of grip to the host. Housing 604 may also include a visual indicator 608 located on a surface of housing 604 (as shown located on the top surface). Visual indicator 608 may be a slight protrusion or a slight indentation from the surface of the housing 604. Furthermore, visual indicator 608 may have a shape similar to the shape of the on-skin assembly 102. The orientation of visual indicator 608 may match with the orientation of on-skin assembly 102 within applicator 600. As such, visual indicator 608 may assist in orienting the user to the orientation of the on-skin assembly 102 within the applicator 600 prior to deployment.

Housing 604 further has an irregularly shaped mating edge 652 that is not planar such that housing 604 will properly mate with removable cap 612 in a single axial orientation. Likewise, FIGS. 6A and 6B further show removable cap 612, which may be substantially the same as removable cap 212, however, further including a second set of one or more ridges or recesses 644 configured to provide a tactile indication of grip to the host. Removable cap 612 further has an irregularly shaped mating edge 654 that is complementary in shape to the mating edge of housing 604 such that removable cap 612 will properly mate with housing 604 in the single axial orientation. Removable cap 612 may be detached from housing 604 by twisting removable cap 612 with respect to housing 604, or vice versa, and then pulling removable cap 612 and housing 604 apart. In some embodiments, the irregularly shaped mating edges 652, 654 of housing 604 and removable cap 612 also function as a tamper indication, since any tampering that causes relative displacement in any direction between removable cap 612 and housing 604 would cause their separation, thereby providing visual indication of tampering.

Embodiments Including a Top Cap Actuation Member

Some embodiments can include an actuation member which is coupled to, or integrally formed with, a removable cap. For example, FIG. 7A illustrates a perspective view of an applicator 700 for applying on-skin assembly 102 to skin of a host including a frangible member as a safety configured to prevent activation of an actuation member, in accordance with some embodiments. FIG. 7B is a partially exploded view of applicator 700 of FIG. 7A. Although not shown, applicator 700 may further include insertion assembly 118 and on-skin assembly 102 as described in connection with FIGS. 1A-1C and as will be further described in connection with FIGS. 8B and 8C below.

Applicator 700 comprises a housing 704 configured to house insertion assembly 118 (not shown) and comprises aperture 106 through which on-skin assembly 102 can pass. Housing 704 further comprises a vent 762 configured to be permeable to a sterilizing gas and able to maintain a sterile barrier. In some embodiments, vent 762 may be disposed on a top (i.e., proximal) side of housing 704. In some embodiments, a porous polymeric component is inserted into vent 762, for example, a Porex® plug. In some embodiments, second layer 124, as previously described in connection with FIGS. 1A and 1B, may be disposed directly over aperture 106 after sterilization, thereby providing a moisture barrier at the distal portion of housing 704.

In some embodiments, insertion assembly 118 and on-skin assembly 102 (not shown in detail in FIG. 7B) may be disposed within housing 704 and then second layer 124 may be disposed over aperture 106, thereby sealing the distal portion of housing 704. Ingress and egress of a sterilizing gas may then be achieved through vent 762, after which a sealing layer 764 may be disposed over vent 764 and a proximal portion of housing 704, thereby completely sealing an inside of housing 704 from an outside environment. Accordingly, in some embodiments, the combination of at least housing 704, second layer 124 and sealing layer 764 may form a sealing element configured to provide a sterile barrier and a vapor barrier between an internal environment and an external environment of housing 704.

Applicator 700 further comprises an actuation member 750 comprising a telescoping cap coupled to the proximal portion of housing 704. Accordingly, sealing layer 764 is disposed between the actuation member 750 (i.e., the cap) and housing 704. Actuation member 750 is configured to be activated by moving the cap in a distal direction. Accordingly, actuation member 750 may further comprise a protrusion 752 configured to pierce sealing layer 764 and thereby activate insertion assembly 118 (not shown) within housing 704 when the cap is moved in the distal direction. In some embodiments, actuation member 750 may be spring loaded such that pressure exceeding a threshold is required in order to move the cap in the distal direction sufficiently to activate actuation member 750.

Applicator 700 may further comprise a frangible safety member 766 configured to prevent activation of actuation member 750. In some embodiments, frangible safety member 766 is disposed between actuation member 750 and a distal portion of housing 704 such that frangible safety member 766 physically prevents movement of actuation member 750 at least until frangible safety member 766 is removed or sufficiently displaced. In this way, frangible safety member 766 simultaneously provides a premature deployment feature, a drop protection feature, and a tamper indication.

FIG. 8A illustrates another applicator 800 for applying on-skin assembly 102 to skin of a host including another frangible safety member 866 configured to prevent activation of an actuation member 850, in accordance with some embodiments. Applicator 800 is substantially the same as application 700 previously described in connection with FIGS. 7A and 7B, however, including a few similar features having slightly different shapes, excluding vent 764, and further illustrating a few additional features as described below.

For example, applicator 800 is shown to include housing 704 and second layer 124 as previously described in connection with FIGS. 7A and 7B. Applicator 800 further comprises a frangible safety member 866 having substantially the same function and location as frangible safety member 766 of FIGS. 7A and 7B, however, having a substantially horizontal orientation rather than a substantially vertical orientation. Applicator 800 further comprises actuation member 850 comprising a telescoping cap coupled to the proximal portion of housing 704 and having substantially the same function as actuation member 750 but with a slightly different shape.

FIG. 8B is a cutaway view of applicator 800 of FIG. 8A in a pre-deployment configuration. FIG. 8B further illustrates insertion assembly 118 disposed within housing 704 and sealing layer 764. However, applicator 800 omits vent 764 and sealing layer 764 is instead disposed over an opening in a proximal portion of housing 704. Accordingly, in some embodiments, insertion assembly 118 and on-skin assembly 102 may be disposed within housing 704 and then second layer 124 may be disposed over aperture 106, thereby sealing the distal portion of housing 704. Ingress and egress of a sterilizing gas may then be achieved through the opening in the proximal portion of housing 704, after which sealing layer 764 may be disposed over the opening and over the proximal portion of housing 704, thereby completely sealing an inside of housing 704 from an outside environment. Accordingly, in some embodiments, the combination of at least housing 704, second layer 124 and sealing layer 764 may form a sealing element configured to provide a sterile barrier and a vapor barrier between an internal environment and an external environment of housing 704.

FIG. 8B further illustrates protrusion 752 of actuation member 850 in a position ready to pierce sealing layer 764 when actuation member 850 (e.g., telescoping cap) is moved in a distal direction. Applicator 800 is further illustrated as including a spring feature 854 (e.g. molded or integrated spring feature) configured to provide the biased force loaded aspect of the actuation member 850 as previously described in connection with FIGS. 7A and 7B.

FIG. 8C is a cutaway view of applicator 800 of FIG. 8A in a deployed configuration. As shown, second layer 124 has been removed before deployment and actuation member 850 is shown as having been moved in the distal direction, causing protrusion 752 to pierce sealing layer 764 and activate insertion assembly 118.

Figures 9A, 9B, 9C:
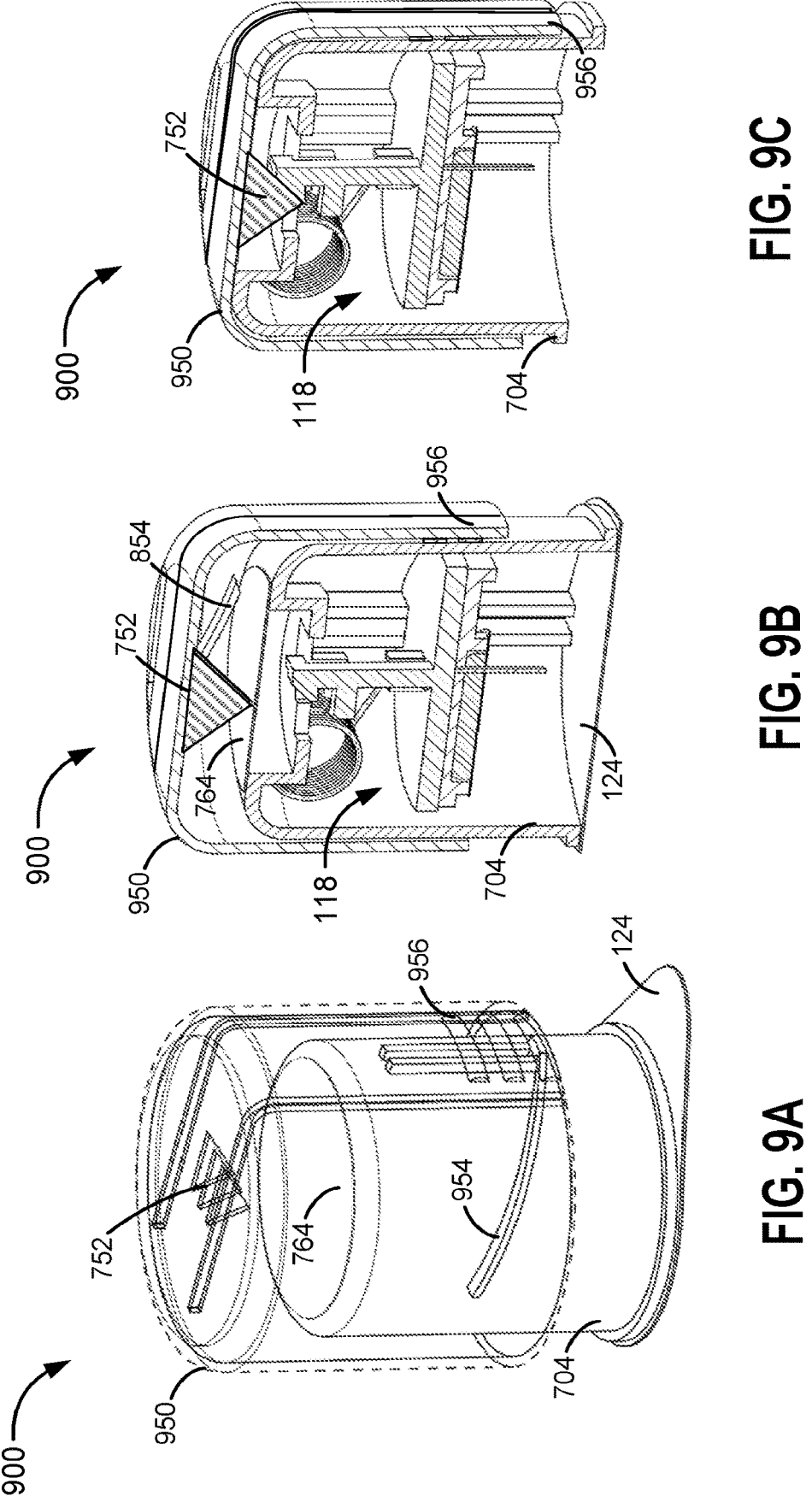
FIG. 9A illustrates a perspective view of an applicator for applying an on-skin assembly to skin of a host including an actuation member configured as a cap disposed over a housing of the applicator, in accordance with some embodiments.
FIG. 9B is a cross-sectional view of the applicator of FIG. 9A in a pre-deployment configuration.
FIG. 9C is a cross-sectional view of the applicator of FIG. 9A in a deployed configuration.

FIG. 9A illustrates another applicator 900 for applying on-skin assembly 102 to skin of a host including an actuation member 950 configured as a cap disposed over housing 704 of applicator 900, in accordance with some embodiments. Applicator 900 is substantially similar to applicator 800 previously described in connection with FIGS. 8A-8C, except as described below. As shown in FIG. 9A, applicator 900 includes housing 704, second layer 124 sealing aperture 106 (not shown) of housing 704 and sealing layer 764 disposed on proximal portion of housing 704. Applicator 900 further comprises actuation member 950 comprising a cap coupled to the proximal portion of housing 704. Actuation member 950 comprises protrusion 752, which is configured to pierce sealing layer 764 during activation of actuation member 950. The cap forming actuation member 950 may further comprise a side flexure 956 configured to unlock actuation member 950. Specifically, moving side flexure 956 allows the actuation member 950 to move in a distal direction arms. Activation member 950 further moves protrusion 752 such that it pierces sealing layer 764 and activates insertion assembly 118 (not shown, see FIGS. 8B and 8C). Furthermore, applicator 900 may not include spring feature 854, but instead comprises a spring feature 954 disposed on a side of housing 704 between housing 704 and the cup of actuation member 950, which may provide substantially the same effect as spring feature 854. In some embodiments, spring feature 954 may be coupled to housing 704 at one end and coupled to the cup forming actuation member 950 at the other end. Actuation member 950 may provide additional premature deployment prevention and drop protection features.

FIG. 9B further illustrates protrusion 752 of actuation member 950 in a position ready to pierce sealing layer 764 when actuation member 950 (e.g., telescoping cap) is moved in a distal direction. Applicator 900 is further illustrated as including the spring feature 954 configured to provide the biased force loaded aspect of the actuation member 950 as previously described.

FIG. 9C is a cutaway view of applicator 900 of FIG. 9A in a deployed configuration. As shown, second layer 124 has been removed before deployment and actuation member 950 is shown as having been moved in the distal direction and side flexure 956 depressed, causing protrusion 752 to pierce sealing layer 764 and activate insertion assembly 118.

Figure 10A:
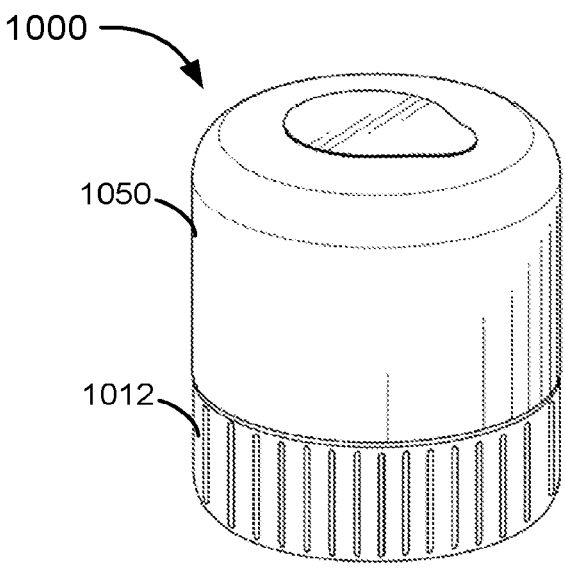
FIG. 10A illustrates a perspective view of an applicator for applying an on-skin assembly to skin of a host including a removable cap configured as a sealing element, in accordance with some embodiments.
Figure 10B:
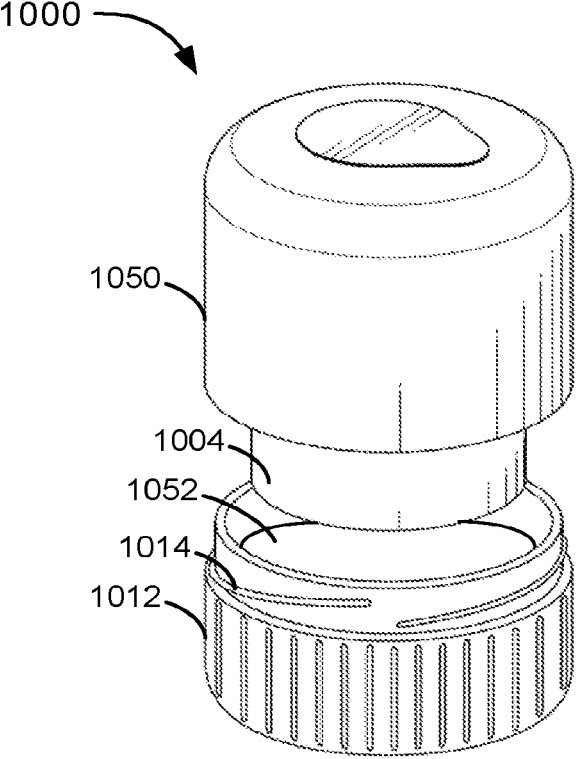
FIG. 10B is a partially exploded view of the applicator of FIG. 10A.

FIG. 10A illustrates another applicator 1000 for applying on-skin assembly 102 to skin of a host including a removable cap 1012 configured as a sealing element, in accordance with some embodiments. FIG. 10B is a partially exploded view of applicator 1000 of FIG. 10A. Discussion of applicator 1000 will now take place with reference to both FIGS. 10A and 10B. Applicator 1000 is substantially the same as applicator 700 of FIGS. 7A and 7B, except as described below. Applicator 1000 comprises a housing 1004, which may function substantially the same as housing 704. Applicator 1000 further comprises a telescoping cap 1050 that functions as an actuation member. Applicator 1000 may not include second layer 124 or frangible safety member 766 of FIGS. 7A and 7B. Instead, applicator 1000 may include a removable cap 1012 configured to couple with a distal portion of telescoping cap 1050 actuation member via threads 1014. In some embodiments, a layer 1052 permeable to a sterilizing gas, e.g., Tyvek®, may be included under removable cap 1012 or alternatively attached to removable cap 1012 such that layer 1052 is removed with removable cap 1012. Threads 1014 disposed on removable cap 1012 may be configured to mate with threads (not shown) disposed on an inside surface of the cap forming actuation member 1050. Removable cap 1012 may be detached from actuation member 1050 by twisting removable cap 1012 with respect to telescoping cap 1050, or vice versa. Since telescoping cap actuation member 1050 is thus coupled to removable cap 1012, applicator 1000 cannot be activated while removable cap 1012 is secured to applicator 1000. Accordingly, removable cap 1012 provides not only a sealing element configured to provide a sterile barrier and a vapor barrier between an internal and external environment of housing 1004, but also at least premature deployment prevention and drop protection features.

Embodiments Including a Flexible Shell

Figures 11A, 11B:
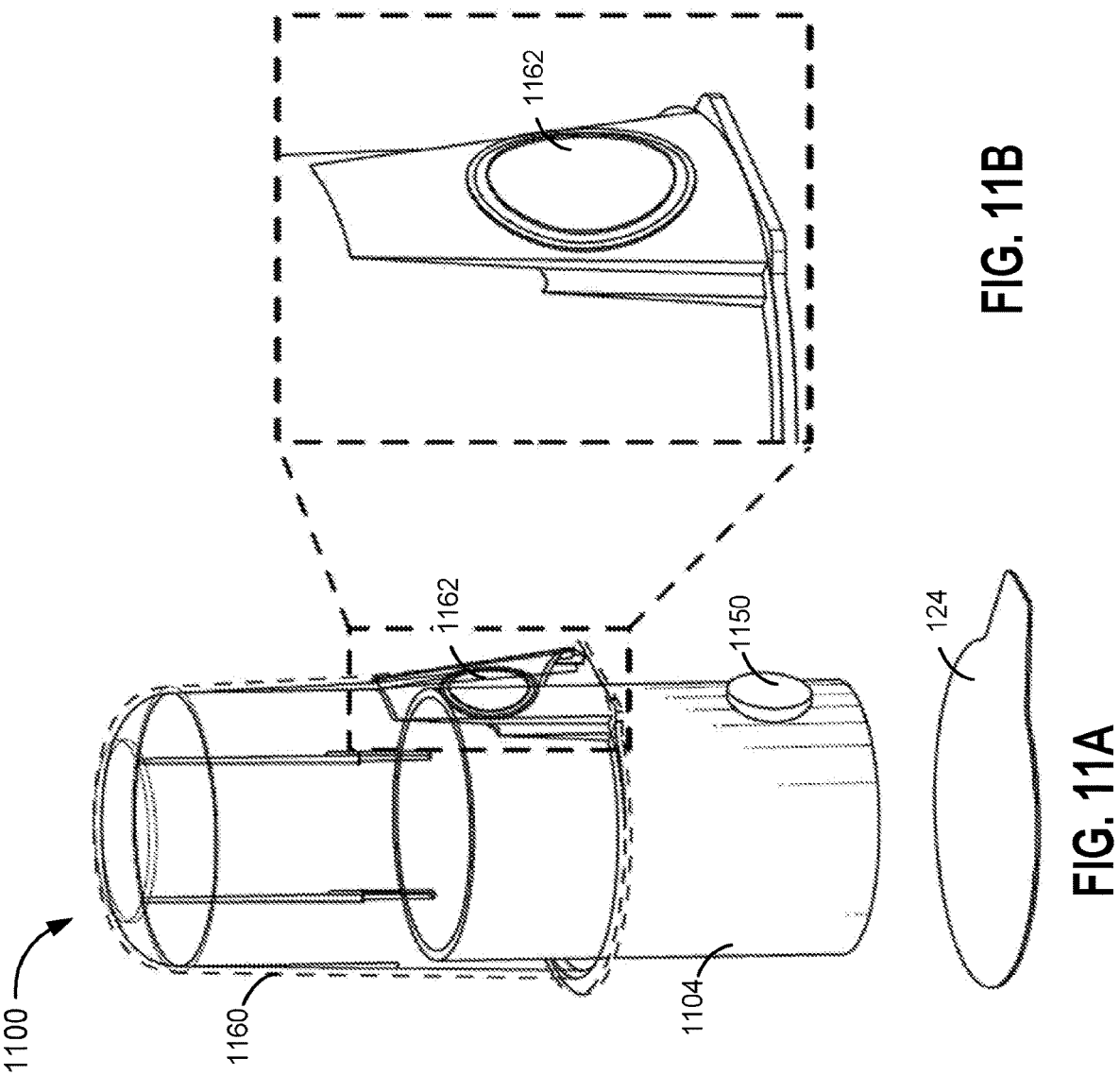
FIG. 11A illustrates a perspective view of an applicator for applying an on-skin assembly to skin of a host including a flexible member disposed over at least a portion of the applicator housing, in accordance with some embodiments.
FIG. 11B is a detail view of a portion of the flexible member of FIG. 11A disposed over an actuation member.

Some embodiments can include a flexible member configured as a shell or cover, which is disposed over the housing and operatively coupled to the actuation member. For example, FIG. 11A illustrates another applicator 1100 for applying on-skin assembly 102 to skin of a host including a flexible member 1160 disposed over at least a portion of a housing 1104, in accordance with some embodiments. Although not shown, applicator 1100 may further include insertion assembly 118 and on-skin assembly 102 as described in connection with at least FIGS. 1A-1C. Applicator 1100 comprises housing 1104, which may encapsulate insertion assembly 118 and on-skin assembly 102. Applicator 1100 may further comprise an actuation member 1150 disposed on a side of housing 1104 and configured to, upon activation, cause insertion assembly 118 to insert at least a portion of on-skin assembly into the skin of a host. Applicator 1100 may further comprise flexible member 1160 disposed over housing 1104. Applicator 1100 may further comprise second layer 124, which may seal a distal portion of flexible member 1160. Thus, second layer 124 in conjunction with flexible member 1160 provide a sealing element configured to provide a sterile barrier and a vapor barrier between an internal and external environment of housing 1104. As shown in FIG. 11A, flexible member 1160 may comprise a flexible section 1162 configured to be disposed over actuation member 1150 such that when flexible section 1162 is pressed, actuation member 1150 is activated. In some embodiments, flexible section 1162 may be bistable in that it has two states: a first, loaded state and a second, deployed state. In such embodiments, flexible section 1162 may provide a positive visual tamper indication when in the second, deployed state. Moreover, the flexible nature of flexible member 1160 may additionally provide premature deployment prevention and drop protection features by absorbing energy that might otherwise provide a physical shock to applicator 1100.

FIG. 11B is a zoomed view of a portion of flexible member 1160 of FIG. 11A disposed over actuation member 1150. FIG. 11B merely shows flexible section 1162 of flexible member 1160 in greater detail.

Figure 12A:
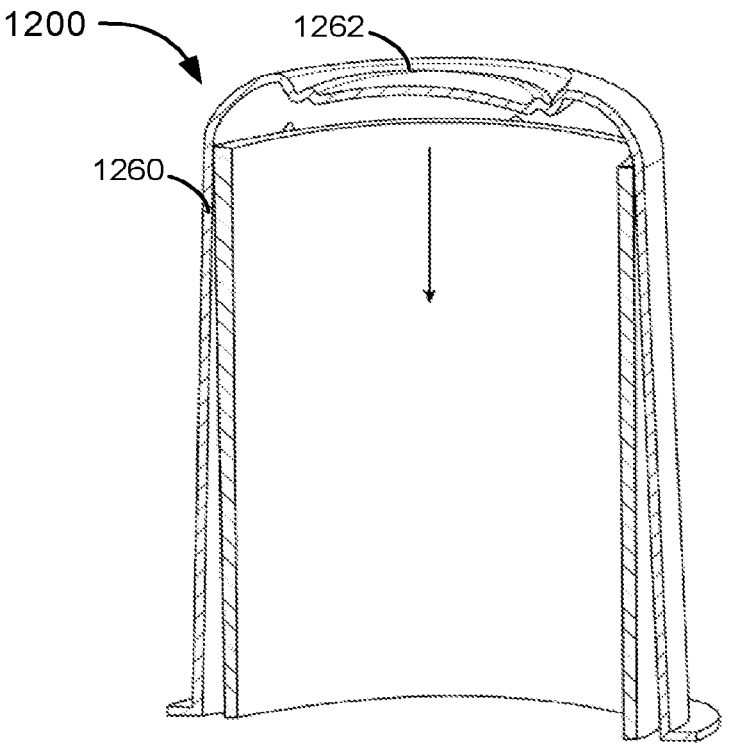
FIG. 12A illustrates a cross-sectional view of an applicator for applying an on-skin assembly to skin of a host including a flexible member having a bistable configuration that provides a visual indication of deployment, in accordance with some embodiments.
Figure 12B:
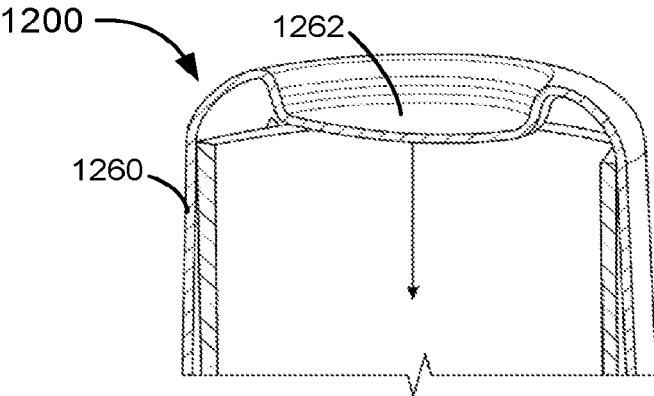
FIG. 12B is a detail cross-sectional view of a portion of the bistable configuration of the flexible member of FIG. 12A.

FIG. 12A illustrates another applicator 1200 for applying on-skin assembly 102 to skin of a host including a flexible member 1260 having a bistable configuration that provides a visual indication of deployment, in accordance with some embodiments. FIG. 12B is a zoomed view of a portion of the bistable configuration of flexible member 1200 of FIG. 12A. Applicator 1200 is substantially the same as applicator 1100 of FIGS. 11A and 11B, except the actuation member (not shown) is disposed on a proximal portion of the housing (not shown) and flexible member 1260 comprises a molded accordion-like section 1262 disposed on a proximal portion of flexible member 1260 and configured to be disposed over the actuation member such that when molded accordion-like section 1262 is pressed, the top-mounted actuation member is activated. FIG. 12A illustrates molded accordion-like section 1262 in the first, loaded state, while FIG. 12B illustrates molded accordion-like section 1262 in the second, deployed state.

Figures 13A, 13B, 13C:
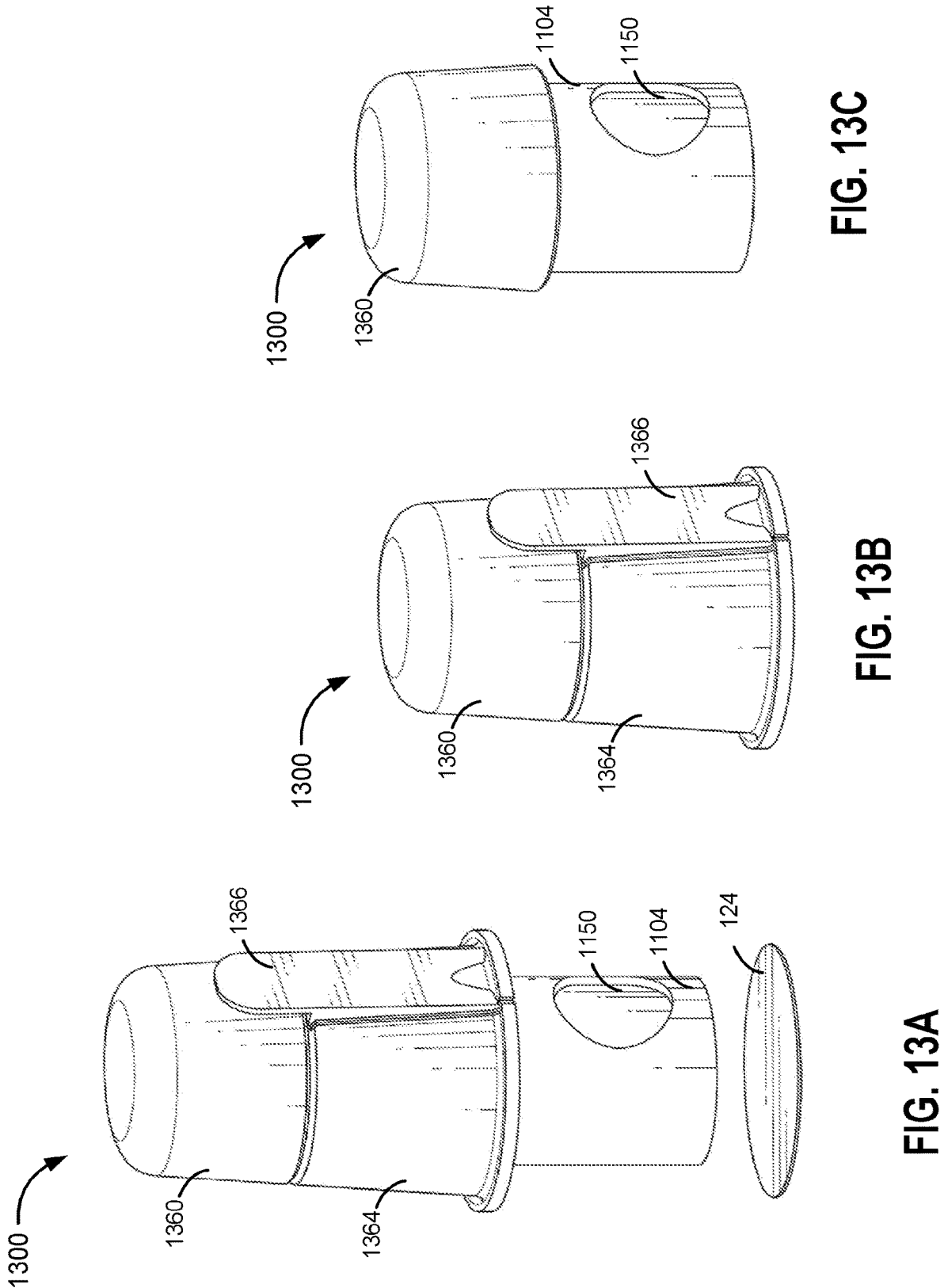
FIG. 13A is an exploded view of an applicator for applying an on-skin assembly to skin of a host including a frangible member configured to cover an actuation member, in accordance with some embodiments.
FIG. 13B is an assembled view of the applicator of FIG. 13A.
FIG. 13C illustrates a perspective view of the applicator of FIGS. 13A and 13B having the frangible member removed, thereby exposing an actuation member.

FIG. 13A is an exploded view of another applicator 1300 for applying on-skin assembly 102 to skin of a host including a flexible member 1360 comprising a frangible member 1364 configured to cover an actuation member 1350, in accordance with some embodiments. Applicator 1300 is substantially the same as applicator 1100 of FIGS. 11A and 11B, except as described below. Applicator 1300 comprises housing 1104 of FIGS. 11A and 11B, which comprises actuation member 1150 disposed on a side of housing 1104. Applicator 1300 further comprises a flexible member 1360, which itself comprises a frangible member 1364 and a frangible tab 1366. Applicator 1300 further comprises second layer 124 and, in some embodiments, first layer 122, disposed over a distal opening in flexible member 1360. In this way, flexible member 1360, second layer 124, and in embodiments including it, first layer 122, may form a sealing element configured to provide a sterile barrier and a vapor barrier between and internal environment and an external environment of housing 1304. By pulling down on frangible tab 1366 and then pulling around applicator 1300, frangible tab 1366 and frangible member 1360 may be removed in preparation of using applicator 1300. Thus, at least frangible member 1360 and frangible tab 1366 may simultaneously provide joint sterilization and moisture seals, tamper indication, as well as premature deployment prevention and drop protection features.

FIG. 13B is a condensed view of applicator 1300 of FIG. 13A before removal of frangible member 1360 and frangible tab 1366. FIG. 13C illustrates applicator 1300 of FIGS. 13A and 13B having the frangible member 1364 removed, thereby exposing actuation member 1350.

Figure 14:
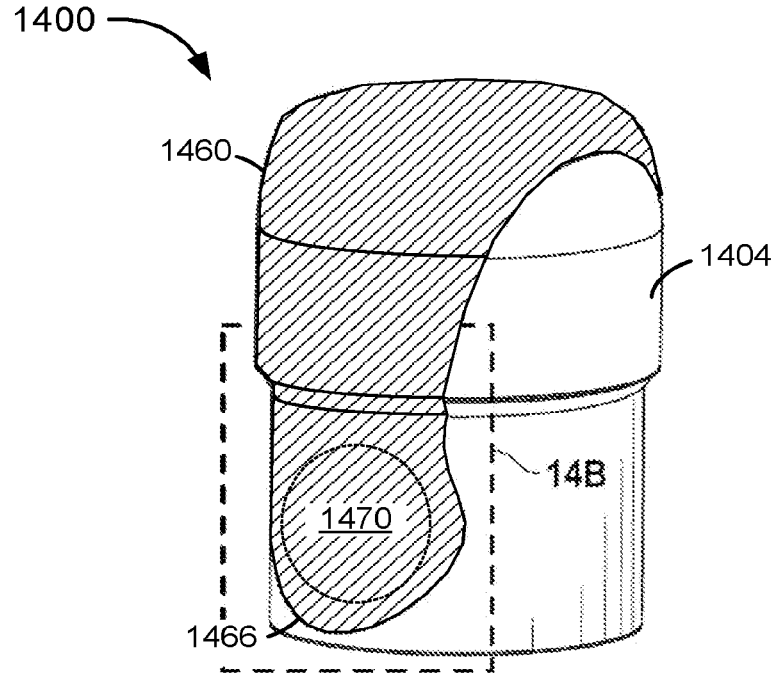
FIG. 14 illustrates a perspective view of an applicator for applying an on-skin assembly to skin of a host including a frangible portion having a flexible tab molded around an actuation member, in accordance with some embodiments.

FIG. 14 illustrates another applicator 1400 for applying on-skin assembly 102 to skin of a host including a main portion 1460 disposed over at least a portion of applicator 1400 and comprising a flexible material, in accordance with some embodiments. Applicator 1400 comprises a housing 1404 configured to house insertion assembly 118 (not shown) and comprising an aperture 106 (not shown) through which on-skin assembly 102 (not shown) can pass. Applicator 1400 further comprises an actuation member 1470 configured to, upon activation, cause the insertion assembly to insert at least the portion of on-skin assembly 102 into the skin of the host. Main portion 1460 may comprise, for example, rubber, silicone, or any other flexible, soft material that provides shock protection as well as grip to a user. Main portion 1460 may be overmolded together with housing 1404. Main portion 1460 may additionally cover actuation member 1470, thereby providing some measure of accidental activation protection, as well as providing additional sealing for applicator 1400. Main portion 1460 may extend over at least a proximal portion of housing 1404, thereby providing both a grip for the host as well as drop protection. Main portion 1460 may comprise an elastomeric material configured to absorb at least a portion of energy imparted to applicator 1400 when dropped. Furthermore, in other embodiments, main portion 1464 may be removed by pulling a flexible tab 1466 away from applicator 1400 to reveal a hidden button. In such embodiments, main portion 1464 can provide additional tamper indication or button activation prevention features.

Additional Embodiments

Figure 15A:
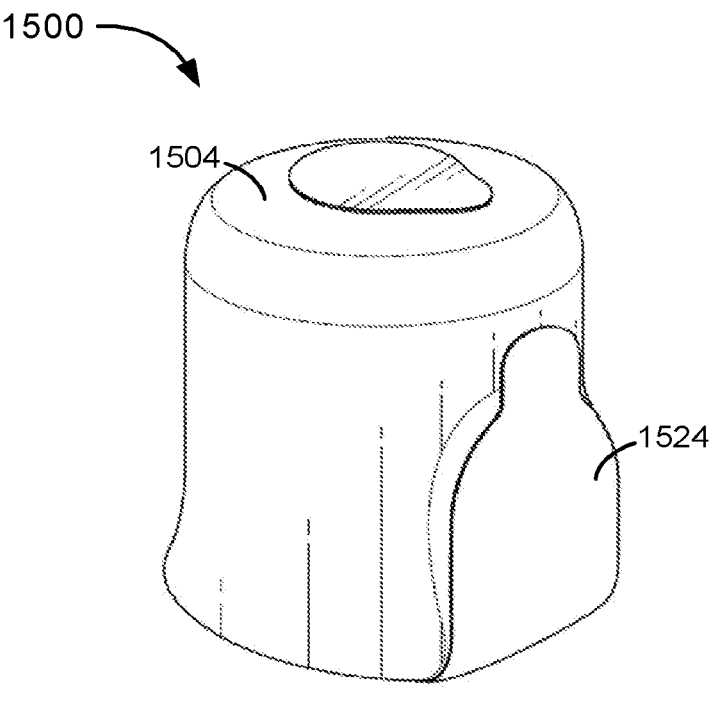
FIG. 15A illustrates a perspective view of an applicator for applying an on-skin assembly to skin of a host including a peelable layer configured to seal a distal opening in a housing and to further seal an actuation member, in accordance with some embodiments.
Figure 15B:
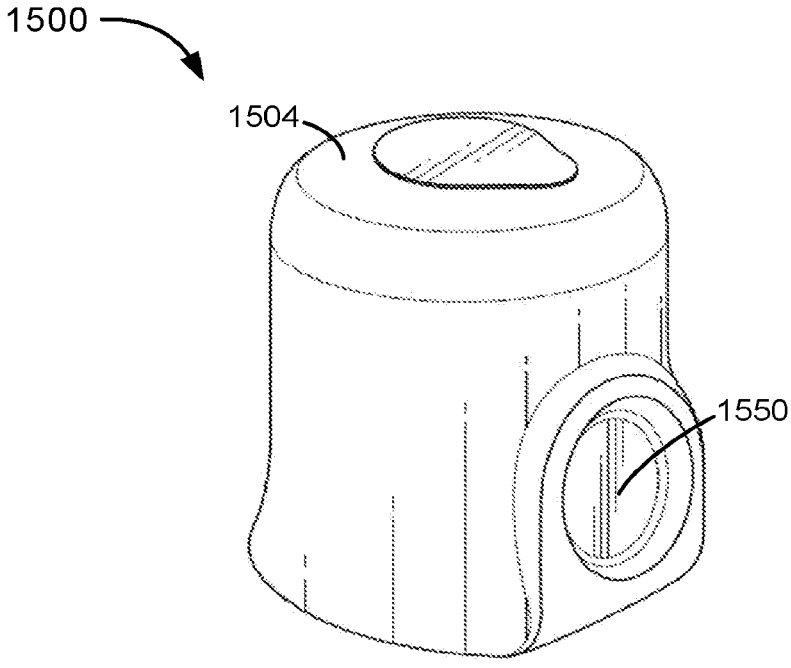
FIG. 15B illustrates the applicator of FIG. 15A having the peelable layer removed.

Alternatively or in addition to a removable cap, various embodiments can include one or more other features configured to provide a sterilization seal and/or moisture barrier. A subset of such embodiments may comprise a single housing without a top or bottom cap. For example, FIG. 15A illustrates a perspective view of an applicator 1500 for applying on-skin assembly 102 to skin of a host including a peelable layer 1524 configured to seal a distal opening 106 in a housing 1504 and to further seal an actuation member 1550, in accordance with some embodiments. Applicator 1500 comprises housing 1504 configured to house insertion assembly 118 and comprises aperture 106 through which on-skin assembly 102 can pass. Applicator 1500 further comprises actuation member 1550 disposed on a side of housing 1504 and configured to, upon activation, cause insertion assembly 118 to insert at least a portion of on-skin assembly into the skin of a host. In some embodiments, peelable layer 1524 is coupled to at least a portion of housing 1524. For example, as shown in at least FIG. 15A peelable layer 1524 is configured to seal aperture 106 and actuation member 1550. Thus, peelable layer 1524 forms a sealing element configured to provide a sterile barrier and/or a vapor barrier between an internal and external environment of housing 1504. In some embodiments, peelable layer 1524 is a single piece forming the sealing element. Applicator 1500 may be readied for use by removing peelable layer 1524, thereby exposing both aperture 106 and actuation member 1550. In this way, peelable layer 1524 may also simultaneously provide a tamper indication, premature deployment prevention and drop protection features. FIG. 15B illustrates applicator 1500 of FIG. 15A having peelable layer 1524 removed.

Figure 16A:
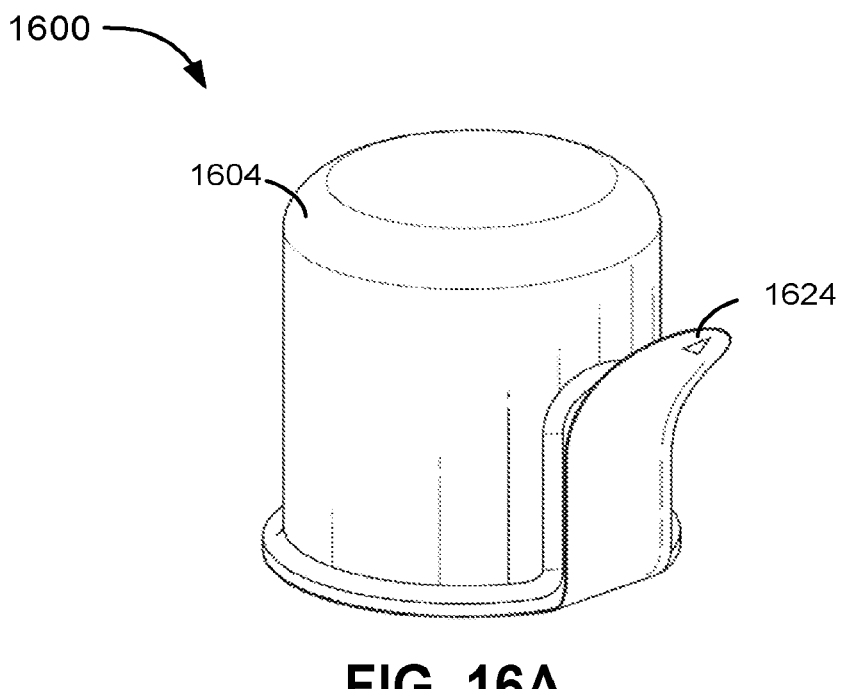
FIG. 16A illustrates a perspective view of an applicator for applying an on-skin assembly to skin of a host including a peelable layer configured to seal a distal opening in a housing, to further seal an actuation member, and to further seal vent permeable to a sterilizing gas, in accordance with some embodiments.
Figure 16B:
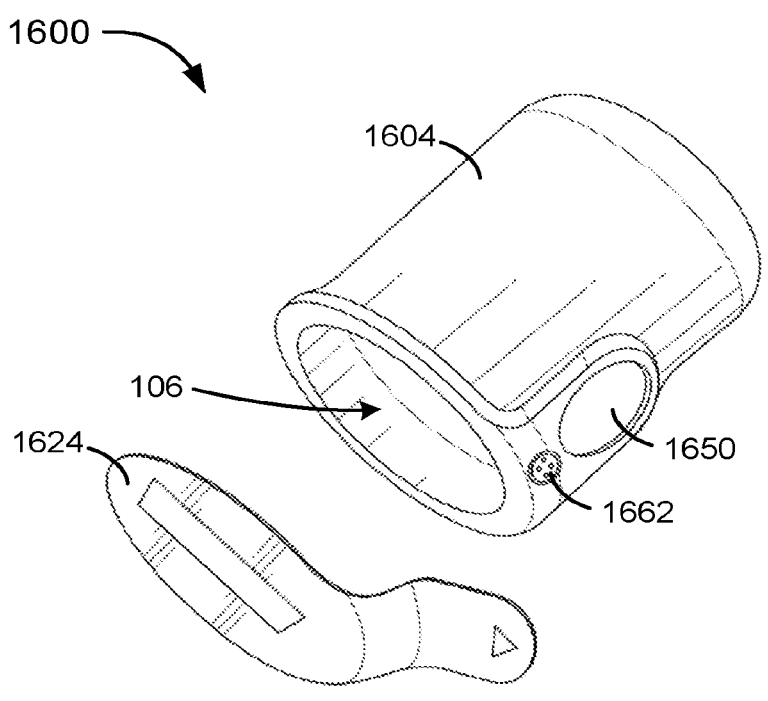
FIG. 16B is a partially exploded view of the applicator of FIG. 16A.

FIG. 16A illustrates another applicator 1600 for applying on-skin assembly 102 to skin of a host including a peelable layer 1624 configured to seal a distal aperture 106 in a housing 1604, to further seal an actuation member 1650, and to further seal a vent 1662 permeable to a sterilizing gas, in accordance with some embodiments. FIG. 16B is a partially exploded view of applicator 1600 of FIG. 16A. Applicator 1600 comprises a housing 1604 configured to house an insertion assembly, such as insertion assembly 118 shown in FIG. 8B, and comprises an aperture 106 through which an on-skin assembly, such as on-skin assembly 102 shown in FIG. 1B, can pass. Applicator 1600 further comprises actuation member 1650 disposed on a side of housing 1604 and configured to, upon activation, cause insertion assembly 118 to insert at least a portion of on-skin assembly into the skin of a host. Applicator 1600 further comprises vent 1662 configured to be permeable to a sterilizing gas. In some embodiments, a porous polymeric component (e.g., a Porex® plug) may be inserted into vent 1662. In some embodiments, vent 1662 may be disposed on a side of housing 1604, for example, in some embodiments, facing substantially radially outward and substantially perpendicular to aperture 106. In some embodiments, peelable layer 1624 is coupled to at least a portion of housing 1624. For example, as shown in at least FIG. 16A peelable layer 1624 is configured to seal aperture 106, actuation member 1650, and vent 1662, e.g., alone two faces of the applicator, one of which comprises vent 1662. Thus, peelable layer 1624 forms a sealing element configured to provide a sterile barrier and/or a vapor barrier between an internal and external environment of housing 1604. For example, peelable layer 1624 may be adhered to housing 1604 thereby sealing aperture 106 on a distal face of housing 1604 but not yet sealing vent 1662. Applicator 1600 may then be subjected to a sterilizing gas, which may permeate still-exposed vent 1662, thereby sterilizing the inside of housing 1604. Peelable layer 1624 may then be disposed over vent 1662 on a second face of housing 1604, thereby sealing vent 1662 and providing a moisture barrier. Applicator 1600 may be readied for use by removing peelable layer 1624, thereby exposing both aperture 106 and actuation member 1650. In this way, peelable layer 1624 may also simultaneously provide a tamper indication, premature deployment prevention and drop protection features.

Figures 17A, 17B, 17C:
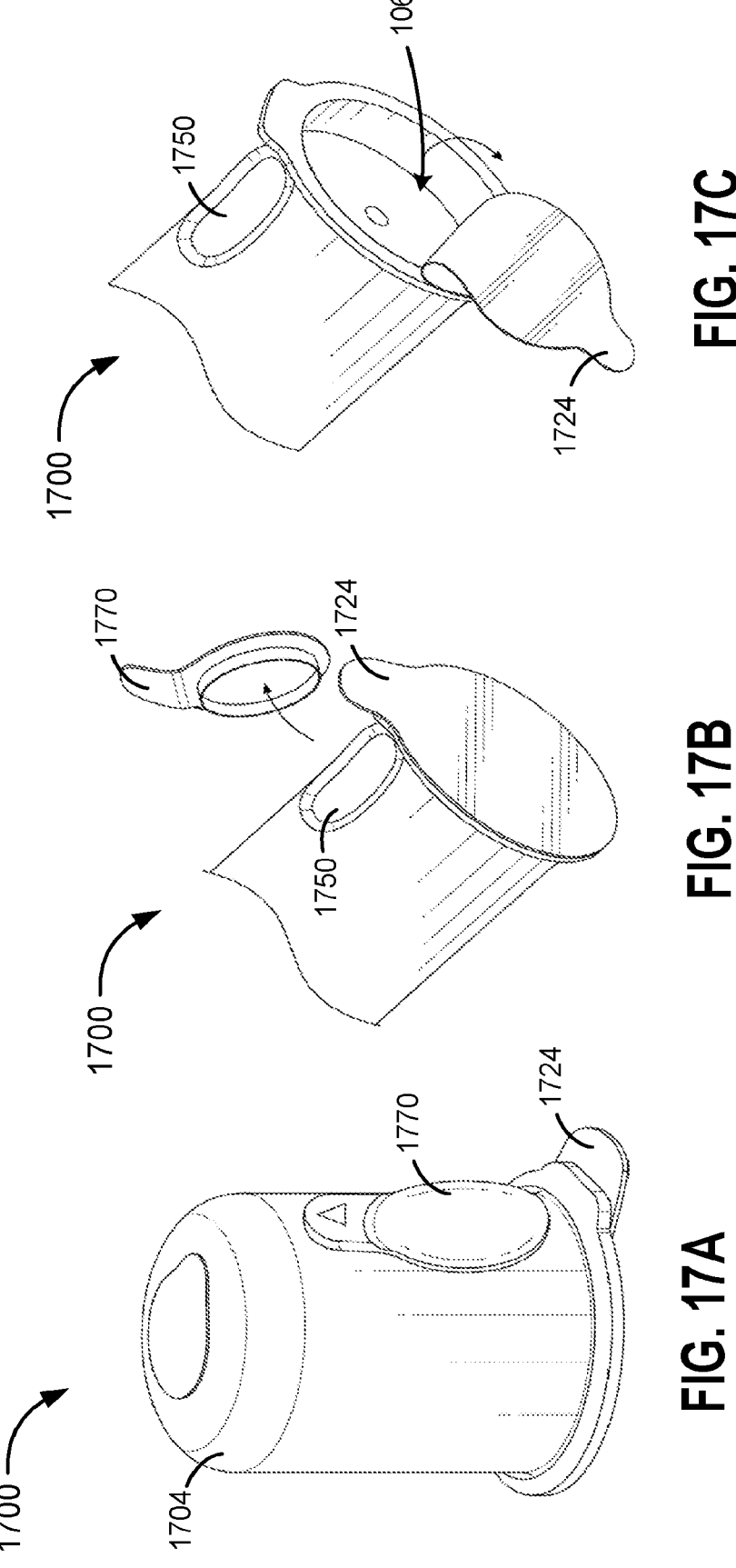
FIG. 17A illustrates a perspective view of an applicator for applying an on-skin assembly to skin of a host including a peelable layer configured to seal a distal opening in a housing and a inset plug configured to seal an actuation member, in accordance with some embodiments.
FIG. 17B illustrates the applicator of FIG. 17A with the inset plug removed.
FIG. 17C illustrates the applicator of FIG. 17A with the peelable layer at least partially removed.

FIG. 17A illustrates a perspective view of an applicator 1700 for applying on-skin assembly 102 to skin of a host including a peelable layer 1724 configured to seal a distal aperture 106 in a housing 1704 and a inset plug or cap 1770 configured to seal an actuation member 1750, in accordance with some embodiments. Applicator 1700 comprises housing 1704 configured to house insertion assembly 118 and comprises an aperture 106 through which on-skin assembly 102 can pass. Applicator 1700 further comprises actuation member 1750 (see FIGS. 17B and 17C) disposed on a side of housing 1704 and configured to, upon activation, cause insertion assembly 118 to insert at least a portion of on-skin assembly into the skin of a host. Applicator 1700 further comprises peelable layer 1724 coupled to at least a portion of housing 1724. For example, as shown in at least FIG. 17A peelable layer 1724 is configured to seal aperture 106. Applicator 1700 further comprises inset plug 1770 configured to seal around actuation member 1750. Thus, peelable layer 1724 and inset plug 1770 form a sealing element configured to provide a sterile barrier and/or a vapor barrier between an internal and external environment of housing 1704. As will be described in more detail in connection with FIGS. 17B and 17C, applicator 1700 may be readied for use by removing peelable layer 1724 and inset plug 1770, thereby exposing aperture 106 and actuation member 1750, respectively. In this way, peelable layer 1724 and/or inset plug 1770 may simultaneously provide at least tamper indication and premature deployment prevention features.

FIG. 17B illustrates applicator 1700 of FIG. 17A with inset plug 1770 removed. As shown, once inset plug 1770 is removed actuation member 1750 is exposed and readied for activation.

FIG. 17C illustrates the applicator of FIG. 17B with peelable layer 1724 further at least partially removed. As shown, once peelable layer 1724 is removed aperture 106 is exposed and applicator 1700 is readied for use by a host.

Figure 36A:
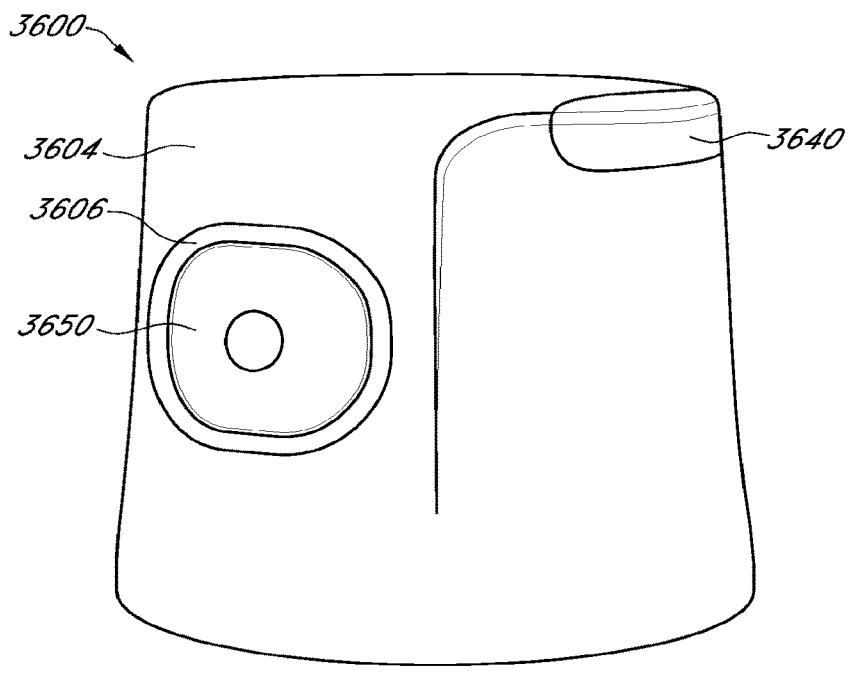
FIG. 36A illustrates a perspective view of an applicator for applying an on-skin assembly to skin of a host including a sliding safety lock feature, in accordance with some embodiments.
Figure 36B:
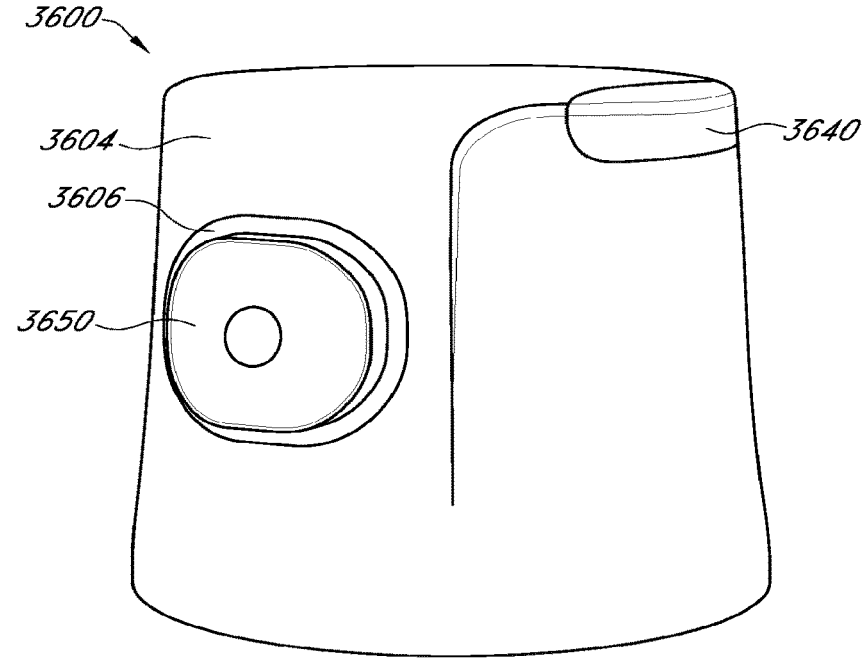
FIG. 36B is a perspective view of the applicator of FIG. 36A illustrating the actuation member in a second state.

FIG. 36A illustrates a perspective view of an applicator 3600 including a housing 3604, a sliding safety lock feature 3640, and an actuation member 3650, in accordance with some embodiments. Safety lock feature 3640 may include at least one button located near the top of housing 3604. In some embodiments, safety lock feature 3640 includes two buttons located at opposite sides of the top of housing 3604. As shown in FIG. 36A, actuation member 3650 is in a locked position in which an outer surface of actuation member 3650 may be flush with an outer surface 3606 of housing 3604. In this locked position, actuation member 3650 cannot be pressed by the user to trigger an internal insertion assembly. As shown in FIG. 36B, safety lock feature 3640 has been pressed. By actuating safety lock feature 3640, an internal latching component releases actuation member 3650 from the locked position to an unlocked position. The outer surface of actuation member 3650 protrudes radially outwards from the outer surface 3606 of housing 3604. In this unlocked position, actuation member 3650 can be pressed by the user to trigger an internal insertion assembly.

Figure 37A:
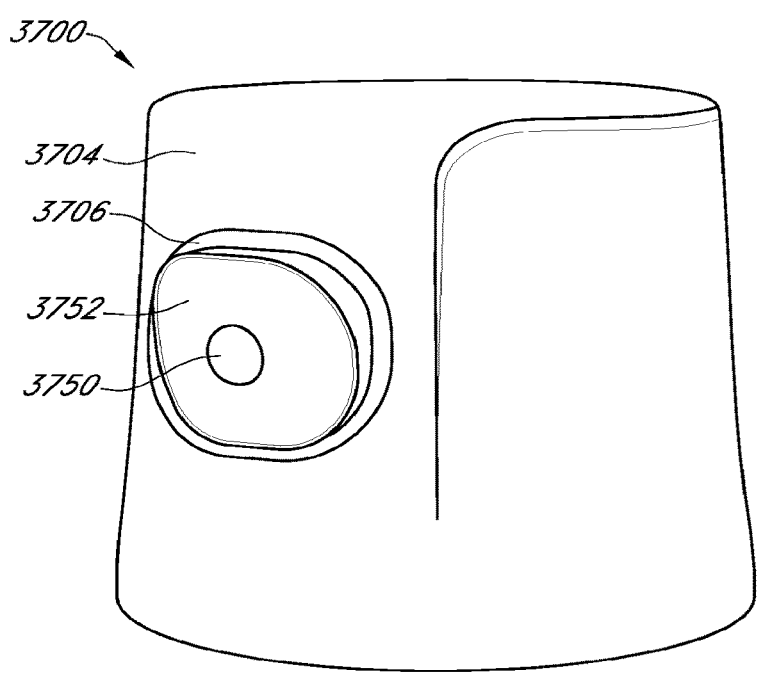
FIG. 37A illustrates a perspective view of an applicator for applying an on-skin assembly to skin of a host with a two state actuation member, in accordance with some embodiments.
Figure 37B:
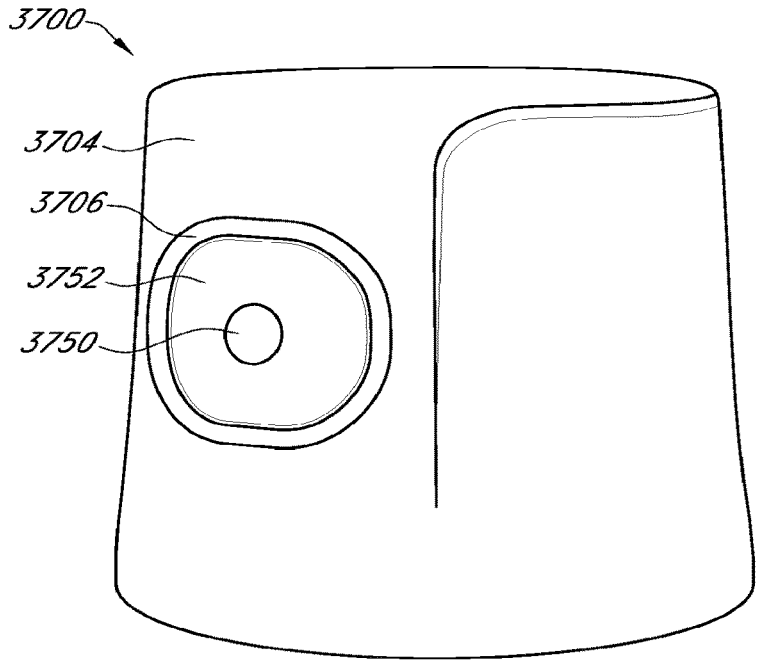
FIG. 37B is a perspective view of the applicator of FIG. 37A illustrating the actuation member in a second state.

FIG. 37A illustrates a perspective view of an applicator 3700 including a housing 3704 and a toggleable actuation member 3750, in accordance with some embodiments. Toggleable actuation member 3750 may feature two states: a locked state and an unlocked state. As shown in the figure, toggleable actuation member 3750 is in a locked state. In this state, an outer surface 3752 of toggleable actuation member 3750 protrudes at an angle from an outer surface 3706 of housing 3704. The angle of toggleable actuation member 3750 can signify to the user that the applicator is locked and cannot be triggered for sensor insertion. Further, toggleable actuation member 3750 cannot be pressed radially inwards to trigger an internal insertion assembly. As shown in FIG. 37B, toggleable actuation member 3750 is in an unlocked state. A user can press on a top portion of toggleable actuation member 3750 to deflect toggleable actuation member 3750 such that out surface 3752 is flush with the outer surface 3706 of housing 3704. In this state, toggleable actuation member 3750 can be pressed radially inward to trigger the internal insertion assembly.

Figures 38A, 38B:
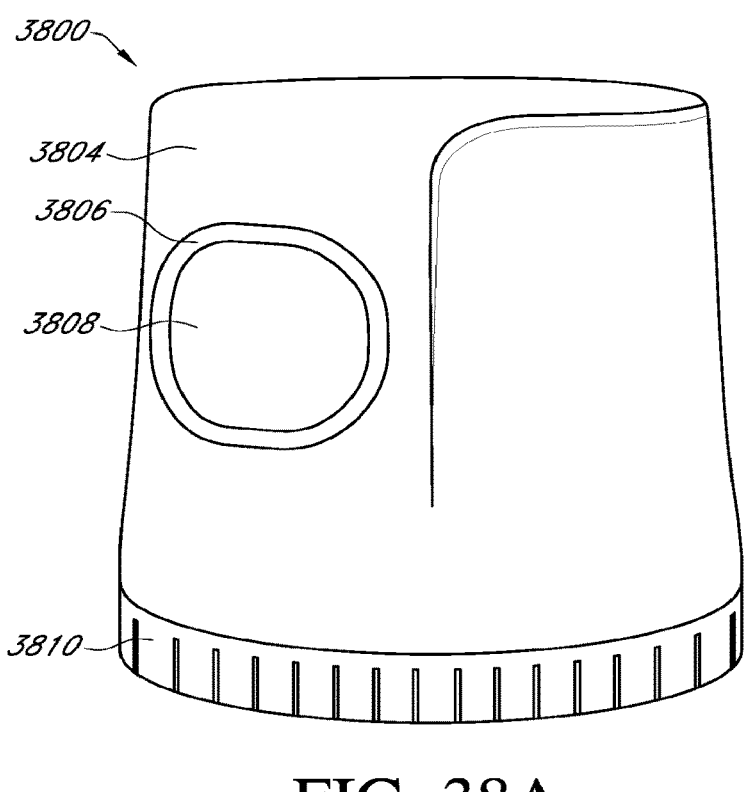
FIG. 38A illustrates a perspective view of an applicator for applying an on-skin assembly to skin of a host including a rotating safety lock feature, in accordance with some embodiments.
FIG. 38B is a perspective view of the applicator of FIG. 38A illustrating the actuation member in a second state.

FIG. 38A illustrates a perspective view of an applicator 3800 including a housing 3804 having an outer surface 3806, an actuation member 3850, and a rotating safety lock feature 3810, in accordance with some embodiments. As shown in the figure, housing 3804 may include an aperture 3808. Aperture 3808 may be configured for actuation member 3850 to extend through. In a locked state, as shown in the figure, actuation member 3850 is a spring button contained with an interior of housing 3804. In this state, applicator 3800 cannot be triggered to insert a sensor via actuation member 3850. As shown in FIG. 38B, rotating safety lock feature 3810 can be rotated in a clockwise or counterclockwise direction. As a user rotates safety lock feature 3810, actuation member 3850 is rotated in a corresponding direction within housing 3804. The user can rotate safety lock feature 3810 until actuation member 3850 reaches an unlocked state. In the unlocked state, due to the spring like nature of actuation member 3850, actuation member 3850 extends out of aperture 3808 past outer surface 3806. In this state, actuation member 3850 can be pressed radially inwards by a user to trigger an internal insertion assembly.

Figure 39:
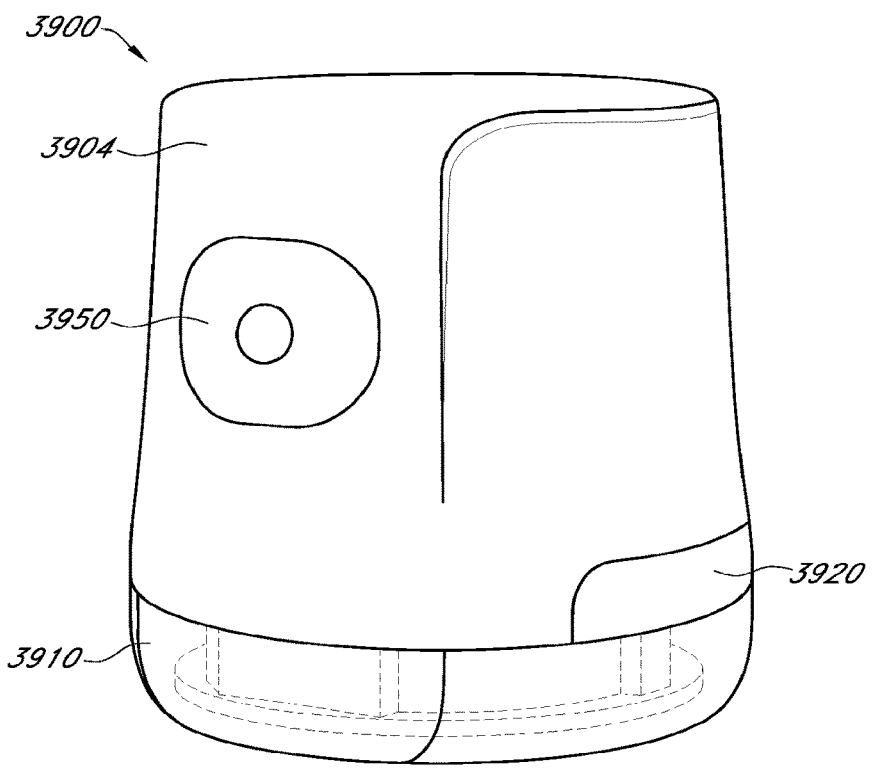
FIG. 39 illustrates a perspective view of an applicator for applying an on-skin assembly to skin of a host including a removable cap release feature, in accordance with some embodiments.

FIG. 39 illustrates a perspective view of an applicator 3900 including a housing 3904, an actuation member 3950, a removable cap 3910, and a release button 3920, in accordance with some embodiments. Release button 3920 may be pressed to release removable cap 3910. In such embodiments, release button 3920 may feature a delatching assembly to detach removable cap 3910 from housing 3904. Release button 3920 may be incorporated into other removable cap applicator embodiments, such as but not limited to FIGS. 2A-2B, 4A-4B, 5A-5B, 6A-6B, 10A-10B, 18A-18B, 34A-34D, and 35A-35B.

Figure 40:
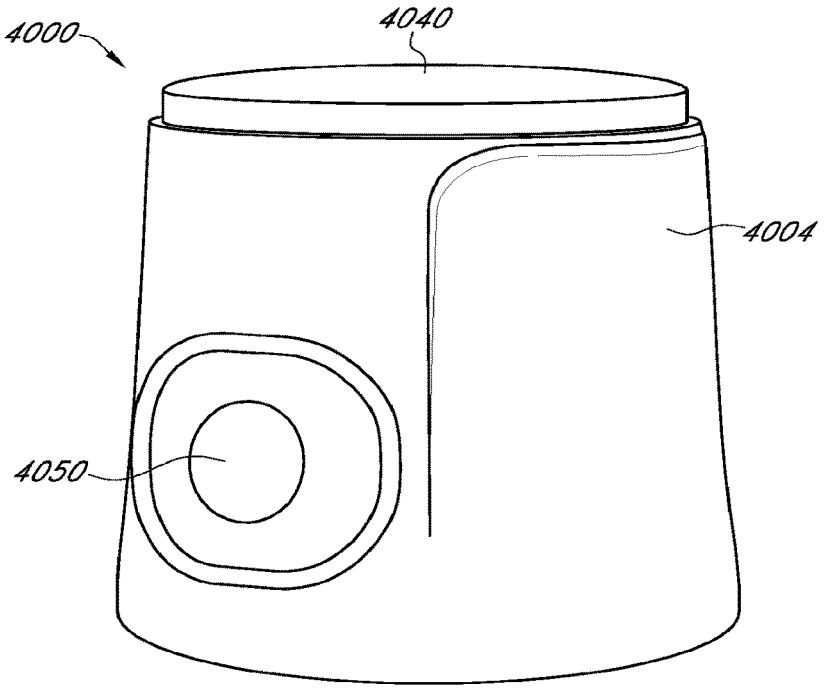
FIG. 40 illustrates a perspective view of an applicator for applying an on-skin assembly to skin of a host including a push button safety lock feature, in accordance with some embodiments.

FIG. 40 illustrates a perspective view of an applicator 4000 including a housing 4004, a safety button 4040, and an actuation member 4050, in accordance with some embodiments. As shown in the figure, safety button 4040 may be located at the top of housing 4004. In such embodiments, safety button 4040 may be pressed in a distal direction to change actuation member 4050 from a locked state to an unlocked state. Actuation of safety button 4040 may disengage internal trigger lock features preventing actuation of actuation member 4050.

Additional Removable Cap Embodiments

Figure 18A:
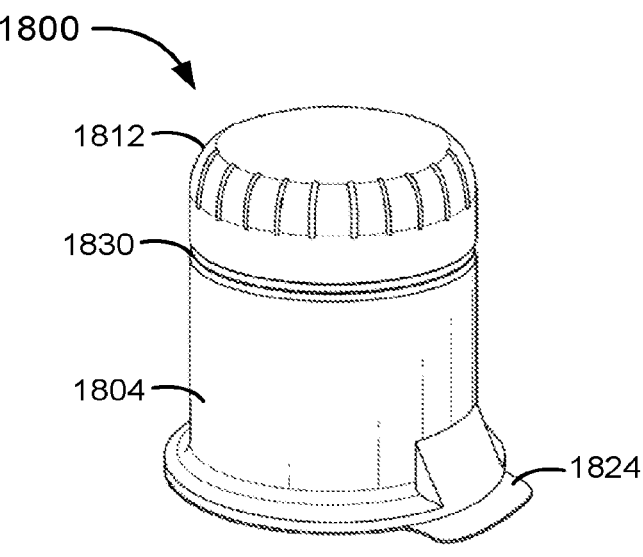
FIG. 18A illustrates a perspective view of an applicator for applying an on-skin assembly to skin of a host including a removable cap configured to seal an actuation member and a peelable layer configured to seal a distal opening in a housing, in accordance with some embodiments.
Figure 18B:
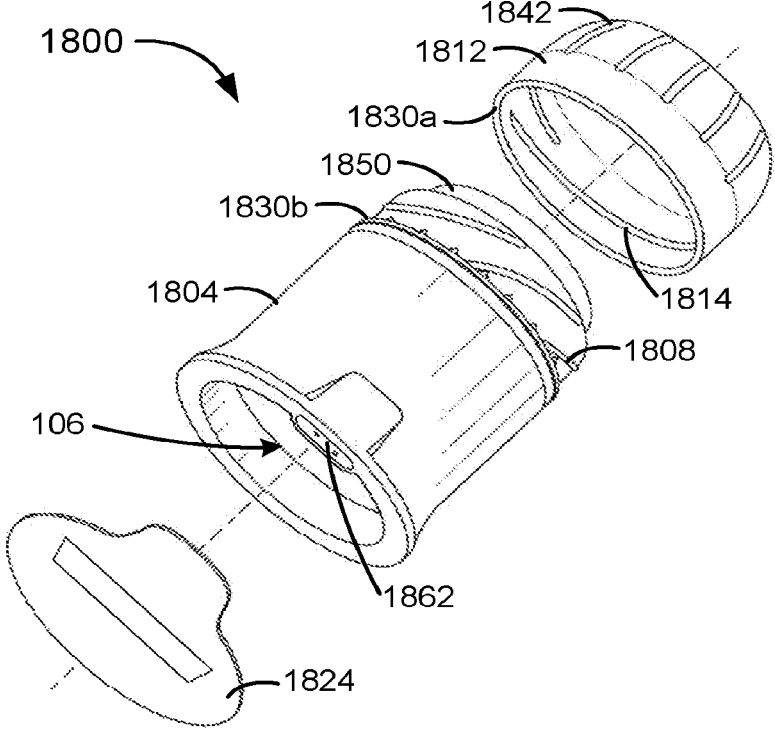
FIG. 18B is a partially exploded view of the applicator of FIG. 18A.

FIG. 18A illustrates a perspective view of an applicator 1800 for applying on-skin assembly 102 to skin of a host including a removable cap 1812 configured to seal an actuation member and a peelable layer configured to seal a distal opening in a housing, in accordance with some embodiments. FIG. 18B is a partially exploded view of applicator 1800 of FIG. 18A. Applicator 1800 comprises a housing 1804 configured to house insertion assembly 118 (not shown) and comprising aperture 106 through which on-skin assembly 102 can pass. Applicator 1800 further comprises actuation member 1850 disposed on a proximal (i.e., top) of housing 1804 and configured to, upon activation, cause insertion assembly 118 to insert at least a portion of on-skin assembly into the skin of a host. In some embodiments actuation member 1850 protrudes from the proximal portion of housing 1804. Applicator 1800 may further comprises vent 1862 configured to be permeable to a sterilizing gas. In some embodiments, a porous polymeric component (e.g., a Porex® plug) may be inserted into vent 1862. In some embodiments, vent 1862 may be disposed on a distal portion of housing 1804, for example, adjacent to aperture 106, and may face in substantially the same distal direction as aperture 106. Applicator 1800 further comprises peelable layer 1824 coupled to at least a portion of housing 1804. For example, as shown in at least FIG. 18A peelable layer 1824 is configured to seal aperture 106 and vent 1862 along a single planar surface (i.e., a distal surface of housing 1804). Thus, peelable layer 1824 forms a sealing element configured to provide a sterile barrier and/or a vapor barrier between an internal and external environment of housing 1804.

Applicator 1800 further comprises removable cap 1812 configured to couple with a proximal (i.e., top) portion of housing 1804. In some embodiments, removable cap 1812 further comprises one or more ridges or recesses 1842 configured to provide a tactile indication of grip to the host. In some embodiments, removable cap 1812 is configured to couple with housing 1804 via threads. For example, threads 1814 disposed on removable cap 1812 may be configured to mate with threads 1808 disposed on housing 1804. In some embodiments, applicator 1804 may further comprise a tamper-evident twist-off collar 1830, disposed at a mating location between housing 1804 and removable cap 1812. As previously described in connection with FIGS. 5A and 5B, a first portion 1830a of tamper-evident twist-off collar 1830 may be coupled to removable cap 1812 and a second portion 1830b of tamper-evident twist-off collar 1830 may be coupled to housing 1804. Removable cap 1812 may be detached from housing 1804 by twisting removable cap 1812 with respect to housing 1804, or vice versa, until first portion 1830a breaks free of second portion 1830b, and threads 1808 and 1814 are no longer mated and then pulling removable cap 1812 and housing 1804 apart. In its integral state, removable cap 1812 may provide a seal (e.g., a sterile barrier and a moisture or water vapor barrier) with housing 1804. In its separated state, tamper-evident twist-off collar 1830 may provide an indication of tampering to a user. Accordingly, peelable layer 1824, tamper-evident twist-off collar 1830, and removable cap 1812 may form a sealing element.

Figure 19A:
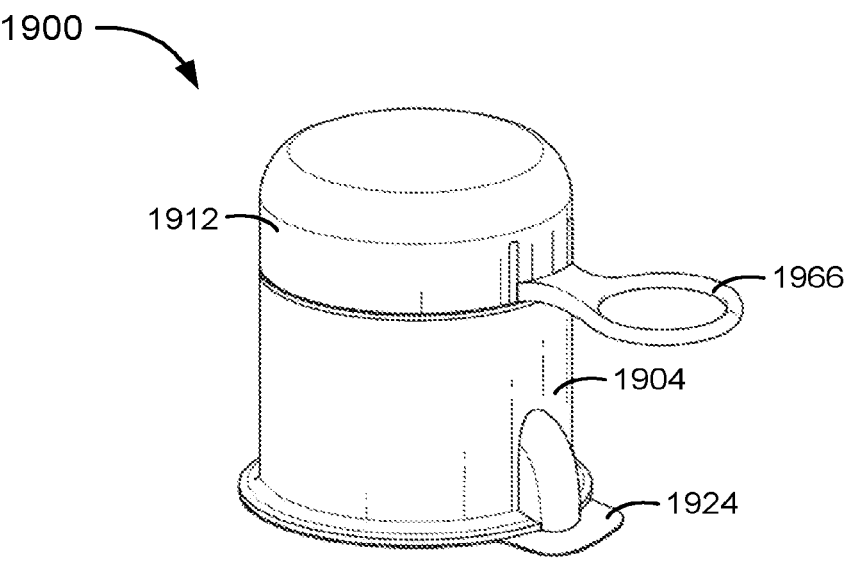
FIG. 19A illustrates a perspective view of an applicator for applying an on-skin assembly to skin of a host including a frangible cap configured to seal an actuation member and a peelable layer configured to seal a distal opening in a housing, in accordance with some embodiments.
Figure 19B:
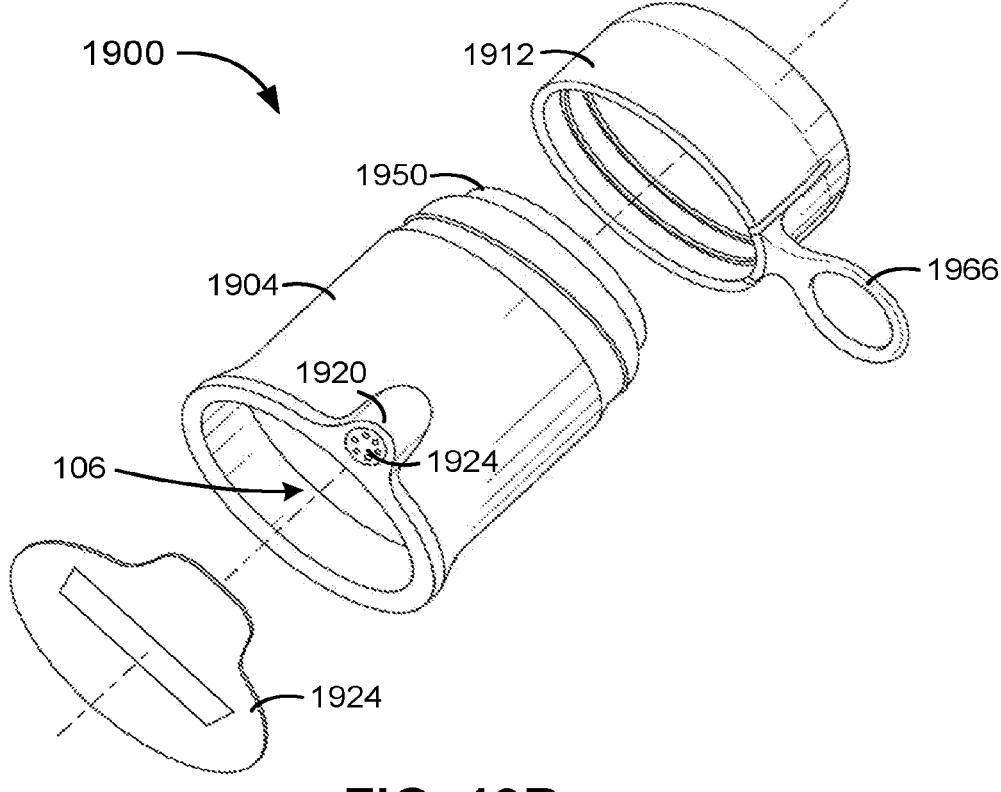
FIG. 19B is a partially exploded view of the applicator of FIG. 19A.

FIG. 19A illustrates a perspective view of an applicator 1900 for applying on-skin assembly 102 to skin of a host including a frangible cap 1912 configured to seal an actuation member 1950 and a peelable layer 1924 configured to seal a distal aperture 106 in a housing 1904, in accordance with some embodiments. FIG. 19B is a partially exploded view of applicator 1900 of FIG. 19A. Applicator 1900 may comprise substantially the same components as applicator 1800 of FIGS. 18A and 18B, however, omitting tamper-evident twist-off collar 1830, threads 1808 and 1814, and replacing removable cap 1812 with frangible cap 1912 and pull tab 1966. For example, housing 1904, aperture 106, vent 1962, actuation member 1950 and peelable layer 1924 correspond with housing 1804, aperture 106, vent 1862, actuation member 1850 and peelable layer 1824, respectively. Furthermore, applicator 1900 may further include a protrusion 1920 configured to inhibit applicator 1900 from rolling, as previously described in connection with FIG. 2.

Frangible cap 1912 is configured to couple with a proximal portion of housing 1904. In some embodiments, frangible cap 1912 comprises pull tab 1966. Frangible cap 1912 is configured to be removed by pulling on pull tab 1966, thereby releasing frangible cap 1912. In this way, frangible cap 1912, and peelable layer 1924 may form a sealing element configured to provide a sterile barrier and/or a vapor barrier between an internal environment and an external environment of housing 1904. Frangible cap 1912 further provides a tamper indicator for a host using applicator 1900 such that if frangible cap 1912 is broken, tampering would be visually evident to a user. Frangible cap 1912 additionally provides premature deployment prevention and drop protection features in that, until removed, it prevents access to actuation member 1950.

Figure 34A:
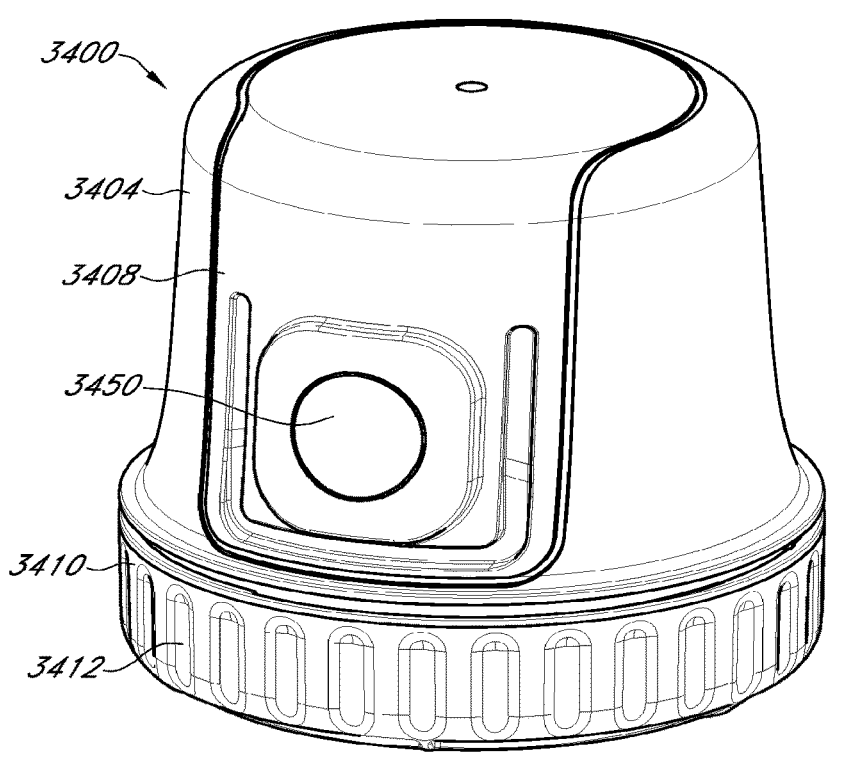
FIG. 34A illustrates a perspective view of an applicator for applying an on-skin assembly to skin of a host including a removable cap configured to seal the applicator, in accordance with some embodiments.

FIG. 34A illustrates a perspective view of an applicator 3400 for applying on-skin assembly 102 to skin of a host including a removable cap 3410 configured to seal applicator 3400, in accordance with some embodiments. Applicator 3400 may include a housing 3404 having a main portion 3408. Main portion 3408 may be overmolded with housing 3404. In some embodiments, main portion 3408 is overmolded with actuation member 3450. Further, main portion 3408 may be comprised of, for example, rubber, silicone, or any other flexible, soft material. Main portion 3408 may provide shock protection as well as grip to a user. Additionally, main portion 3408 may comprise an elastomeric material configured to absorb at least a portion of energy imparted to applicator 3400 when dropped.

Applicator 3400 may include an actuation member 3450 (e.g. push button) that is formed integral with housing 3404. Actuation member 3450 may be configured to be pressed by a user to activate an internal insertion assembly 3470 (see FIG. 34B). In some embodiments, after removal of removable cap 3410, housing 3404 is configured to be pressed down against a surface (e.g. skin of a user) to unlock actuation member 3450. Housing 3404 may be actuated along an inner housing 3406 to align actuation member 3450 with a trigger arm of insertion assembly 3470. Actuation member 3450 may then be pushed in a lateral direction to actuate trigger arm and activate insertion assembly 3470.

Figure 34B:
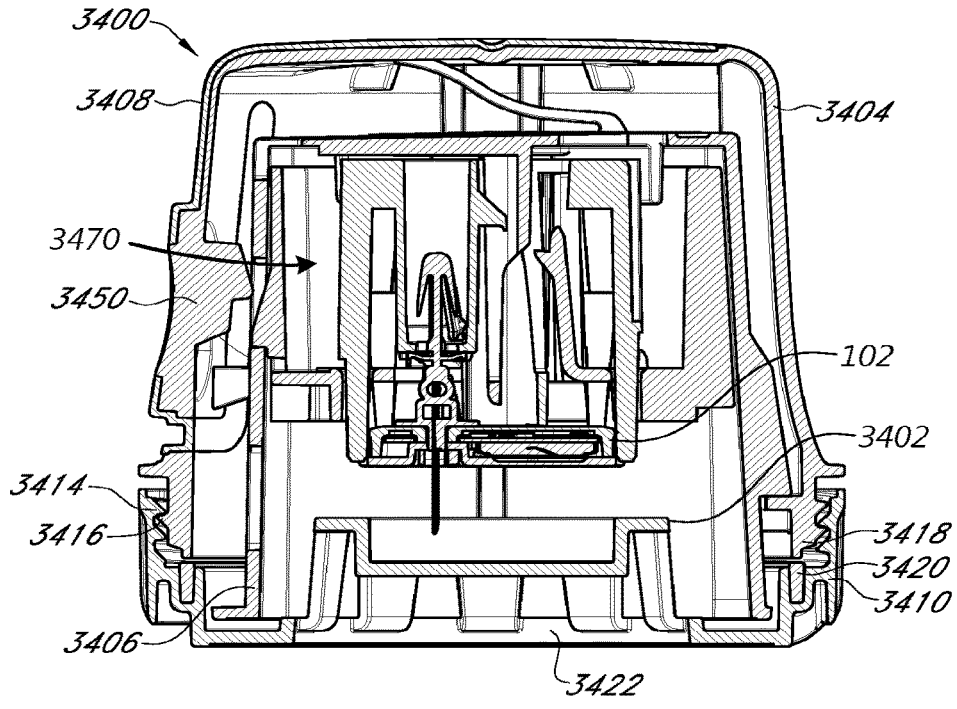
FIG. 34B is a cross-sectional view of the applicator of FIG. 34A.

As shown in FIG. 34B, applicator, removable cap 3410 may be secured to housing 3404 by interlocking cap threads 3414 and corresponding threads 3416. Furthermore, a seal 3420 may be configured to be compressed between removable cap 3410 and a distal portion 3418 of housing 3404. Seal 3420 may be comprised of an elastomer and/or other compressible materials. Seal 3420 may be configured to provide a gas barrier and/or vapor barrier between applicator 3400 and the surrounding environment. Although not shown, removable cap 3410 may be detached from housing 3404 by twisting removable cap 3410 with respect to housing 3404, or vice versa, until cap threads 3414 and corresponding threads 3416 of housing 3404 are no longer mated with each other. Removable cap 3410 may include grooves 3412 for improved grip by the user during attachment or detachment of cap 3410 to housing 3404.

Figure 34C:
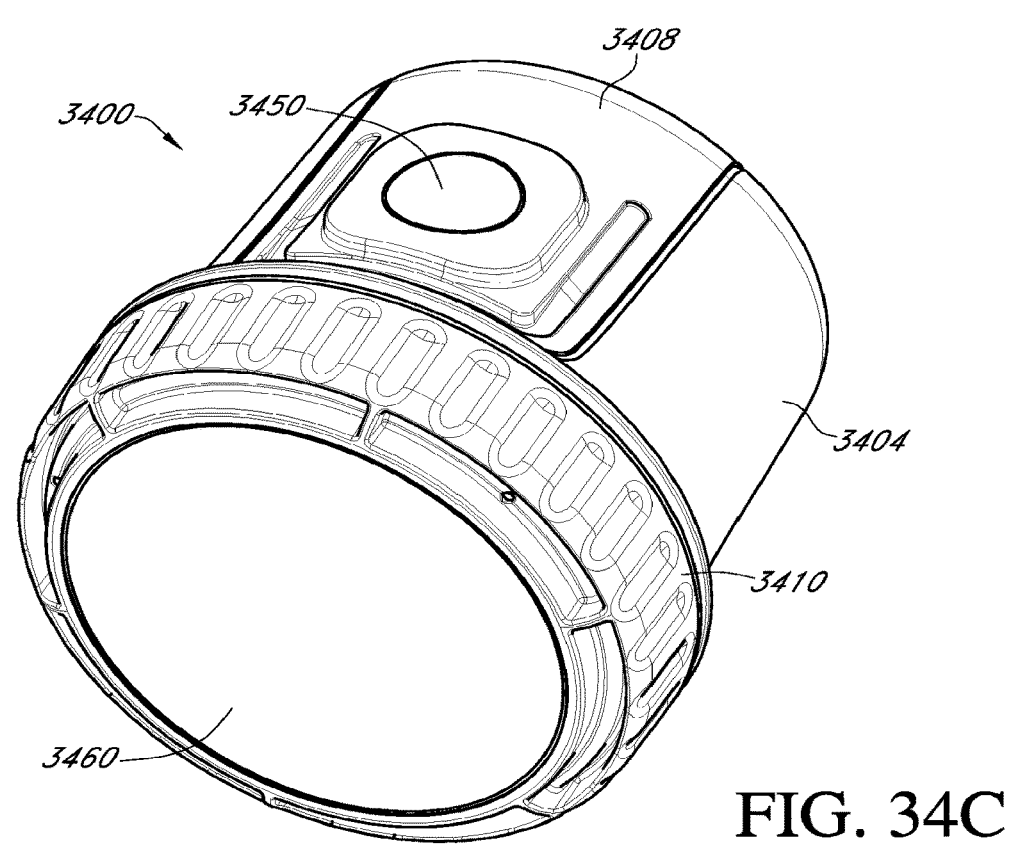
FIG. 34C is a perspective view of the bottom of the applicator of FIG. 34A with a bottom layer.
Figure 34D:
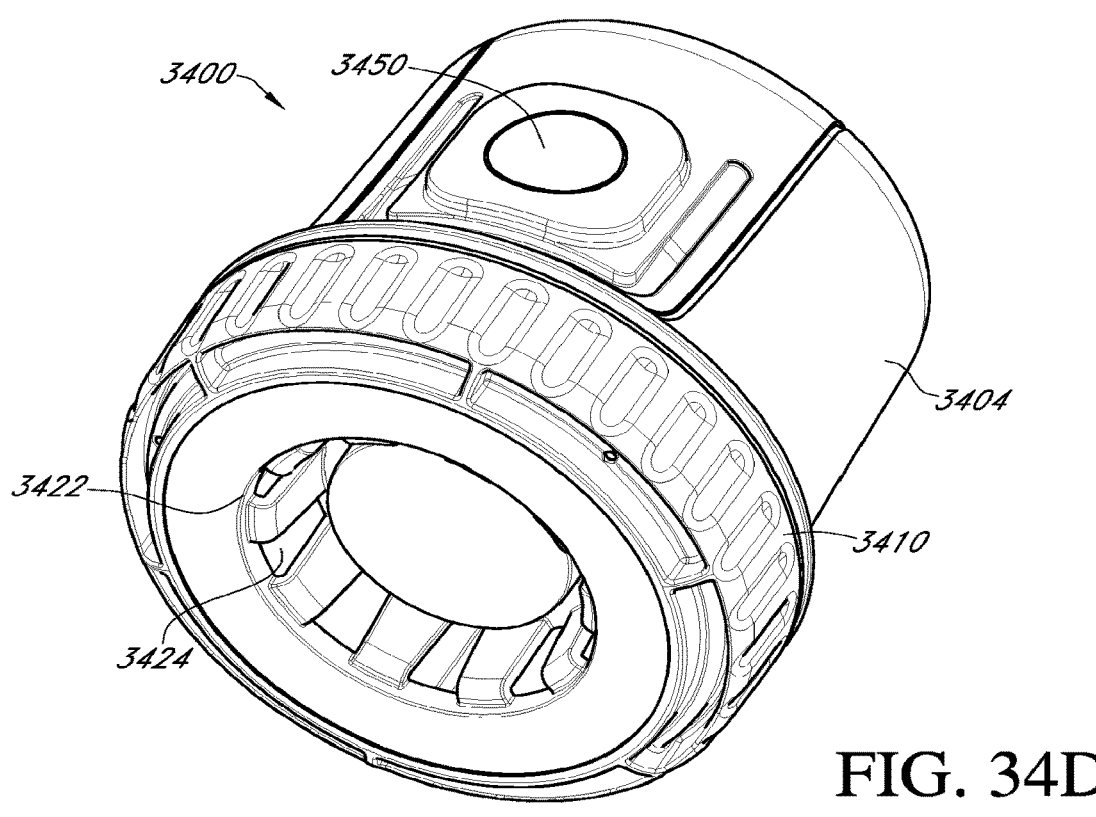
FIG. 34D is a perspective view of the bottom of the applicator of FIG. 34A without a bottom layer.

As shown in FIG. 34C, a bottom layer 3460 may be coupled to a distal end of removable cap 3410 and seal an aperture 3422 of removable cap 3410. Bottom layer 3460 may be similar to first layer 122 of FIG. 1A. Bottom layer 3460 may be permeable to a sterilizing gas (e.g., ethylene oxide, or ETO). Moreover, bottom layer 3460 may comprise Tyvek® material, although any other material permeable to a sterilizing gas may be utilized. Bottom layer 3460 may allow for the ingress and egress of a sterilizing gas through removable cap 3410 during manufacture. As shown in FIG. 34D, without bottom layer 3460, removable cap 3410 may include an open aperture 3422. Furthermore, removable cap 3410 may include at least one aperture channel 3424. In some embodiments, removable cap 3410 includes at least two aperture channels 3424. In some embodiments, removable cap 3410 includes at least three aperture channels 3424. In some embodiments, removable cap 3410 includes at least four aperture channels 3424. In some embodiments, removable cap 3410 includes at least 6 aperture channels 3424. Each aperture channels 3424 may be configured to allow for a sterilizing gas to ingress into housing 3404. In some embodiments, aperture channels 3424 are formed within a platform 3402. Platform 3402 may be a raised platform from the distal end of removable cap 3410. Platform 3402 may be configured to be spaced a certain distance from an on-skin sensor assembly 102. Aperture channels 3424 may be open slots spaced equidistantly along the circumference of platform 3402.

As such, sterilizing gas from a surrounding environment of applicator 3400 may ingress through bottom layer 3460, pass through aperture channels 3424, and then ingress into the internal components of applicator 3400. An opposite process can occur for egress of the sterilizing gas from within applicator 3400, through aperture channels 3424, through bottom layer 3460, and out into a surrounding environment of applicator 3400.

Figures 35A, 35B:
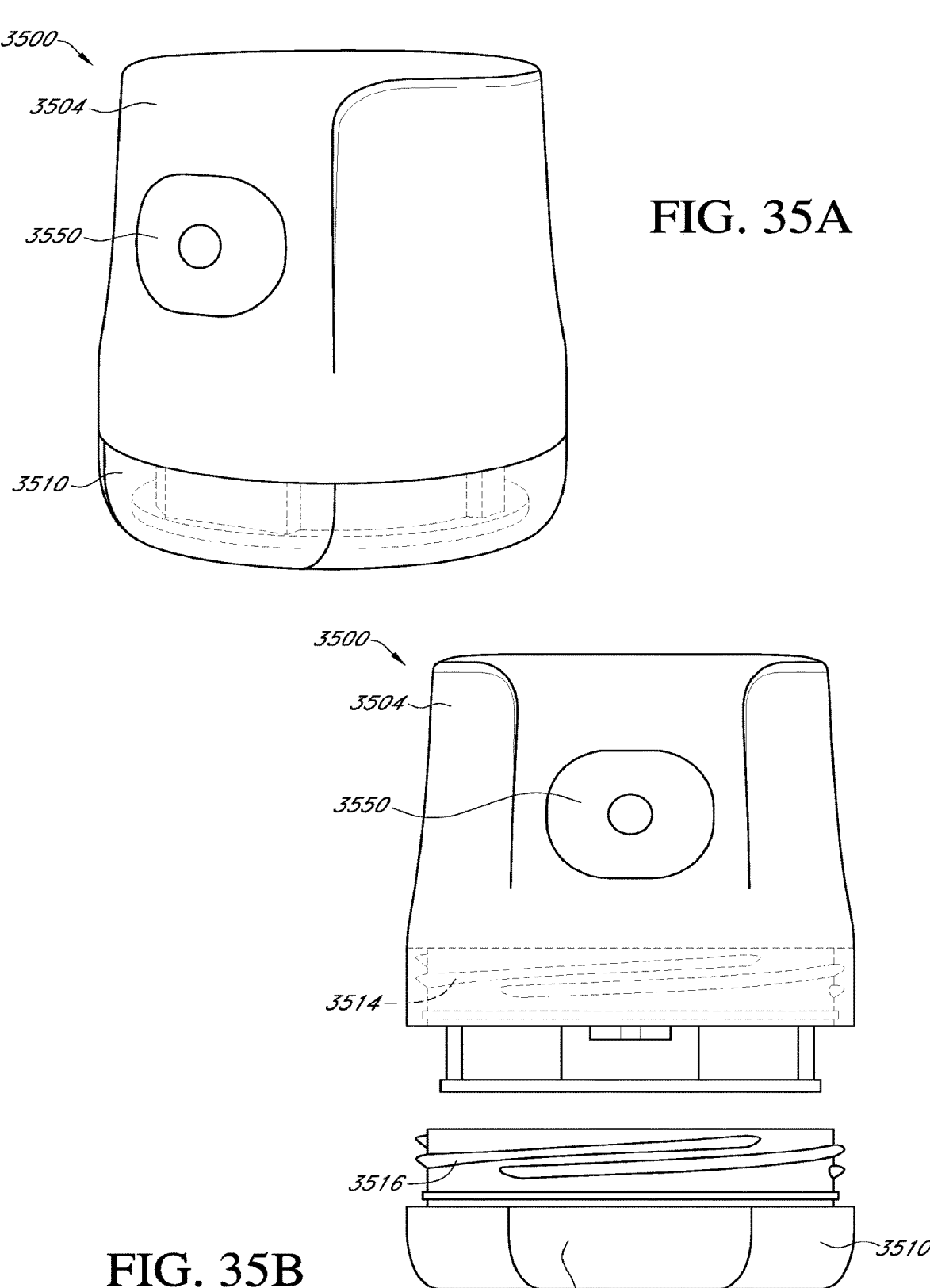
FIG. 35A illustrates a perspective view of an applicator for applying an on-skin assembly to skin of a host including a removable cap configured to seal the applicator, in accordance with some embodiments.
FIG. 35B illustrates a partially exploded view of the applicator of FIG. 35A.

FIG. 35A illustrates a perspective view of an applicator 3500 including a removable cap 3510. Applicator 3500 may also include a housing 3504 and an actuation member 3550. Removable cap 3510 may be removably attached to housing 3504. As shown in FIG. 35B, housing 3504 includes internal threads 3514 and removable cap 3510 includes external threads 3516. In such embodiments, internal threads 3514 may be located in the interior of housing 3504 and thus hidden or partially obscured from the user after the user removes removable cap 3510 from housing 3504. In other embodiments, housing 3504 may include exterior threads that are not contained within the interior of housing 3504 and instead protrude from an exposed lower body of housing 3504. In such embodiments, removable cap 3510 may include corresponding internal threads that are hidden or partially obscured from the user. In some embodiments, removable cap 3510 may include at least one groove 3512 for improved grip by the user during attachment or detachment of cap 3510 to housing 3504.

Embodiments Including Multiple Peelable Layers

Figure 20A:
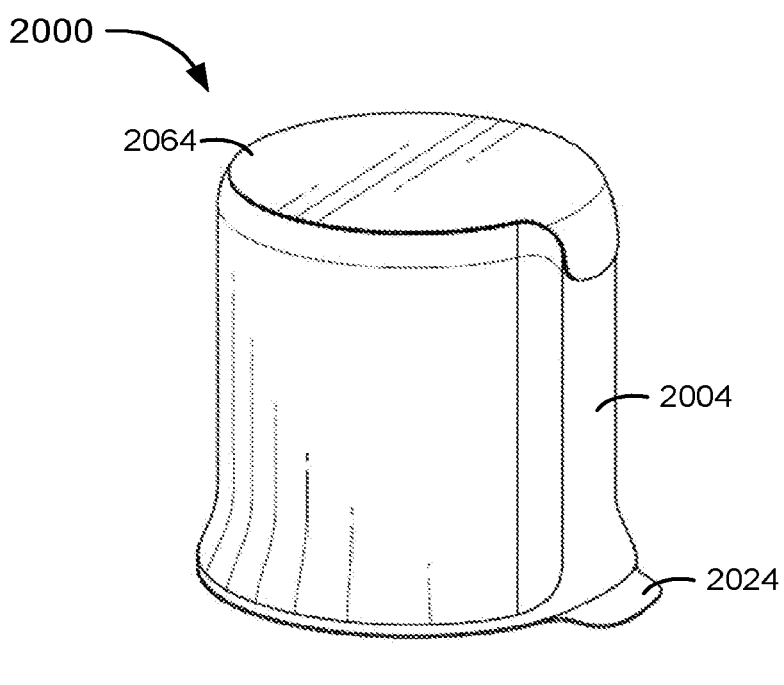
FIG. 20A illustrates a perspective view of an applicator for applying an on-skin assembly to skin of a host including a first peelable layer configured to seal a distal opening in a housing and a second peelable layer configured to seal an actuation member disposed in a proximal opening in the housing, in accordance with some embodiments.
Figure 20B:
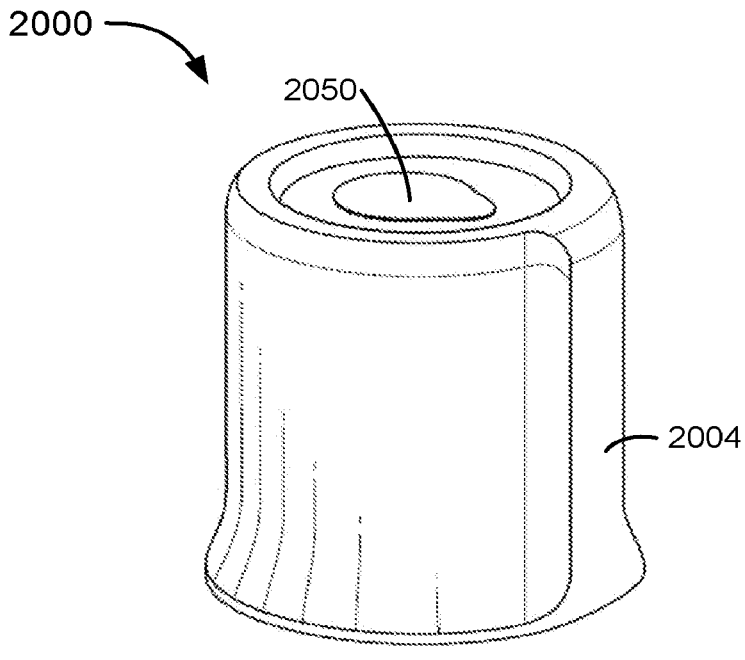
FIG. 20B illustrates the actuation member of the applicator of FIG. 20A.

Some embodiments can include one or more peelable layers (e.g., sheets of material which are coupled (e.g. adhesively, heat staking) to a portion of the applicator and easily removable from the housing by a peeling action) which is coupled to, or integrally formed with, a removable cap. FIG. 20A illustrates a perspective view of an applicator 2000 for applying on-skin assembly 102 to skin of a host including a first peelable layer 2024 configured to seal a distal aperture 106 in a housing 2004 and a second peelable layer 2064 configured to seal an actuation member 2050 disposed in a proximal opening in the housing, in accordance with some embodiments. FIG. 20B illustrates the actuation member of the applicator of FIG. 20A in each of a pre-activated position and an activated position. Applicator 2000 comprises a housing 2004 configured to house insertion assembly 118 (not shown) and comprising aperture 106 (not shown) through which on-skin assembly 102 can pass. Applicator 2000 further comprises actuation member 2050 disposed on a proximal (i.e., top) of housing 2004 and configured to, upon activation, cause insertion assembly 118 to insert at least a portion of on-skin assembly into the skin of a host. In some embodiments actuation member 2050 is recessed into the proximal portion of housing 2004. Applicator 200 further comprise first peelable layer 2024 is configured to seal aperture 106 in housing 2004 and second peelable layer 2064 configured to seal actuation member 2050. Accordingly, first peelable layer 2024 and second peelable layer 2064 may form a sealing element configured to provide a sterile barrier and/or a vapor barrier between an internal and external environment of housing 2004. Applicator 2000 may be readied for use by removing first peelable layer 2024 and second peelable layer 2064. Accordingly, first peelable layer 2024 and second peelable layer 2064 may simultaneously provide a tamper indication and premature deployment prevention feature.

Figures 21A, 21B, 21C:
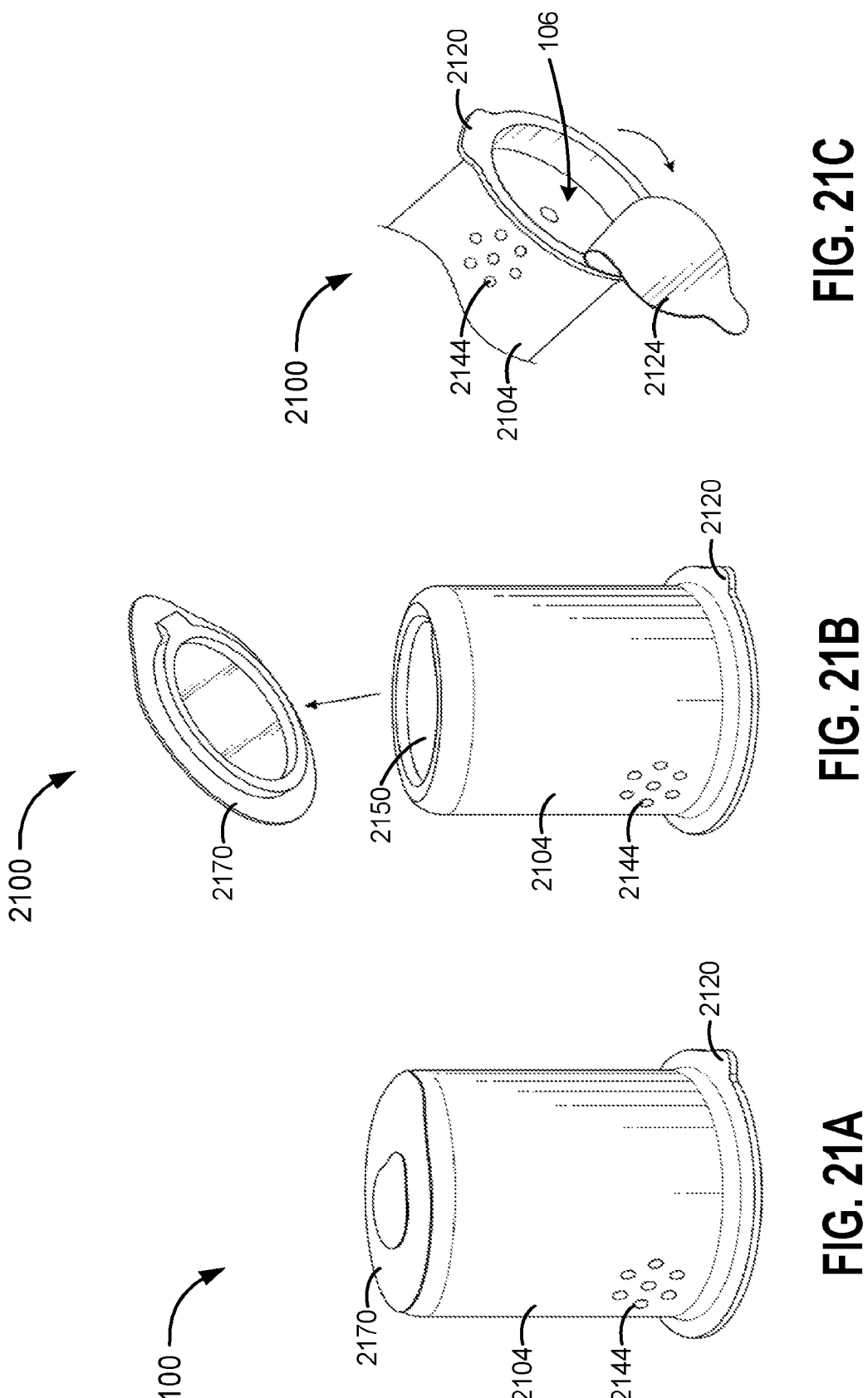
FIG. 21A illustrates a perspective view of another applicator for applying an on-skin assembly to skin of a host including a inset plug configured to seal an actuation member and a peelable layer configured to seal a distal opening in a housing, in accordance with some embodiments.
FIG. 21B is a detail view of the applicator of FIG. 21A having the peelable layer removed.
FIG. 21C is a detail view of the applicator of FIG. 21A having the inset cap removed.

FIG. 21A illustrates another applicator 2100 for applying on-skin assembly 102 to skin of a host including an inset plug 2170 configured to seal an actuation member 2150 and a peelable layer 2124 configured to seal a distal aperture 106 in a housing 2104, in accordance with some embodiments. Applicator 2100 comprises housing 2104 configured to house insertion assembly 118 and comprises an aperture 106 through which on-skin assembly 102 can pass. Applicator 2100 further comprises actuation member 2150 (see FIG. 21C) disposed on a proximal (i.e., top) portion of housing 2104 and configured to, upon activation, cause insertion assembly 118 to insert at least a portion of on-skin assembly into the skin of a host. In some embodiments, actuation member 2150 is recessed into the proximal portion of housing 2104. Applicator 2100 further comprises peelable layer 2124 coupled to at least a portion of housing 2104. For example, peelable layer 2124 is configured to seal aperture 106 (see FIG. 21B). Applicator 2100 further comprises inset plug 2170 configured to seal actuation member 2150. Thus, peelable layer 2124 and inset plug 2170 form a sealing element configured to provide a sterile barrier and/or a vapor barrier between an internal and external environment of housing 2104. Applicator 2100 may further comprise one or more ridges or recesses 2144 configured to provide a tactile indication of grip to the host. In some embodiments, applicator 2100 may further comprise comprises at least one protrusion 2120 configured to inhibit rolling of applicator 2100. Protrusion 2120 may also function as an orientation indicator for the user.

In an alternate embodiment, housing 2104 may be a deformable container capable of flexing inwards and outwards. In such embodiments, a squeezing of housing 2104 may activate an insertion assembly within housing 2104, such as insertion assembly 118 (shown in FIG. 8B). The deformation caused by the squeezing of housing 2104 may decouple a trigger arm or latch (not shown) which can release the insertion assembly. Furthermore, in such embodiments, ridges or recesses 2144 may be activation indicators to notify the user where to squeeze in order to activate and fire the insertion assembly.

As shown more detail by FIGS. 21B and 21C, applicator 2100 may be readied for use by removing peelable layer 2124 and inset cap 2170, thereby exposing aperture 106 and actuation member 2150, respectively. In this way, peelable layer 2124 and/or inset plug 2170 may simultaneously provide at least tamper indication and premature deployment prevention features.

FIG. 21B illustrates applicator 2100 of FIG. 21A having peelable layer 2124 removed. As shown, once peelable layer 2124 is removed aperture 106 is exposed.

FIG. 21C illustrates applicator 2100 of FIG. 21A having inset cap 2170 removed. As shown, once inset cap 2170 is removed actuation member 2150 is exposed and readied for activation.

Figure 22A:
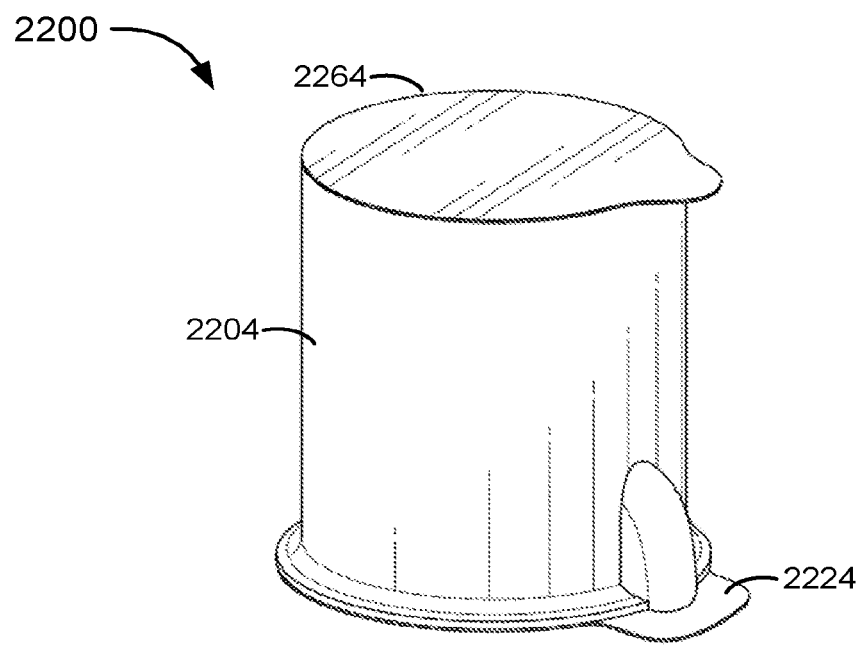
FIG. 22A illustrates a perspective view of an applicator for applying an on-skin assembly to skin of a host including a first peelable layer configured to seal a distal opening in a housing and to seal a vent permeable to a sterilizing gas and a second peelable layer configured to seal an actuation member disposed in a proximal opening in the housing, in accordance with some embodiments.
Figure 22B:
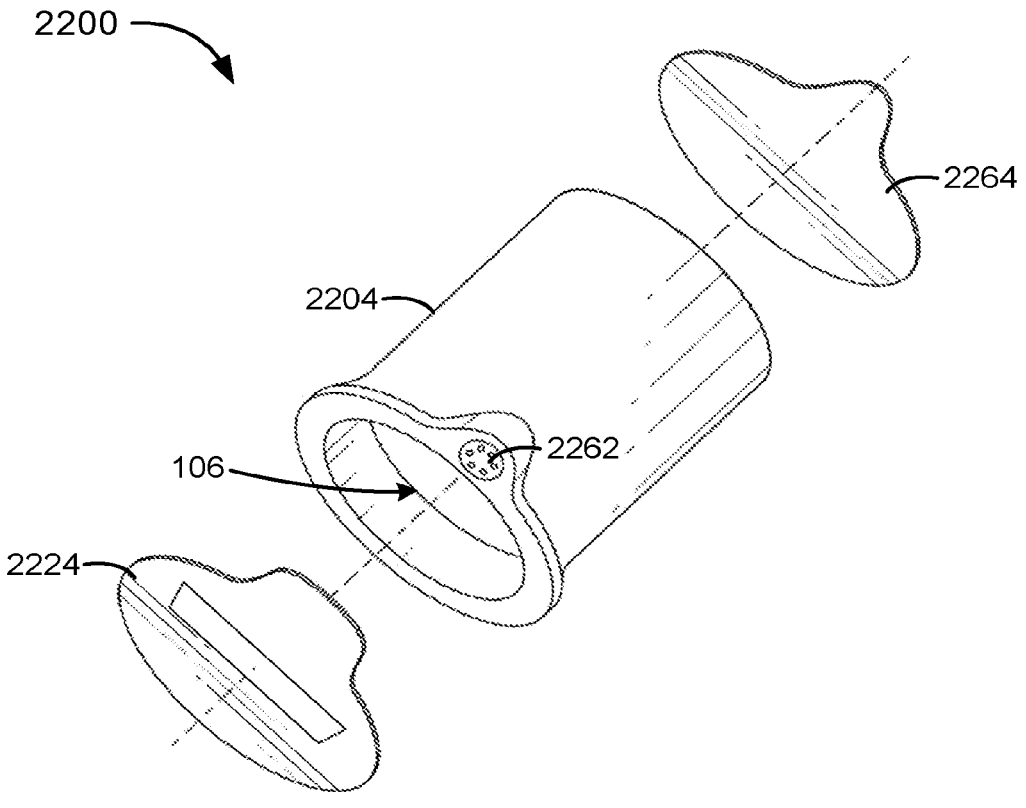
FIG. 22B is a partially exploded view of the applicator of FIG. 22A.

FIG. 22A illustrates a perspective view of an applicator 2200 for applying on-skin assembly 102 to skin of a host including a first peelable layer 2224 configured to seal a distal aperture 106 in a housing 2204 and to seal a vent 2262 (optional) permeable to a sterilizing gas and a second peelable layer 2264 configured to seal an actuation member (not shown) disposed in a proximal opening in housing 2204, in accordance with some embodiments. FIG. 22B is a partially exploded view of applicator 2200 of FIG. 22A. Applicator 2200 may be substantially the same as applicator 2000 of FIGS. 20A and 20B, except as described below. Applicator 2200 comprises housing 2204, first peelable layer 2224, actuation member (not shown), and second peelable layer 2264, which correspond to housing 2004, first peelable layer 2024, actuation member (not shown), and second peelable layer 2064 of applicator 2000, respectively. Applicator 2200 further comprises vent 2262, which may correspond substantially to vent 1962 as previously described in connection with of FIGS. 19A and 19B. Accordingly, first peelable layer 1924 is configured to seal both aperture 106 of housing 2204 and vent 2262. Of note, vent 2262 being disposed on a distal portion of housing 2204 adjacent to aperture 106 may additionally provide at least one protrusion 2220 configured to inhibit rolling of applicator 2200. Protrusion 2220 may also function as an orientation indicator for the user.

Embodiments Utilizing Protective Cups

Figure 23:
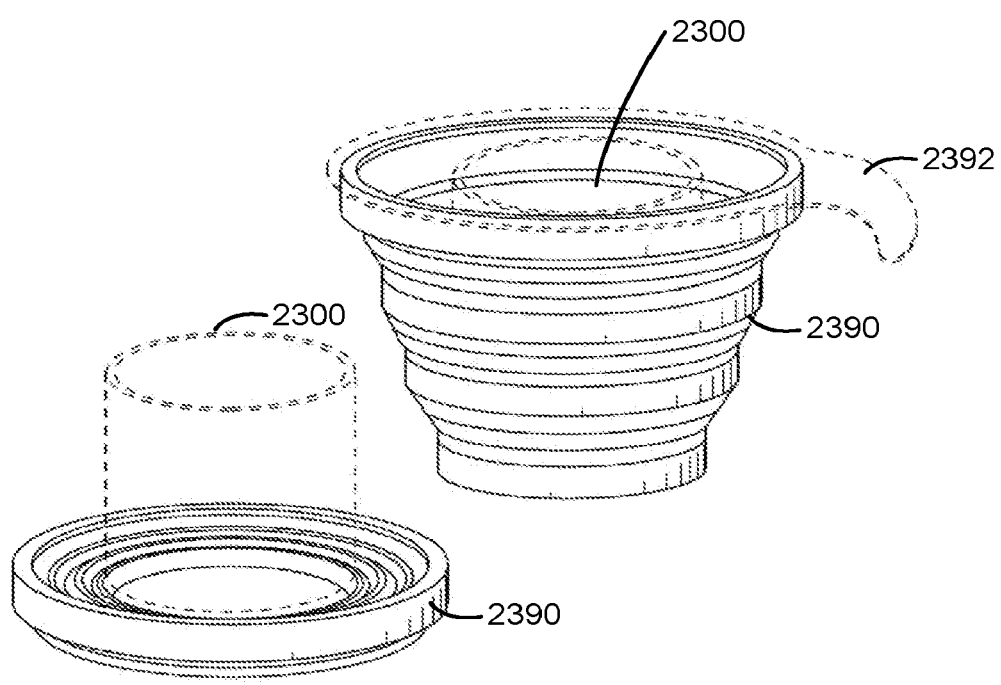
FIG. 23 illustrates a perspective view of an applicator for applying an on-skin assembly to skin of a host configured to fit within a collapsible cup having a removable lid, in accordance with some embodiments.

FIG. 23 illustrates a collapsible cup 2390 having a removable lid 2392 and configured to enclose an applicator 2300 for applying on-skin assembly 102 to skin of a host configured to fit within, in accordance with some embodiments. Collapsible cup 2390 has a removable and/or peelable lid 2392. Collapsible cup 2390 is configured to act as a sealing element that seals applicator 2300 from an environment outside collapsible cup 2390. In some embodiments, collapsible cup 2390 comprises an elastomer. In some embodiments, collapsible cup 2390 is configured to collapse after removal of removable and/or peelable lid 2392. Applicator 2300 may correspond to any applicator, including any described in this detailed description.

Figure 24A:
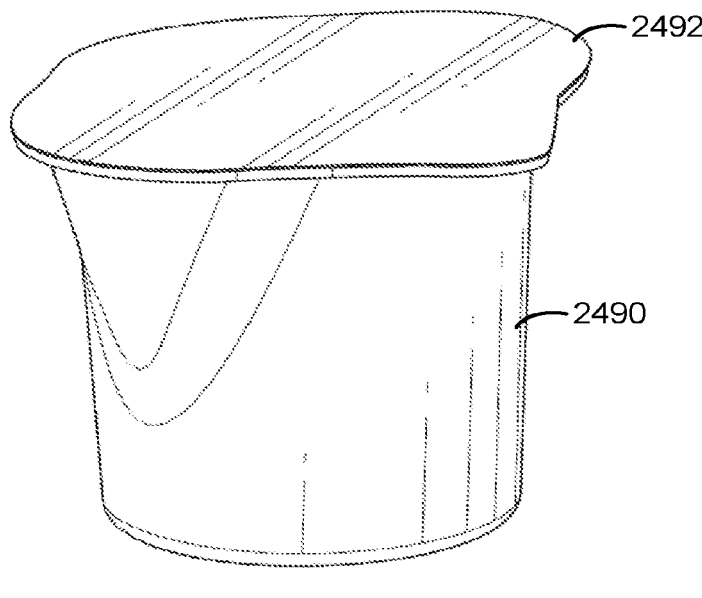
FIG. 24A illustrates a perspective view of a cup having a removable lid and configured to enclose an applicator for applying an on-skin assembly to skin of a host, in accordance with some embodiments.

FIG. 24A illustrates a cup 2490 having a removable lid 2492 and configured to enclose an applicator 2400 for applying on-skin assembly 102 to skin of a host, in accordance with some embodiments. In some embodiments, cup 2390 is in injection molded cup. Cup 2490 is configured to act as a sealing element that seals applicator 2400 from an environment outside cup 2490. Applicator 2400 (see FIG. 24B) may be readied for use by peeling removable lid 2492 from cup 2390 and removing applicator 2400 therefrom. Applicator 2400 may be substituted with any previously described applicator.

Figure 24B:
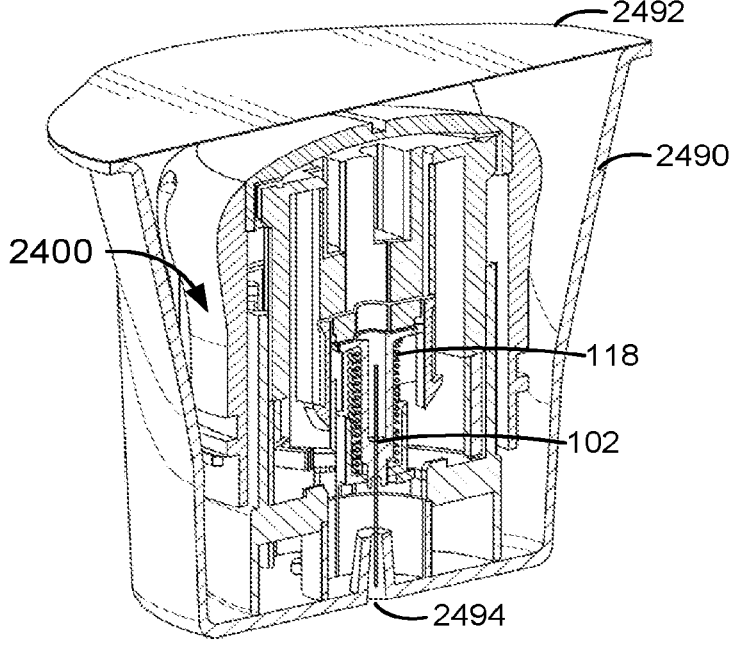
FIG. 24B is a cross-sectional view of the cup and applicator of FIG. 24A.

FIG. 24B is a cutaway view of cup 2490 and applicator 2400 of FIG. 24A. As shown, within cup 2490 is disposed applicator 2400. In some embodiments, cup 2490 may further comprise an on-skin assembly alignment feature 2494. In some embodiments, on-skin alignment feature 2494 may further comprise a needle protection feature in that, by restraining at least lateral movement of the needle of insertion assembly 118, on-skin assembly alignment feature 2494 not only protects the needle from damage or outside contact, it also keeps on-skin assembly 102 in proper alignment.

Actuation Member Alternatives

The present application sets forth a plurality of different applicator embodiments. However, the present application is not limited solely to the isolated embodiments, described. For example, any actuation member of any describe embodiment may be replaced with any other actuation member previously described, as desired. Any actuation member may be used to activate an insertion assembly, such as insertion assembly 118 (not shown). For example, any applicator may alternatively comprise an actuation member disposed on a side of the housing (see FIGS. 1A-6B, 11A, 11B, 13A-17C and 25), an actuation member disposed on a proximal (i.e., top) portion of the housing (see FIGS. 12A, 12B, and 18A-22B), an actuation member that is a cap in and of itself (see FIGS. 7A-10B), an actuation member that arms via depression and activates via pressing of a flexure (see FIG. 9), a common push button, a bistable button (see FIGS. 11A-12B), or any of the above example, however, further permeable to a sterilizing gas (see FIGS. 25A-25B). In some embodiments, any applicator may comprise a plurality of actuation members, in which depression of one or more of the plurality of actuation members may activate an insertion assembly. In some embodiments, depression of at least two actuation members, simultaneously or in sequence, may be required to activate an insertion assembly.

Figure 25A:
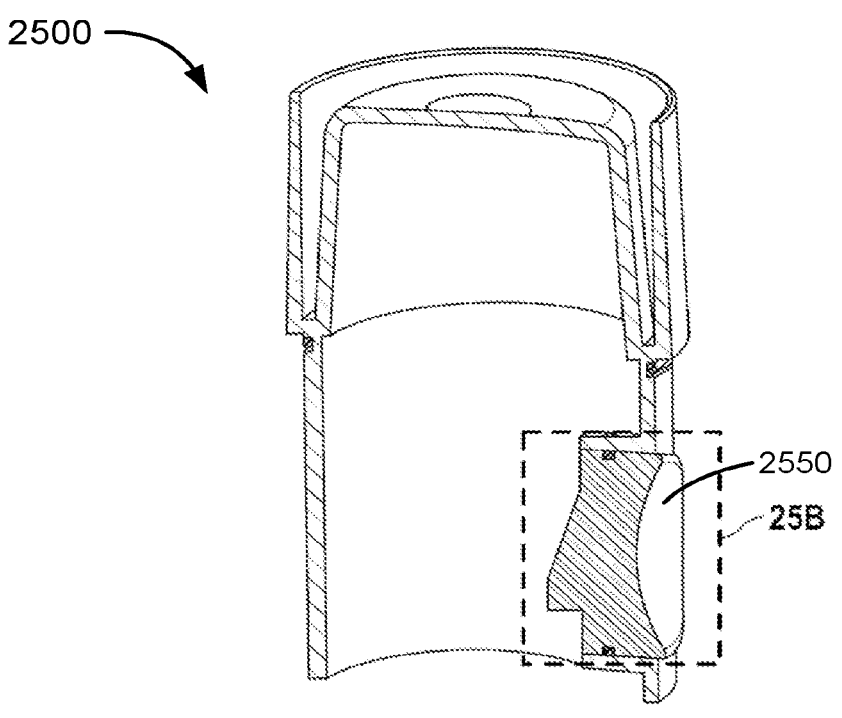
FIG. 25A is a cross-sectional view of an applicator for applying an on-skin assembly to skin of a host including an actuation member that is permeable to a sterilizing gas, in accordance with some embodiments.
Figure 25B:
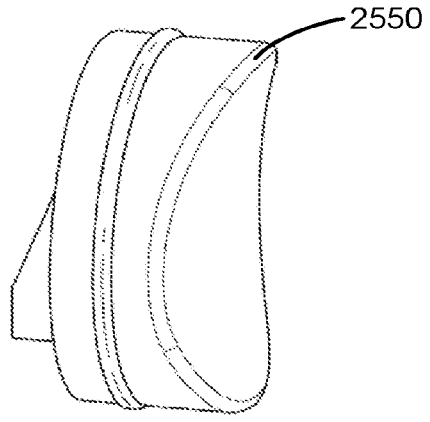
FIG. 25B is a detail view of the actuation member of FIG. 25A.

FIG. 25A is a cutaway view of an applicator 2500 for applying on-skin assembly 102 to skin of a host including an actuation member 2550 that is permeable to a sterilizing gas, in accordance with some embodiments. FIG. 25B is a zoomed view of the actuation member of FIG. 25A. Applicator 2500 comprises an actuation member 2550, which itself comprises a material that is permeable to a sterilizing gas, for example, Porex®. The structure of applicator 2500 is not of importance here and, thus, applicator 2500 may correspond to any applicator, including any described herein. Thus, any applicator described herein may have its actuation member replaced with actuation member 2550, e.g., replaced with an actuation member that is permeable to a sterilizing gas. In such embodiments, any vent may be omitted as the actuation member may also function as the vent.

Bulk Manufacturing, Sterilizing, and/or Sealing of Applicators

As previously stated, it may be desirable to be able to manufacture, sterilize and/or seal applicators in bulk. This would not only reduce the per-unit cost of manufacture, it would potentially decrease the cost to consumers of the applicators. Accordingly, below are described a few embodiments that may allow for bulk manufacturing, sterilizing and/or sealing of multiple applicators simultaneously.

Figure 26A:
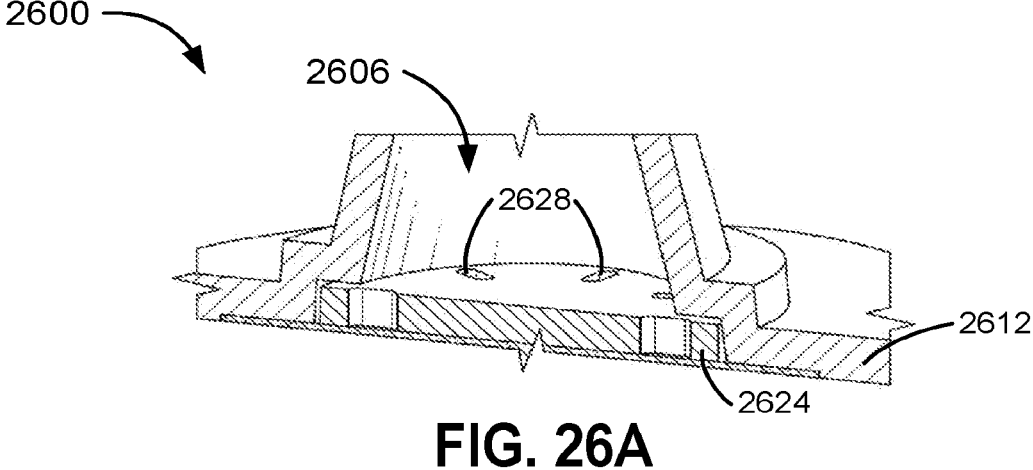
FIG. 26A is a cross-sectional view of a soluble moisture barrier having a plurality of perforations for an applicator for applying an on-skin assembly to skin of a host, in accordance with some embodiments.
Figure 26B:
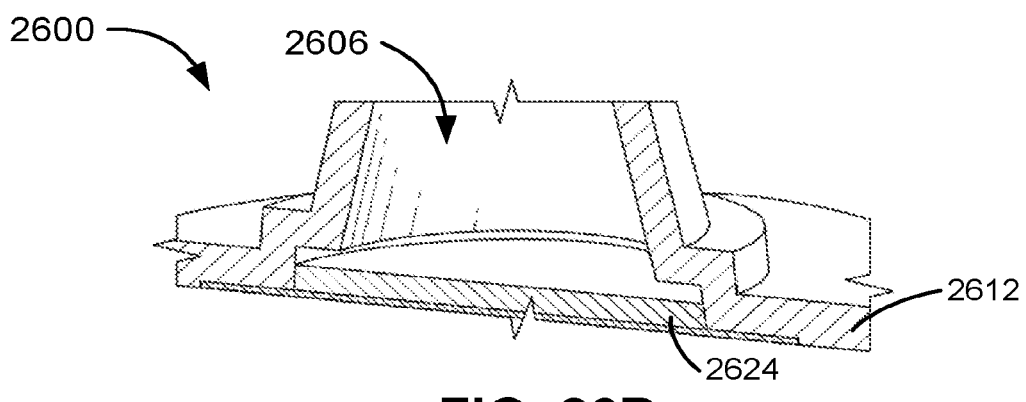
FIG. 26B is a cross-sectional view of the soluble moisture barrier of FIG. 26A after heating such that the moisture barrier has melted and the plurality of perforations are sealed.

FIG. 26A is a cutaway view of a soluble moisture barrier 2624 having a plurality of perforations 2628 for an applicator 2600 for applying on-skin assembly 102 to skin of a host, in accordance with some embodiments. For example, soluble moisture barrier 2624 having one or more perforations 2628 may be utilized as a sealing element and may be disposed over an opening 2626 in a removable cap 2612, for example, as previously described in connection with at least FIGS. 1A-1C and 3A-3C. The applicator 2600 may be subjected to a sterilizing gas, which may ingress and then egress through one or more perforations 2628, thereby sterilizing the components within applicator 2600. Once sterilization is complete, soluble moisture barrier 2624 may be subjected to a temperature sufficient to at least partially dissolve or reflow moisture barrier material 2624 which can seal perforations 2628, as shown in FIG. 26B. Thus, in one state, soluble moisture barrier 2624 acts as a vent to allow for sterilization of applicator 2600, and in another state, soluble moisture barrier 2624 acts as a seal for applicator 2600.

FIG. 26B is a cutaway view of soluble moisture barrier 2624 of FIG. 26A after heating such that soluble moisture barrier 2624 has cooled down and solidified. Soluble moisture barrier 2624 is configured to redistribute itself in a form in which plurality of perforations 2628 are closed and sealed. Because the operative transforming method is application of heat sufficient to melt soluble moisture barrier material 2624, bulk sterilization and moisture sealing of a plurality of applicators may be achieved without direct contact with components.

Figure 27A:
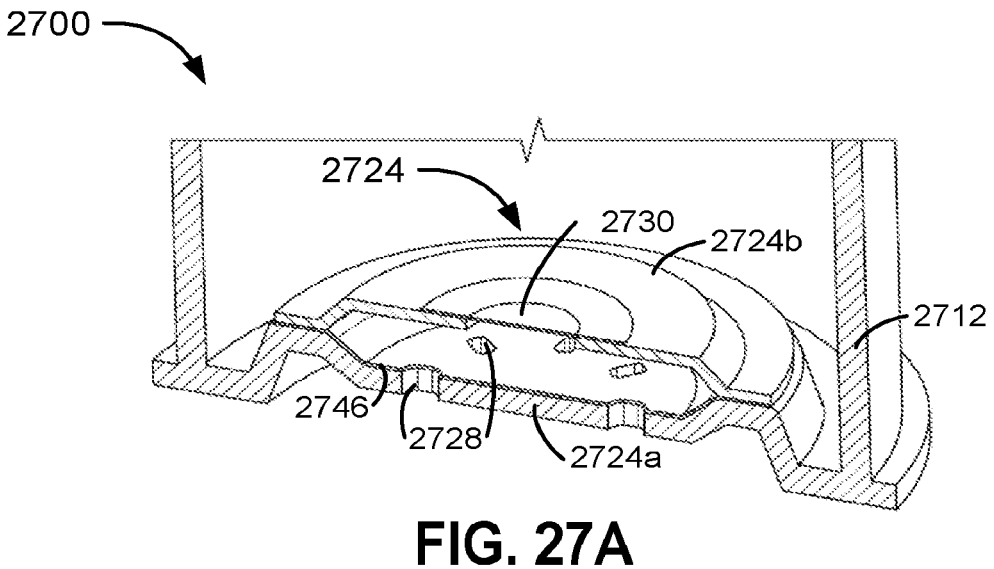
FIG. 27A is a cross-sectional view of a moisture barrier including an elastomeric layer having a portion permeable to a sterilizing gas and a perforated layer configured to pass a permeable gas when the elastomeric layer and the perforated layer are in a first orientation with respect to each other, in accordance with some embodiments.

FIG. 27A is a cutaway view of a moisture barrier 2724 including an elastomeric layer 2724*b* and a perforated layer 2724*a*, in accordance with some embodiments. Moisture barrier 2724 may be utilized as a sealing element and may be integral to a removable cap 2712, for example, as previously described in connection with any previous figure illustrating a removable cap. Perforated layer 2724*a* may be considered a first portion of a sealing element and may comprise a plurality of perforations 2728 and an adhesive layer 2746 disposed on a first side of perforated layer 2724*a*. Elastomeric layer 2724*b* may be considered a second portion of the sealing element and may comprise a portion permeable to a sterilizing gas. Elastomeric layer 2724*b* is disposed adjacent to the first side of perforated layer 2724*a*. Elastomeric layer 2724*b* is configurable in a first configuration where elastomeric layer 2724*b* is spatially separated from perforated layer 2724*a*, providing a pathway for a sterilizing pass to pass through the plurality of perforations 2729 and the portion of elastomeric layer 2724*a* permeable to the sterilizing gas. Elastomeric layer 2724*b* may transition to a second configuration where elastomeric layer 2724*b* is adhered to perforated layer 2724*a* via adhesive layer 2746, removing the pathway for the sterilizing gas and causing moisture barrier 2724 to be impermeable to the sterilizing gas. In some other embodiments, adhesive layer 2746 may not be included, and elastomeric layer 2724*b* may be drawn against perforated layer 2724*a* without the need for adherence, thereby sealing the applicator. FIG. 27A illustrates the first configuration.

Figure 27B:
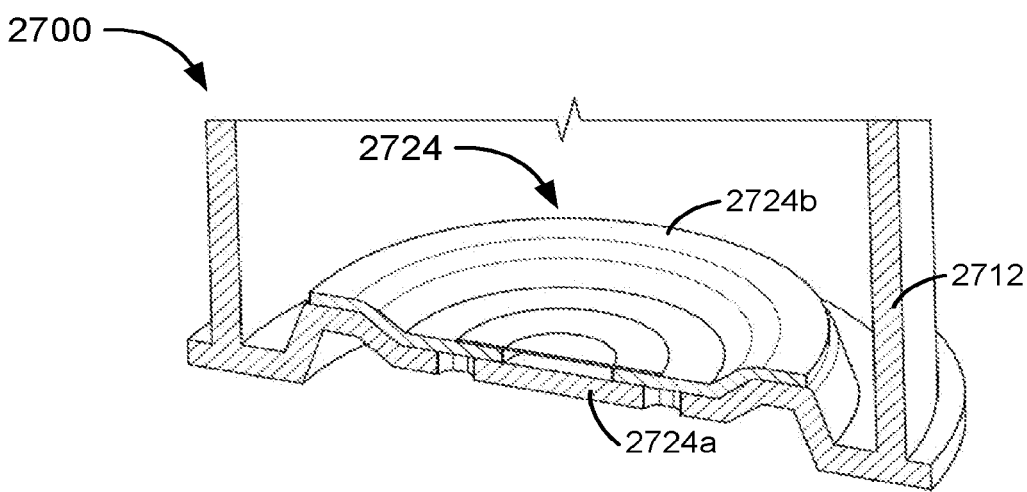
FIG. 27B is a cross-sectional view of the moisture barrier of FIG. 27A illustrating the elastomeric layer and the perforated layer in a second orientation with respect to each other such that the moisture barrier is impermeable to the sterilizing gas and to moisture, in accordance with some embodiments.

As shown in FIG. 27A, applicator 2700 may be subjected to a sterilizing gas, which may ingress and then egress through plurality of perforations 2728 in perforated layer 2724*a* and through a transmissive layer 2730 (e.g., Tyvek®) permeable to the sterilizing gas, thereby sterilizing the components within applicator 2700. Once sterilization is complete, applicator 2700 may be subjected to a partial vacuum, thereby creating a pressure gradient sufficient to transition elastomeric layer 2724*b* from the first configuration to the second configuration. Due to the pressure gradient, elastomeric layer 2724*b* is drawn against perforated layer 2427*a* which seals moisture barrier 2724 from sterilizing gas and moisture, as shown in FIG. 27B. Generically, this concept covers any design that utilizes pressure gradient to actuate a valve that can be closed after gaseous sterilization (e.g. Ethylene Oxide sterilization). For example, another embodiment may include an elastomeric stopper that is configured to move to close air/vapor passage when a vacuum of a sufficient flow rate is applied.

FIG. 27B is a cutaway view of moisture barrier 2724 of FIG. 27A illustrating elastomeric layer 2724*b* and perforated layer 2724*a* in the second orientation such that the moisture barrier is impermeable to the sterilizing gas and to moisture, in accordance with some embodiments. Because the operative transforming method is the application of a partial vacuum sufficient to actuate elastomeric layer 2724*b* from the first configuration to the second configuration, batch sterilization and/or vapor (e.g. water vapor) sealing of a plurality of applicators may be achieved simultaneously by subjecting a plurality of applicators to the partial vacuum simultaneously. This may aid in high efficiency sterilization of a plurality of applicators.

Figure 28A:
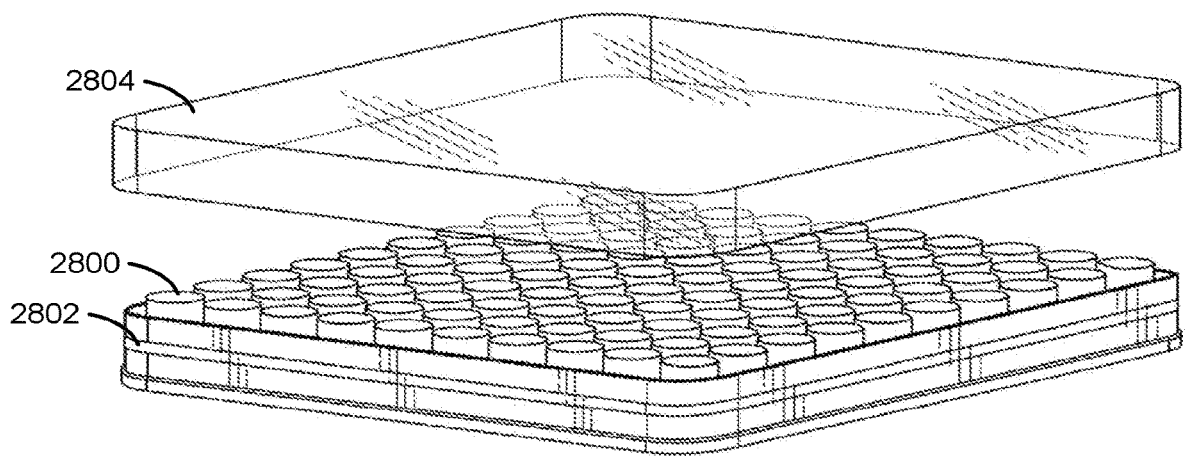
FIG. 28A illustrates a perspective view of a tray configured to hold a plurality of applicators for bulk sterilization and moisture barrier sealing, in accordance with some embodiments.

FIG. 28A illustrates a tray 2802 configured to hold a plurality of applicators 2800 for bulk sterilization and moisture barrier sealing, in accordance with some embodiments. The plurality of applicators 2800 may each, for example, have a structure similar to that described in connection with FIGS. 27A and 27B except wherein elastomeric layer 2724*b* is disposed on an outside of perforated layer 2724*a*. In such embodiments, elastomeric layer 2724*b* would be in the first configuration as previously described. The plurality of applicators 2800 may be disposed on tray 2802.

As shown in FIG. 28A, applicators 2800 may be subjected to a sterilizing gas, which may ingress and then egress through plurality of perforations 2728 in perforated layer 2724*a* and through the transmissive layer 2730 (e.g., Tyvek®, see FIGS. 27A-B) of elastomeric layer 2724*b* permeable to the sterilizing gas, thereby sterilizing the components within each of the plurality of applicators 2800. Once sterilization is complete, a force applicator 2804 may be applied to the plurality of applicators 2800 subjecting them to a force sufficient to transition elastomeric layer 2824*b* in each of the plurality of applicators 2800 from the first configuration to the second configuration, thereby rendering moisture barrier 2824 impermeable to the sterilizing gas and to moisture. Such a transition is as shown in FIG. 28B.

Figure 28B:
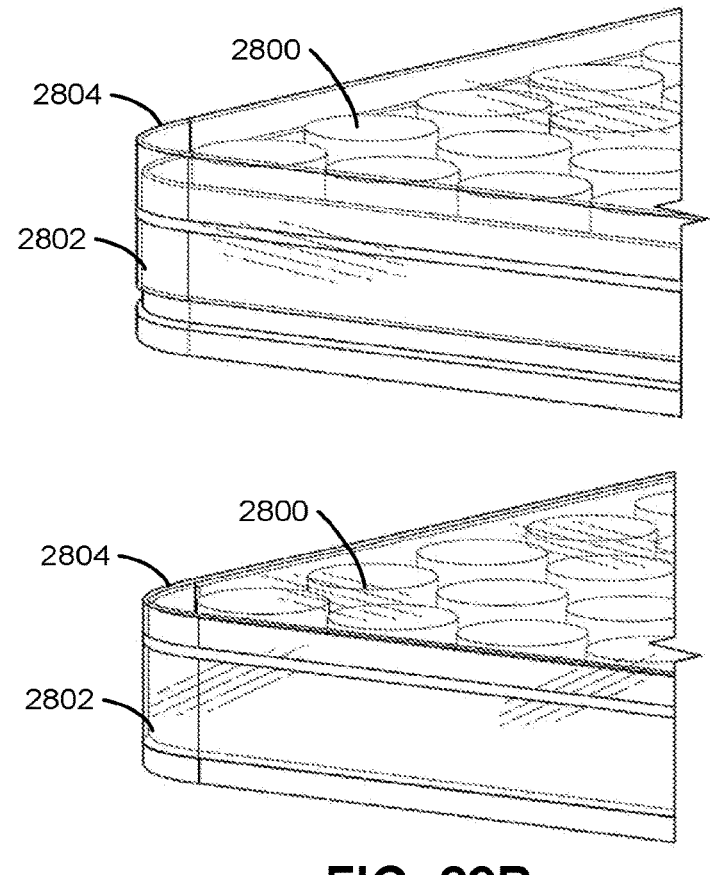
FIG. 28B is a detail view of the tray of FIG. 28A illustrating each applicator in a first configuration permeable to a sterilizing gas, and a second configuration impermeable to the sterilizing gas and to moisture.

FIG. 28B is a zoomed view of tray 2802 of FIG. 28A illustrating each of the plurality of applicators 2800 in the first configuration, permeable to a sterilizing gas, and the second configuration impermeable to the sterilizing gas and to moisture. Because the operative transforming method is application of a force sufficient to actuate each applicator's elastomeric layer 2724*b* from the first configuration to the second configuration, batch sterilization and/or vapor sealing of a plurality of applicators may be achieved simultaneously by subjecting a plurality of applicators to the physical force simultaneously via force applicator 2804.

Figure 29:
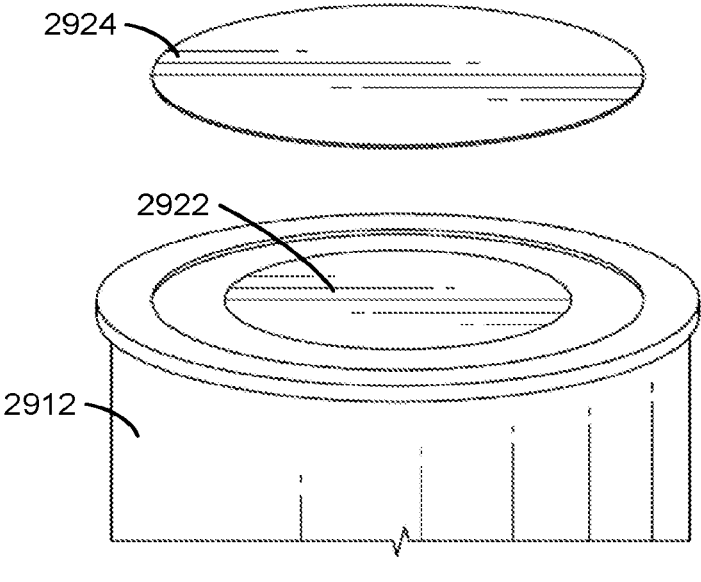
FIG. 29 is an exploded perspective view of a sealing element comprising a first layer permeable to a sterilizing gas and a second layer impermeable to the sterilizing gas and moisture, in accordance with some embodiments.

FIG. 29 is an exploded view of a sealing element comprising a first layer 2922 permeable to a sterilizing gas and a second layer 2924 impermeable to the sterilizing gas and moisture, in accordance with some embodiments. The sealing element may be integral to a removable cap 2912, for example, as previously described in connection with any previous figure illustrating a removable cap.

First layer 2922 may comprise Tyvek®, although any other material permeable to a sterilizing gas may be utilized. Application of first layer 2922 to removable cap 2912 may allow for the subsequent ingress and egress of a sterilizing gas during manufacture. Second layer 2924 may comprise a metallic foil, although any other material impermeable to moisture (e.g., water vapor) may be applied, for example, a metallic foil (e.g. aluminum, titanium), a metallic substrate, aluminum oxide coated polymer, parylene, a polymer coated with a metal applied via vapor metallization, silicon dioxide coated polymer, or any material having a moisture vapor transmission rate less than 10 grams/100 in$^2$ or preferably less than 1 grams/100 in$^2$. First layer 2922 and second layer 2924 may seal an opening (not shown) in removable cap 2912. Application of second layer 2924 over first layer 2922 after sterilization may further provide a moisture barrier for applicator 2900. Because second layer 2924 may be applied simultaneously to a plurality of applicators, batch sterilization and/or vapor sealing may be achieved.

Figure 30A:
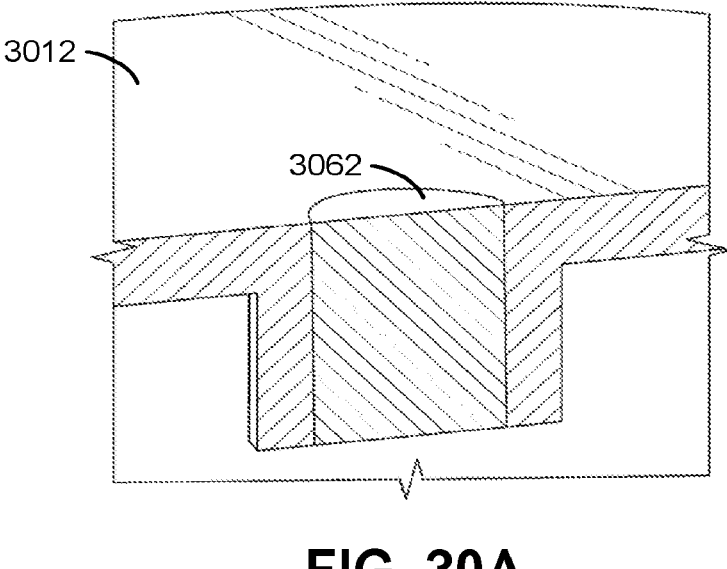
FIG. 30A is a zoomed cross-sectional view of a sealing element comprising a vent including a material permeable to a sterilizing gas, in accordance with some embodiments.

FIG. 30A is a zoomed view of a sealing element comprising a vent 3062 including a material permeable to a sterilizing gas, in accordance with some embodiments. In some embodiments, the material may comprise a porous polymeric component such as Porex®, although any material permeable to a sterilizing gas may be utilized. The sealing element may be integral to a removable cap 3012, for example, as previously described in connection with any previous figure illustrating a removable cap. One or more applicators utilizing the sealing element comprising vent 3062 may be subjected to a sterilizing gas, which may ingress and egress the applicators via vent 3062. Once sterilization is complete, the sealing element comprising vent 3062 may be subjected to a temperature sufficient to form a sintered layer 3063 (see FIG. 30B) in the porous polymeric component of vent 3062.

Figure 30B:
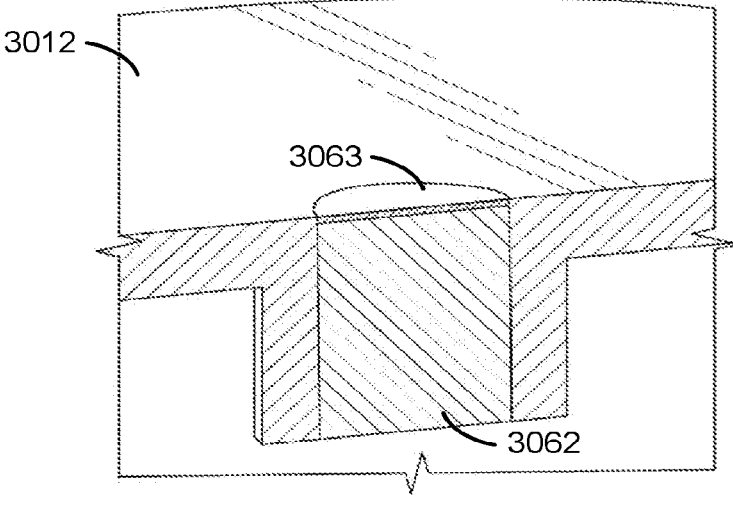
FIG. 30B is a zoomed cross-sectional view of the sealing element of FIG. 30A wherein at least a layer of the vent material is sintered thereby becoming impermeable to the sterilizing gas.

FIG. 30B is a zoomed view of the sealing element of FIG. 30A illustrating sintered layer 3063 of vent 3062, which is impermeable to the sterilizing gas. Because the operative transforming method is application of heat sufficient to sinter the porous polymeric component of vent 3062, batch sterilization and/or vapor sealing of a plurality of applicators may be achieved simultaneously.

In an alternate embodiment, applicators may be enclosed in a container after sterilization is complete. The container may enclose the applicator and function as a moisture barrier. This may aid in batch sterilization and/or vapor sealing of a plurality of applicators. In some embodiments, the container may be a bag, a wrap, a thermoform, or some form of kitted device.

Methods of Manufacturing

Figure 32:
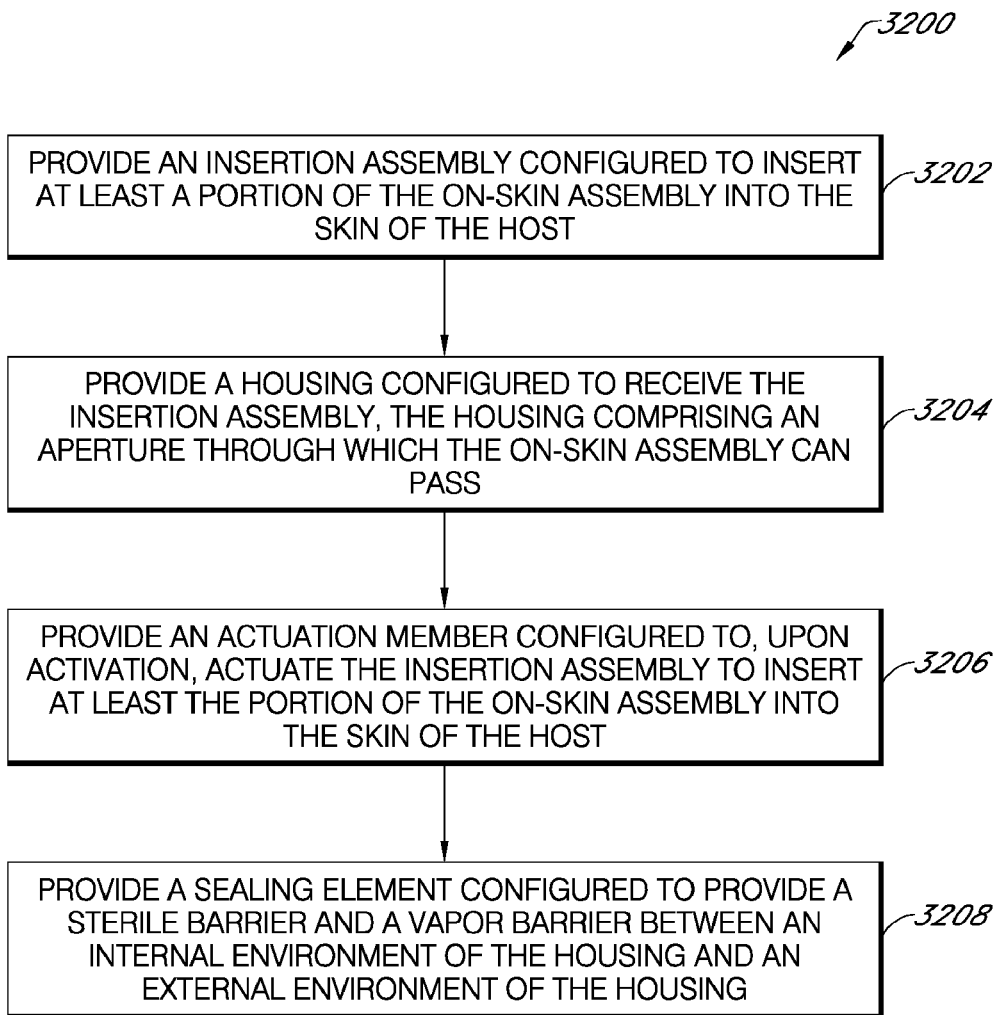
FIG. 32 is a flowchart illustrating a method of manufacturing an applicator for applying an on-skin assembly to skin of a host, in accordance with some embodiments.

FIG. 32 is a flowchart 3200 illustrating a method of manufacturing an applicator for applying on-skin assembly 102 to skin of a host, in accordance with some embodiments. Steps in flowchart 3200 may be performed for manufacturing any applicator as previously described in connection with any of the previous figures. Although certain steps are set forth below, a method of manufacturing such an applicator may comprise more, fewer, or different steps, in the same or different order from that set forth below. Moreover, in some embodiments, this method may be utilized to manufacture a plurality of applicators in batches.

Flowchart 3200 comprises block 3202, which includes providing an insertion assembly configured to insert at least a portion of the on-skin assembly into the skin of the host. For example, on-skin assembly 102 may be provided as previously described in connection with at least FIG. 1B.

Flowchart 3200 further comprises block 3204, which includes providing a housing configured to receive the insertion assembly, the housing comprising an aperture through which the on-skin assembly can pass. Such a housing may be as previously described in connection with any of FIGS. 1A-30.

Flowchart 3200 further comprises block 3206, which includes providing an actuation member configured to, upon activation, actuate the insertion assembly to insert at least the portion of the on-skin assembly into the skin of the host. For example, any actuation member as previously described in connection with any of FIGS. 1A-30 may be provided.

Flowchart 3200 further comprises block 3208, which includes providing a sealing element configured to provide a sterile barrier and/or a vapor barrier between an internal environment of the housing and an external environment of the housing. For example, a sealing element as previously described in connection with any of FIGS. 1A-30 may be provided. For example, such a sealing element may not necessarily comprise a single element but instead may comprise any combination of removable caps, with or without threads, first or second layers, sealing layers, peelable sealing layers, frangible members or caps, flexible members, O-rings, bags, or other seals, as previously described in connection with any combination from FIGS. 1A-30.

FIG. 33 is a flowchart illustrating another method of manufacturing an applicator for applying on-skin assembly 102 to skin of a host, in accordance with some embodiments. Steps in flowchart 3300 may be performed for manufacturing any applicator as previously described in connection with any of the previous FIGs. Although certain steps are set forth below, a method of manufacturing such an applicator may comprise more, fewer, or different steps, in the same or different order from that set forth below. Moreover, in some embodiments, this method may be utilized to manufacture a plurality of applicators in batches.

Flowchart 3300 comprises block 3302, which includes providing an insertion assembly configured to insert at least a portion of the on-skin assembly into the skin of the host. For example, on-skin assembly 102 may be provided as previously described in connection with at least FIG. 1B.

Flowchart 3300 further comprises block 3304, which includes providing a housing configured to receive the insertion assembly, the housing comprising an aperture through which the on-skin assembly can pass. Such a housing may be as previously described in connection with any of FIGS. 1A-30.

Flowchart 3300 further comprises block 3306, which includes providing an actuation member configured to, upon activation, actuate the insertion assembly to insert at least the portion of the on-skin assembly into the skin of the host. For example, any actuation member as previously described in connection with any of FIGS. 1A-30 may be provided.

Flowchart 3300 further comprises block 3308, which includes exposing at least an internal environment of the housing to a sterilizing gas. For example, an internal environment of any housing as previously described in connection with FIGS. 1A-30 may be exposed to a sterilizing gas, such as ethylene oxide (ETO), as previously described or by exposing an applicator to the sterilizing gas before formation, provision, manufacture or application of a sealing element that transforms the housing from permeable to the sterilizing gas to impermeable to at least the sterilizing gas.

Flowchart 3300 further comprises block 3310, which includes allowing for egress of the sterilizing gas from the internal environment of the housing. For example, upon exposing the applicator to the sterilizing gas, the sterilizing gas may be removed and a sufficient amount of time may elapse before continuing the manufacturing process to allow for egress of substantially all sterilizing gas from the internal environment of the housing.

Flowchart 3300 further comprises block 3312, which includes sealing the internal environment of the housing from an external environment of the housing. For example, a sealing element as previously described in connection with any of FIGS. 1A-30 may be provided. For example, such a sealing element may not necessarily comprise a single element but instead may comprise any combination of removable caps, with or without threads, first or second layers, sealing layers, peelable sealing layers, frangible members or caps, flexible members, O-rings, bags, or other seals, as previously described in connection with any combination from FIGS. 1A-30.

In some embodiments, at least sealing the internal environment of the housing from an external environment of the housing is performed simultaneously for a plurality of applicators. In some embodiments, sealing the internal environment of the housing from an external environment of the housing comprises subjecting the plurality of applicators to a partial vacuum exceeding a threshold such that a sealing element of each of the plurality of applicators transitions from being permeable to the sterilizing gas to being impermeable to the sterilizing gas, as previously described in connection with at least FIGS. 27A and 27B.

In some other embodiments, sealing the internal environment of the housing from an external environment of the housing comprises subjecting the plurality of applicators to a physical force sufficient to cause a sealing element of each of the plurality of applicators to transition from a first physical configuration permeable to the sterilizing gas to a second physical configuration impermeable to the sterilizing gas, as previously described in connection with FIGS. 28A and 28B.

In yet other embodiments, sealing the internal environment of the housing from an external environment of the housing comprises subjecting a sealing element, comprising a plurality of perforations, of each the plurality of applicators to a temperature sufficient to at least partially melt each of the sealing elements thereby sealing the plurality of perforations in each of the sealing elements, as previously described in connection with FIGS. 26A and 26B.

In yet other embodiments, sealing the internal environment of the housing from an external environment of the housing comprises subjecting a sealing element, comprising a porous polymeric component, of each of the plurality of applicators to a temperature sufficient to form a sintered layer in the porous polymeric component of each sealing element, as previously described in connection with FIGS. 30A and 30B.

In yet other embodiments, sealing the internal environment of the housing from an external environment of the housing comprises depositing a layer impermeable to the sterilizing gas on at least a portion of each of the plurality of applicators, as previously described in connection with FIG. 29. In some such embodiments, the layer comprises at least one of a metallic foil (e.g. aluminum, titanium), a metallic substrate, aluminum oxide coated polymer, parylene, a polymer coated with a metal applied via vapor metallization, silicon dioxide coated polymer, or any material having a moisture vapor transmission rate less than 10 grams/100 in$^2$ or preferably less than 1 grams/100 in$^2$.

The specification and figures of U.S. patent application Ser. No. 15/387,088, filed on Dec. 21, 2016 and published as U.S. Publication No. 2017/0188910 A1, are hereby incorporated by reference herein in their entirety, and form a part of this application.

It should be appreciated that all methods and processes disclosed herein may be used in any glucose monitoring system, continuous or intermittent. It should further be appreciated that the implementation and/or execution of all methods and processes may be performed by any suitable devices or systems, whether local or remote. Further, any combination of devices or systems may be used to implement the present methods and processes.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of manufacturing a plurality of applicators, wherein each applicator of the plurality of applicators is configured to apply an on-skin assembly to a skin of a host, the method comprising:

providing an insertion assembly for each applicator of the plurality of applicators, wherein each insertion assembly is configured to insert at least a portion of the respective on-skin assembly into the skin of the host;

providing a housing for each applicator of the plurality of applicators, wherein each housing is configured to receive the respective insertion assembly, each housing comprising an aperture through which the respective on-skin assembly is configured to pass;

providing an actuation member for each applicator of the plurality of applicators, wherein each actuation member is configured to, upon activation, actuate the respective insertion assembly to insert at least the portion of the respective on-skin assembly into the skin of the host;

simultaneously exposing at least an internal environment of each housing of the plurality of applicators to an ingress of a sterilizing gas;

simultaneously allowing for an egress of the sterilizing gas from the internal environment of each housing of the plurality of applicators to an external environment;

wherein each housing of the plurality of applicators includes a layer configured to allow for the exposure of the ingress of the sterilizing gas into the internal environment of each housing and for the egress of the sterilizing gas from the internal environment of each housing to the external environment; and providing a removable cap for each applicator of the plurality of applicators, wherein each removable cap is secured to the respective housing, wherein each removable cap has a distal end and a platform raised from the distal end, wherein each platform has at least one aperture.

2. The method of claim 1, further comprising sealing the internal environment of each housing from the external environment of each housing, wherein at least sealing the internal environment of each housing from the external environment of each housing is performed simultaneously for the plurality of applicators.

3. The method of claim 2, wherein sealing the internal environment of each housing from the external environment of each housing comprises subjecting the plurality of applicators to a partial vacuum exceeding a threshold such that a sealing element of each of the plurality of applicators transitions from being permeable to the sterilizing gas to being impermeable to the sterilizing gas.

4. The method of claim 3, wherein sealing the internal environment of each housing from the external environment of the housing comprises subjecting the plurality of applicators to a physical force sufficient to cause the sealing element of each of the plurality of applicators to transition from a first physical configuration permeable to the sterilizing gas to a second physical configuration impermeable to the sterilizing gas.

5. The method of claim 3, wherein sealing the internal environment of each housing from the external environment of the housing comprises subjecting the sealing element, comprising a plurality of perforations, of each the plurality of applicators to a temperature sufficient to at least partially melt each of the sealing elements thereby sealing the plurality of perforations in each of the sealing elements.

6. The method of claim 3, wherein sealing the internal environment of each housing from the external environment of the housing comprises subjecting the sealing element, comprising a porous polymeric component, of each of the plurality of applicators to a temperature sufficient to form a sintered layer in the porous polymeric component of each sealing element.

7. The method of claim 3, wherein sealing the internal environment of each housing from the external environment of the housing comprises depositing a layer impermeable to the sterilizing gas on at least a portion of each of the plurality of applicators.

8. The method of claim 7, wherein the sealing element comprises at least one of a metallic foil, a metallic substrate, an aluminum oxide coated polymer, parylene, a polymer coated with a metal applied via vapor metallization, a silicon dioxide coated polymer, or any material having a moisture vapor transmission rate less than 10 grams/100 in2 or preferably less than 1 grams/100 in2.

9. The method of claim 1, wherein each platform includes a plurality of channels.

10. A method of manufacturing a plurality of applicators, wherein each applicator of the plurality of applicators is configured to apply an on-skin assembly to a skin of a host, the method comprising:

providing an insertion assembly for each applicator of the plurality of applicators, wherein each insertion assembly is configured to insert a sensor of the respective on-skin assembly into the skin of the host, wherein each respective on-skin assembly includes the respective sensor connected to a sensor electronics;

providing a housing for each applicator of the plurality of applicators, wherein each housing is configured to receive the respective insertion assembly, each housing comprising an aperture through which the respective on-skin assembly is configured to pass;

providing an actuation member for each applicator of the plurality of applicators, wherein each actuation member is configured to, upon activation, actuate the respective insertion assembly to insert the respective sensor of the respective on-skin assembly into the skin of the host;

providing a removable cap for each applicator of the plurality of applicators, wherein each removable cap is secured to the respective housing, wherein each removable cap has a distal end and a platform raised from the distal end, wherein each platform has at least one aperture; and providing a layer for each applicator of the plurality of applicators, wherein each layer is coupled to the distal end of the respective removable cap, wherein each layer is configured to seal an internal environment of the respective housing from an external environment of the respective housing.

11. The method of claim 10, wherein each actuation member comprises a material that is permeable to a sterilizing gas.

12. The method of claim 10, further comprising providing a sealing element for each applicator of the plurality of applicators, wherein each sealing element is configured to provide a sterile barrier and a vapor barrier between an internal environment of each housing and the external environment of each housing, wherein each housing comprises a vent configured to be permeable to a sterilizing gas.

13. The method of claim 12, wherein each sealing element is configured to seal the respective vent.

14. The method of claim 12, wherein each sealing element comprises a peelable layer coupled to at least a portion of the respective housing.

15. The method of claim 14, wherein each peelable layer is configured to provide a tamper indication when removed.

16. The method of claim 14, wherein each peelable layer is configured to seal a distal opening of the respective housing.

17. The method of claim 16, wherein each peelable layer is configured to further seal the respective actuation member.

18. The method of claim 14, wherein each peelable layer is configured to seal a vent configured to be permeable to a sterilizing gas.

19. The method of claim 10, wherein each platform includes a plurality of channels.

* * * * *